(12) United States Patent
Pu et al.

(10) Patent No.: US 12,152,182 B2
(45) Date of Patent: Nov. 26, 2024

(54) POLYMER NANOPARTICLES FOR AFTERGLOW MOLECULAR IMAGING

(71) Applicant: NANYANG TECHNOLOGICAL UNIVERSITY, Singapore (SG)

(72) Inventors: Kanyi Pu, Singapore (SG); Qingqing Miao, Singapore (SG)

(73) Assignee: Nanyang Technological University, Signapore (SG)

( * ) Notice: Subject to any disclaimer, the term of this patent is extended or adjusted under 35 U.S.C. 154(b) by 1262 days.

(21) Appl. No.: 16/633,887

(22) PCT Filed: Aug. 1, 2018

(86) PCT No.: PCT/SG2018/050390
§ 371 (c)(1),
(2) Date: Jan. 24, 2020

(87) PCT Pub. No.: WO2019/027370
PCT Pub. Date: Feb. 7, 2019

(65) Prior Publication Data
US 2021/0087463 A1 Mar. 25, 2021

(30) Foreign Application Priority Data

Aug. 1, 2017 (SG) .............................. 10201706237T

(51) Int. Cl.
*A61K 9/00* (2006.01)
*A61B 5/00* (2006.01)
(Continued)

(52) U.S. Cl.
CPC ............ *C09K 11/06* (2013.01); *A61B 5/0071* (2013.01); *A61K 9/0021* (2013.01);
(Continued)

(58) Field of Classification Search
CPC ..................................................... C09K 11/06
See application file for complete search history.

(56) References Cited

U.S. PATENT DOCUMENTS

2013/0272966 A1    10/2013   Xiong et al.

FOREIGN PATENT DOCUMENTS

WO        2017182422 A1    10/2017

OTHER PUBLICATIONS

Chinese Office Action for related application No. 201880045551.6_dated Jan. 13, 2022.
(Continued)

*Primary Examiner* — Paul W Dickinson
(74) *Attorney, Agent, or Firm* — Thomas | Horstemeyer, LLP

(57) ABSTRACT

Disclosed herein are semiconducting polymers of formula I and polymeric composite materials containing said polymer, where said polymer displays near-infrared afterglow luminescence. The polymers of formula I have the following structure:

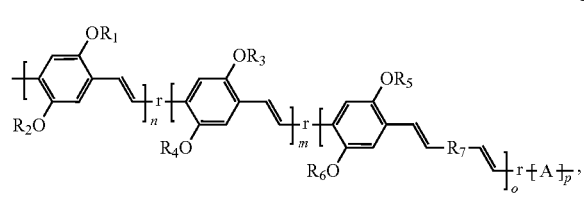

where n, m, o, p, A and $R_1$ to $R_7$ are as defined herein, and r is used to denote a random order to the repeating units.

14 Claims, 28 Drawing Sheets

(51) Int. Cl.
*A61K 49/00* (2006.01)
*C09K 11/06* (2006.01)
*B82Y 5/00* (2011.01)
*B82Y 20/00* (2011.01)
*B82Y 35/00* (2011.01)

(52) U.S. Cl.
CPC ............. *A61K 49/0093* (2013.01); *B82Y 5/00* (2013.01); *B82Y 20/00* (2013.01); *B82Y 35/00* (2013.01); *C09K 2211/1425* (2013.01); *C09K 2211/1466* (2013.01)

(56) References Cited

OTHER PUBLICATIONS

Dr. Mikael Palner et.al, Angew Chem Int Ed Engl., 2015, vol. 54, No. 39.
Chinese Office Action for related application No. 201880045551.6_dated Jun. 27, 2022.
Miao et al. "Molecular afterglow imaging with bright, biodegradable polymer nanoparticles", Nature Biotechnology, 35:11:1102-1110; Oct. 16, 2017.
Palner et al. "Semiconducting Polymer Nanoparticles with Persistent Near-infrared Luminescence for In Vivo Optical Imaging", Angewandte Chemie.
Xie et al. "Self-Assembled Semiconducting Polymer Nanoparticles for Ultrasensitive Near-Infrared Afterglow Imaging of Metastatic Tumors", Advanced Materials, 30:21:1-9, Apr. 2, 2018.
Kemal et al. "Bright, near infrared emitting PLGA-PEG dyedoped CN-PPV nanoparticles for imaging applications", The Royal Society of Chemistry, 7:15255-15264, 2017.
Zaquen et al. "Modifiable poly(p-phenylene vinylene) copolymers towards functional conjugated materials", The Royal Society of Chemistry, 7:4771-4781, 2016.
International Search Report, PCT/SG2018/050390, mailed Jul. 11, 2018.
Written Opinion, PCT/SG2018/050390, mailed Jul. 11, 2018.
Ntziachristos, V. et al., Nat. Biotechnol. 2005, 313-320, 23.
Smith, A. M. et al., Nat. Nanotechnol. 2009, 710-711, 4.
Chu, J. et al., Nat. Biotechnol. 2016, 760-767, 34.
Thorek, D. L. et al., Nat. Med. 2013, 1345-1350, 19.
So, M. K. et al., Nat. Biotechnol. 2006, 339-343, 24.
Liu, H. et al., J. Nucl. Med. 2012, 1579-1584, 53.
De Chermont, Q. L. et al., Proc. Natl. Acad. Sci. USA 2007, 9266-9271, 104.
Maldiney, T. et al., J. Am. Chem. Soc. 2011, 11810-11815, 133.
Maldiney, T. et al., Nat. Mater. 2014, 418-426, 13.
Li, Z. J. et al., J. Am. Chem. Soc. 2015, 5304-5307, 137.
Maldiney, T. et al., Opt. Mater. Express 2012, 261-268, 2.
Abdukayum, A. et al., J. Am. Chem. Soc. 2013, 14125-14133, 135.
Liu, F. et al., Sci. Rep. 2013, 1554, 3.
Maldiney, T. et al., Opt. Mater. 2013, 1852-1858, 35.
Sharma, S. K. et al., Opt. Mater. 2014, 1901-1906, 36.
Shi, J. P. et al., Biomaterials 2015, 260-270, 37.
Toppari, J. et al., Environ. Health Perspect. 1996, 741-803, 104, Suppl 4.
Kobayashi, H. et al., Acc. Chem. Res. 2011, 83-90, 44.
Lovell, J. F. et al., Chem. Rev. 2010, 2839-2857, 110.
Feng, L. et al., Chem. Soc. Rev. 2013, 6620-6633, 42.
Wu, C. et al., Angew. Chem. Int. Ed. 2013, 3086-3109, 52.
Derosa, M. C. et al., Coord. Chem. Rev. 2002, 351-371, 233-234.
Langer, R. Science 1990, 1527-1533, 249.
Scurlock, R. D. et al., J. Am. Chem. Soc. 1995, 10194-10202, 117.
Dodeigne, C. et al., Talanta 2000, 415-439, 51.
Kim, S. et al., Nat. Biotechnol. 2004, 93-97, 22.
Nasr, A. et al., Adv. Ther. 2011, 842-856, 28.
Kola, I. et al., Nat. Rev. Drug Discov. 2004, 711-715, 3.
Willmann, J. K. et al., Nat. Rev. Drug Discov. 2008, 591-607, 7.
Pessayre, D. et al., Handb. Exp. Pharmacol. 2010, 311-365.
Shuhendler, A. J. et al., Nat. Biotechnol. 2014, 373-380, 32.
Carmeliet, P. et al., Nature 2011, 298-307, 473.
Li, Y. et al., Nat. Commun. 2014, 4712, 5.
Yang, K. et al., Adv. Mater. 2012, 1868-1872, 24.
Klebanoff, S. J., J. Leukoc. Biol. 2005, 598-625, 77.
Christensen, R. D. et al., Pediatr. Res. 1985, 1278-1282, 19.
Maldiney, T. et al., ACS Nano 2011, 854-862, 5.
Longmire, M. et al., Nanomedicine 2008, 703-717, 3.
Pu, K. Y. et al., J. Control. Release 2016, 312-322, 240.
Zhen, X. et al., ACS Nano 2016, 6400-6409, 10.
Lécuyer, T. et al., Theranostics 2016, 2488-2524, 6.
Xie, C. et al., Adv. Funct. Mater. 2017, 1605397, 27.
Cui, D. et al., J. Mater. Chem. B 2017, 4406-4409, 5.
Du, X. et al., Biomaterials 2015, 1-11, 69.
Li, L. et al., Chem. Commun. 2014, 13417, 50.
Peng, H. et al., Sensors 2012, 15907-15946, 12.
Xiong, L. et al., J. Mater. Chem. B 2016, 202, 4.

POLYMER NANOPARTICLES FOR AFTERGLOW MOLECULAR IMAGING

CROSS-REFERENCE TO RELATED APPLICATION

This application is the 35 U.S.C. § 371 national stage application of PCT Application No. PCT/SG2018/050390, filed on Aug. 1, 2018, and entitled "POLYMER NANOPARTICLES FOR AFTERGLOW MOLECULAR IMAGING," which claims priority to and the benefit of Singapore Application No. SG 10201706237T, filed on Aug. 1, 2017. The entire content of both of these applications is incorporated by reference herein.

FIELD OF INVENTION

The current invention relates to polymers and polymer nanoparticles that are particularly suited for use in afterglow molecular imaging techniques.

BACKGROUND

The listing or discussion of a prior-published document in this specification should not necessarily be taken as an acknowledgement that the document is part of the state of the art or is common general knowledge.

Optical imaging plays a crucial role in biology and medicine [e.g. See Ntziachristos, V., et al., Nat Biotechnol 23, 313-320 (2005)]. However, the need for real-time light excitation during imaging produces tissue autofluorescence, which compromises imaging sensitivity and specificity in living subjects [e.g. See Smith, A. M., et al., Nat Nanotechnol 4, 710-711 (2009)]. Optical imaging strategies, such as bioluminescence and Cerenkov luminescence, which eliminate the need for concurrent light excitation, have attracted tremendous interest in molecular imaging [e.g. See Chu, J., et al., Nat Biotechnol 34, 760-767 (2016); Thorek, D. L., et al., Nat Med 19, 1345-1350 (2013)]. However, bioluminescence probes require an enzyme/substrate to be able to produce light emission, and so their signals are often affected by the enzyme microenvironment and substrate biodistribution in living animals [e.g. See So, M. K., et al., J. Nat Biotechnol 24, 339-343 (2006)]. In contrast, Cerenkov probes rely on the release of charged particles from radioisotopes, which involve complicated synthetic procedures and exhibit a short lifetime of illuminescence [e.g. See Liu, H., et al., J. Nucl. Med. 53, 1579-1584 (2012)].

Afterglow luminescence is an intrinsic luminescent process that occurs after the end of light excitation [e.g. See de Chermont, Q. L., et al., Proc. Natl. Acad. Sci. USA 104, 9266-9271 (2007)]. Afterglow luminescence is generally caused by the slow release of photons from energy traps in the material in question upon thermal simulation. Although afterglow imaging has tremendous promise for in vivo imaging because of the lack of real-time excitation, only a few inorganic nanoparticles have been shown to produce afterglow luminescence under biologically relevant conditions [e.g. See Maldiney, T., et al., J Am Chem Soc 133, 11810-11815 (2011); Maldiney, T., et al., Nat Mater 13, 418-426 (2014); Li, Z. J., et al., J Am Chem Soc 137, 5304-5307 (2015)]. These articles relate to materials that contain rare-earth heavy metal ions such as europium, praseodymium and chromium [e.g. See Maldiney, T., et al., Opt Mater Express 2, 261-268 (2012); Abdukayum, A., et al., J Am Chem Soc 135, 14125-14133 (2013); Liu, F., et al. Sci Rep-Uk 3 (2013); Maldiney, T., et al., Opt Mater 35, 1852-1858 (2013); Sharma, S. K., et al., Opt Mater 36, 1901-1906 (2014); Shi, J. P., et al., Biomaterials 37, 260-270 (2015)]. Thus, the current generation of afterglow probes are significantly hampered due to toxicity concerns [e.g. See Toppari, J. et al., Environ. Health Perspect. 104 Suppl 4, 741-803 (1996)].

Inorganic afterglow nanoparticles are currently utilized as accumulation probes and have limited targeting applications [e.g. See de Chermont, Q. L., et al., Proc. Natl. Acad. Sci. USA 104, 9266-9271 (2007); Maldiney, T., et al., J Am Chem Soc 133, 11810-11815 (2011); Maldiney, T., et al., Nat Mater 13, 418-426 (2014)] due to the difficulty in modifying the surface of such proteins. Thus, contrast is determined by the difference in probe concentration between the target tissue and the adjacent normal tissue. In contrast to concentration differences, smart activatable probes that undergo a signal intensity change upon detecting molecular targets offer high contrast and real-time information on pathological conditions at the molecular level [e.g. See Kobayashi, H. & Choyke, P. L., Chem. Res. 44, 83-90 (2011); Lovell, J. F., et al., Chem Rev 110, 2839-2857 (2010)].

SUMMARY OF INVENTION

It has been surprisingly found that a group of polymeric materials can display afterglow luminescence in a manner that is suitable for use in biological applications. Thus, in a first aspect of the invention, there is provided a polymeric composite nanoparticle that emits near-infrared afterglow luminescence, the nanoparticle comprising:

(a) a semiconducting polymer of formula I:

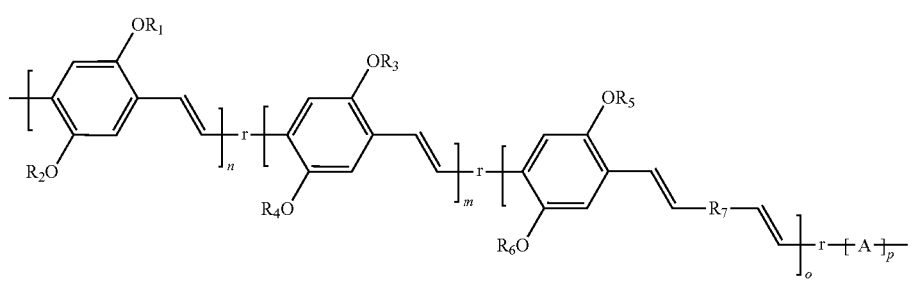

I (b) optionally, an amphiphilic copolymer; and
(c) optionally, a small molecular dye with near-infrared emission, wherein:

when present, the amphiphilic copolymer encapsulates the semiconducting polymer of formula I and, when present, the small molecular dye; and in the polymer of formula I:

$R_1$ to $R_3$ and $R_5$ independently represent an alkyl chain of the formula $C_qH_{2q+1}$, where $1 \leq q \leq 50$, $R_4$ represents a moiety of formula Ia or formula Ib:

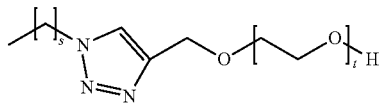

Ia where $1 \leq s \leq 50$ and $10 \leq t \leq 500$

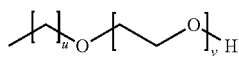

Ib where $1 \leq u \leq 50$ and $10 \leq v \leq 500$;

$R_6$ represents an alkyl chain of the formula $C_qH_{2q+1}$, a moiety of formula Ia or a moiety of formula Ib where q, s, t, u and v are as defined above;

$R_7$ represents a singlet oxygen sensitizing moiety;

each of n, m and o are each greater than or equal to 0 and p is 0 or 1, where at least one of n, m, o and p are greater than 0;

A represents a moiety of formula Ic or Id:

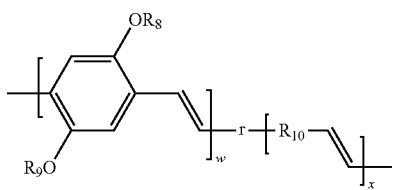

Ic

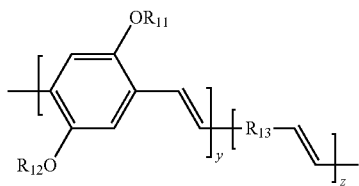

Id where $R_8$ and $R_{11}$ independently represent an alkyl chain of the formula $C_qH_{2q+1}$, where: $1 \leq q \leq 50$;

$R_9$ and $R_{12}$ independently represent an alkyl chain of the formula $C_qH_{2q+1}$, a moiety of formula Ia or a moiety of formula Ib, where q, s, t, u and v are as defined above;

$R_{10}$ and $R_{13}$ independently represent a singlet oxygen sensitizing moiety;

when p is 1, then w, x, y and z, when present, are independently greater than or equal to 0; and the small molecular dye is present when o and p are 0 and is optionally present when:

o is greater than or equal to 20;

p is 1 and x or z is greater than or equal to 20;

the sum of o and x is greater than or equal to 20;

the sum of o and z is greater than or equal to 20;

$(o+x)/(n+m+o+w+x) > 0.05$; or $(o+z)/(n+m+o+y+z) > 0.05$;

the amphiphilic copolymer is present when m, o and p are 0 and optionally present when:

$(m+o+w)/(n+m+o+w+x) > 0.1$; or $(m+o+y)/(n+m+o+y+z) > 0.1$; and provided that when n is greater than 0, one or more of m, o and p are also greater than 0.

In certain embodiments of the first aspect of the invention, p may be 0. In embodiments where p is 0, then the amphiphilic copolymer may be optionally present when:

m is greater than or equal to 20 and m/(n+m+o) is greater than 0.1 and $R^6$ is $C_qH_{2q+1}$, where $1 \leq q \leq 50$;

m is greater than or equal to 20 and (m+o)/(x+y+z) is greater than 0.1 and $R^6$ is a moiety of formula Ia or a moiety of formula Ib; or o is greater than or equal to 20 and (m+o)/(x+y+z) is greater than 0.1 and $R^6$ is a moiety of formula Ia or a moiety of formula Ib.

In certain embodiments of the first aspect of the invention:
(a) n is 0;
(b) the amphiphilic copolymer is present;
(c) when present, each of n, m, o, w, x, y and z independently may have a value of from 5 to 1000;
(d) the number average molecular weight of the polymer of formula I may be from 1,000 to 300,000 Daltons, such as from 1,000 to 100,000 Daltons;
(e) when present, the singlet oxygen sensitizing moiety $R_7$, $R_{10}$ and $R_{13}$ may be independently selected from one or more of the group consisting of metallo-porphyrins, metallo-phthalocyanines, naphthalocyanines, metallo-naphthalocyanines, chlorins, rhodamine, cyanine, carotenoid, anthocyanin, rose bengal, methylene blue and, more particularly, silicon 2,3-naphthalocyanine bis(trihexylsilyloxide), porphyrins (octaethylporphine, tetraphenyl porphyrin), phthalocyanines, tetrapyrroles, transition metal complexes (Ir(III) complexes, Ru(II) complexes, Pt(II) complexes and Os(II) complexes) and boron-dipyrromethene (BODIPY)-based photosensitizers;
(f) the weight to weight ratio of the amphiphilic copolymer to the polymer of formula I may be from 1:1 to 200:1, such as from 1.5:1 to 100:1, such as from 2:1 to 80:1;
(g) when present, the small molecular dye with near-infrared emission may be a singlet oxygen sensitizing compound selected from one or more of the group consisting of metallo-porphyrins, metallo-phthalocyanines, naphthalocyanines, metallo-naphthalocyanines, chlorins, rhodamine, cyanine, carotenoid, anthocyanin, rose bengal, methylene blue and, more particularly, silicon 2,3-naphthalocyanine bis(trihexylsilyloxide), porphyrins (octaethylporphine, tetraphenyl porphyrin), phthalocyanines, tetrapyrroles, transition metal complexes (Ir(III) complexes, Ru(II) complexes, Pt(II) complexes and Os(II) complexes) and boron-dipyrromethene (BODIPY)-based photosensitizers;
(h) when present, the amphiphilic copolymer may be selected from one or more of the group consisting of an alky-substituted chitosan, and more particularly poly(alkyl)-b-poly(ethylene glycol), poly(ethylene glycol)-b-poly(propylene glycol)-b-poly(ethylene glycol), poly(ethylene glycol) methyl ether-block-poly(lactide-co-glycolide) (PEG-PLGA), poly(styrene)-block-poly(acrylic acid) (PS-PAA), poly(styrene-co-maleic anhydride) (PSMA), 1,2-dipalmitoyl-sn-glycero-3-phosphocholine (DPPC) and 1,2-distearoyl-sn-glycero-3-phosphoethanolamine-poly(ethylene glycol) (DSPE-PEG), optionally wherein the amphiphilic copolymer may have a number average molecular weight of from 1,000 to 50,000 Daltons; and/or when present, the amphiphilic copolymer may be selected from one or more of poly(ethylene glycol)-b-poly(propylene glycol)-b-poly(ethylene glycol) (e.g. $(PEG)_{100}$-b-$(PPG)_{65}$-b-$(PEG)_{100}$), 1,2-distearoyl-sn-glycero-3-phosphoethanolamine-poly(ethylene glycol) (DSPE-PEG),

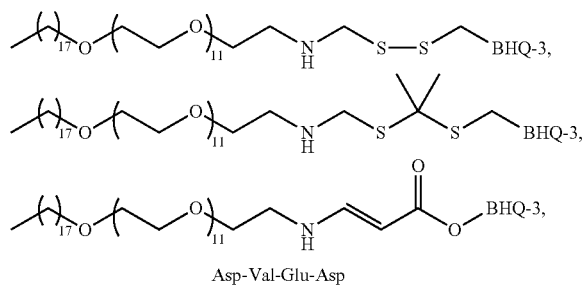

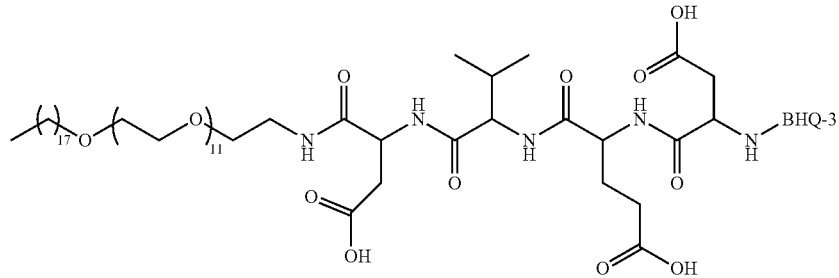

Asp-Val-Glu-Asp and, more particularly,

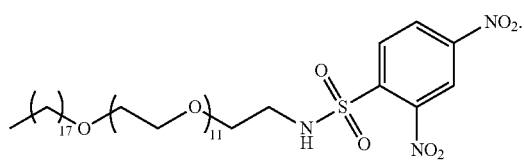

In certain embodiments of the invention, the amphiphilic copolymer, when present, may further comprises a quenching moiety that is cleavable by a reactive moiety in an in vitro or in vivo test site. A suitable quenching moiety may be selected from one or more of the group consisting of:

a thiol-sensitive moiety, such as 2,4-dinitrophenylsulfonyl (DNBS) moiety

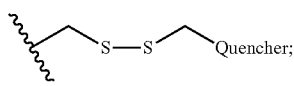

a reactive oxygen species-sensitive moiety

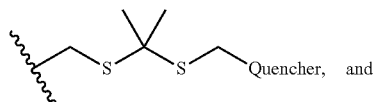

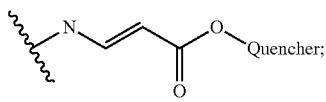

a pH-sensitive moiety such as

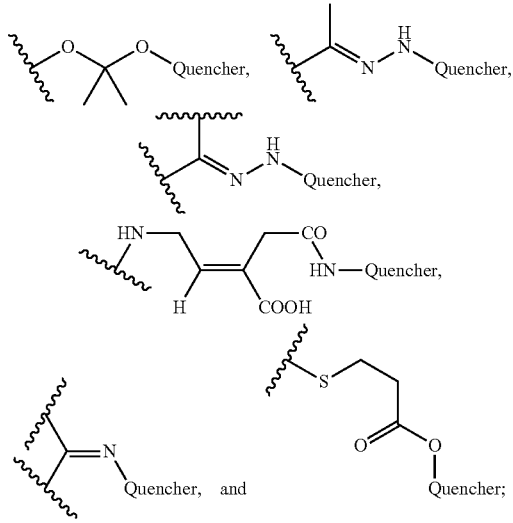

a peptide-quencher moiety, such as a furin-sensitive Arg-Arg-Val-Arg-Quencher, Caspase-3-sensitive Asp-Val-Asp-Quencher, a fibroblast activation protein-alpha (FAPa)-sensitive Gly-Pro-Quencher, a matrix metalloproteinase-2 (MMP-2)-sensitive Gly-Arg-Val-Gly-Leu-Pro-Quencher, a MMP-7-sensitive Gly-Met-Trp-Ser-Leu-Pro-Val-Quencher, a MMP-13-sensitive Leu-Gly-Arg-Met-Gly-Leu-Pro-Quencher, a Cathepsin B-sensitive Lys-lys-Quencher, a Cathepsin D-sensitive Leu-Arg-Phe-Phe-Cys-Ile-Pro-Quencher, a Cathepsin S-sensitive Arg-Leu-Quencher, a Urokinase-sensitive Arg-Gly-Quencher and a Legumain-sensitive Asn-Ala-Ala-Quencher, where the Quencher is a Dark Quencher. A suitable Dark Quencher may be selected from a Black Hole Quencher (BHQ)-1, BHQ-2, BHQ-3, and QSY-7.

In certain embodiments of the invention, the amphiphilic copolymer comprising a quenching moiety may be:

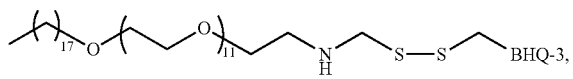

BHQ-3,

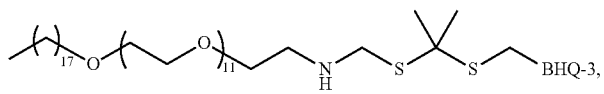

BHQ-3,

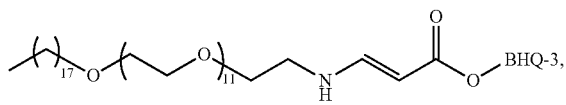

BHQ-3,

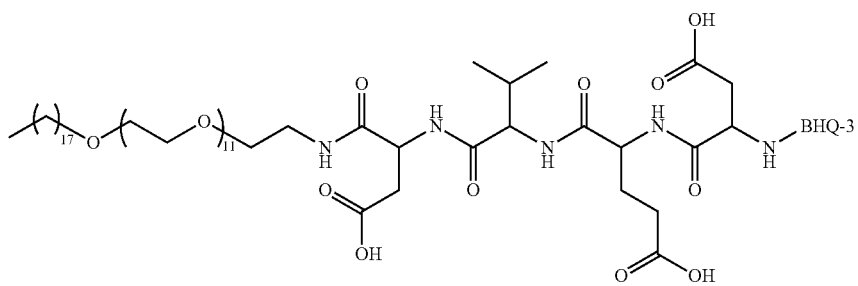

Asp-Val-Glu-Asp and, more particularly,

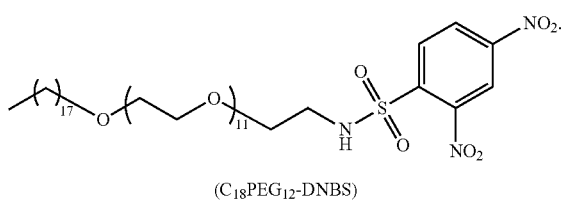

(C₁₈PEG₁₂-DNBS)

In certain embodiments of the invention, the polymer of formula I may be selected from the list of:

(i)

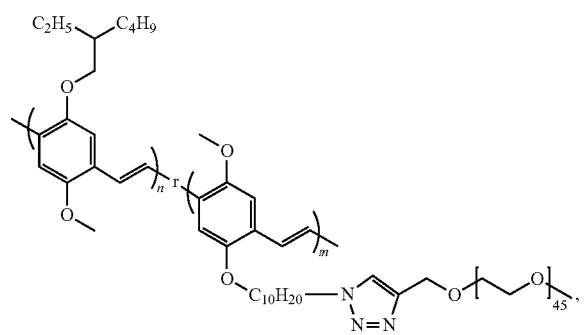

where n an m are as defined in any one o the preceding claims, optionally wherein the number o n and m repeating units provides a polymer having a number average molecular weight of from 25,000 to 200,000 Daltons, such as from 45,000 to 150,000 Daltons, such from 50,000 to 100,000 Daltons, such as around 59,781 Daltons and/or the molar ratio of n repeating units in the polymer is around 88% and the molar ratio of m repeating units in the polymer is around 11% (e.g. the molar ratio of n repeating units in the polymer is from 88.0 to 89.0% and the molar ratio of m repeating units in the polymer is from 11.0 to 12.0%);

(ii)

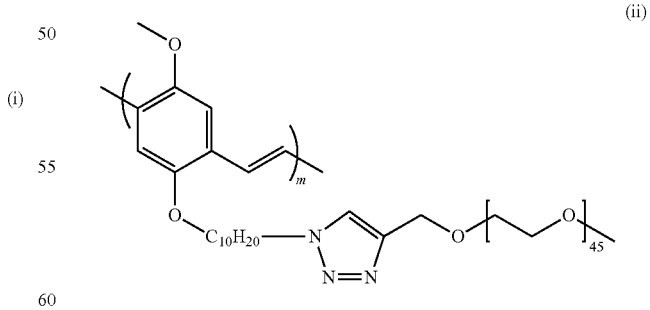

where m is as defined in any one of the preceding claims, optionally wherein the number of m repeating units provides a polymer having a number average molecular weight of from 15,000 to 100,000 Daltons, such as from 20,000 to 75,000 Daltons, such as from 20,000 to 50,000 Daltons, such as around 26,565 Daltons;

(iii)

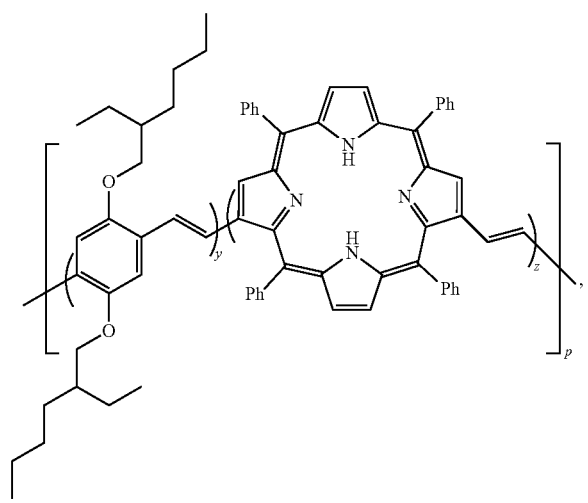

where p is 1 and the number of y and z repeating units provide a polymer having a number average molecular weight of from 5,000 to 20,000 Daltons, such as from 7,000 to 18,000 Daltons, such from 8,900 to 15,000 Daltons, such as around 13,000 Daltons and/or the molar ratio of y repeating units in the polymer is from 85 to 99% and the molar ratio of z repeating units in the polymer is from 1 to 15% (e.g. the molar ratio of y repeating units in the polymer is from 90.0 to 95.0% and the molar ratio of z repeating units in the polymer is from 5.0 to 10.0%).

In a second aspect of the invention, there is provided a semiconducting polymer of formula I:

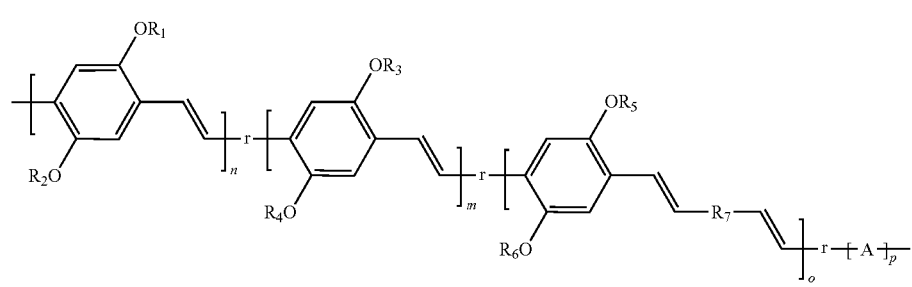

in the polymer of formula I:
$R_1$ to $R_3$ and $R_5$ independently represent an alkyl chain of the formula $C_qH_{2q+1}$, where $1 \leq q \leq 50$,
$R_4$ represents a moiety of formula Ia or formula Ib:

Ia

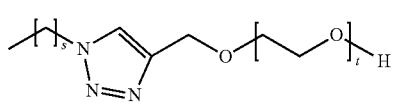

where $1 \leq s \leq 50$ and $10 \leq t \leq 500$

Ib

where $1 \leq u \leq 50$ and $10 \leq v \leq 500$;
$R_6$ represents an alkyl chain of the formula $C_qH_{2q+1}$, a moiety of formula Ia or a moiety of formula Ib, where q, s, t, u and v are as defined above;
$R_7$ represents a singlet oxygen sensitizing moiety;
each of n, m and o are each greater than or equal to 0;
p is 0 or 1;
A represents a moiety of formula Ic or Id:

Ic

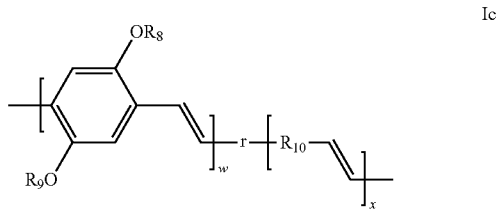

Id

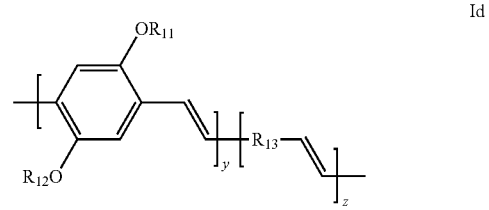

where $R_8$ and $R_{11}$ independently represent an alkyl chain of the formula $C_qH_{2q+1}$, where: $1 \leq q \leq 50$;

$R_9$ and $R_{12}$ independently represent an alkyl chain of the formula $C_qH_{2q+1}$, a moiety of formula Ia or a moiety of formula Ib, where q, s, t, u and v are as defined above;
$R_{10}$ and $R_{11}$ independently represent a singlet oxygen sensitizing moiety;
when p is 1, then w, x, y and z, when present, are independently greater than or equal to 0;
provided that:
when n is greater than 0, one or more of m, o and p are also greater than 0; and
at least one of n, m, o and p are greater than 0.
Embodiments of the second aspect of the invention include those in which:
(i) n may be 0;
(ii) p may be 0;

(iii) the number average molecular weight of the polymer of formula I may be from 1,000 to 100,000 Daltons, such as from 1,000 to 100,000 Daltons;

(iv) when present, each of n, m, o, w, x, y and z may independently have a value of from 5 to 1000;

(v) when present, the singlet oxygen sensitizing moiety $R_7$, $R_{10}$ and $R_{13}$ maybe independently selected from one or more of the group consisting of metallo-porphyrins, metallo-phthalocyanines, naphthalocyanines, metallo-naphthalocyanines, chlorins, rhodamine, cyanine, carotenoid, anthocyanin, rose bengal, methylene blue and, more particularly, silicon 2,3-naphthalocyanine bis(trihexylsilyloxide), porphyrins (octaethylporphine, tetraphenyl porphyrin), phthalocyanines, tetrapyrroles, transition metal complexes (Ir(III) complexes, Ru(II) complexes, Pt(II) complexes and Os(II) complexes) and boron-dipyrromethene (BODIPY)-based photosensitizers.

In embodiments of the second aspect of the invention, the polymer of formula I may be selected from the list of:

(i)

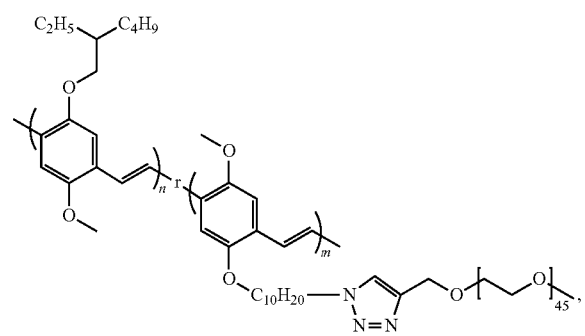

where n and m are as defined in any one of the preceding claims, optionally wherein the number of n and m repeating units provides a polymer having a number average molecular weight of from 25,000 Daltons to 200,000 Daltons, such as from 45,000 Dalton to 150,000 Daltons, such from 50,000 Daltons to 100,000 Daltons, such as around 59,781 Daltons and/or the molar ratio of n repeating units in the polymer is around 88% and the molar ratio of m repeating units in the polymer is around 12% (e.g. the molar ratio of n repeating units in the polymer is from 88.0 to 89.0% and the molar ratio of m repeating units in the polymer is from 11.0 to 12.0%);

(ii)

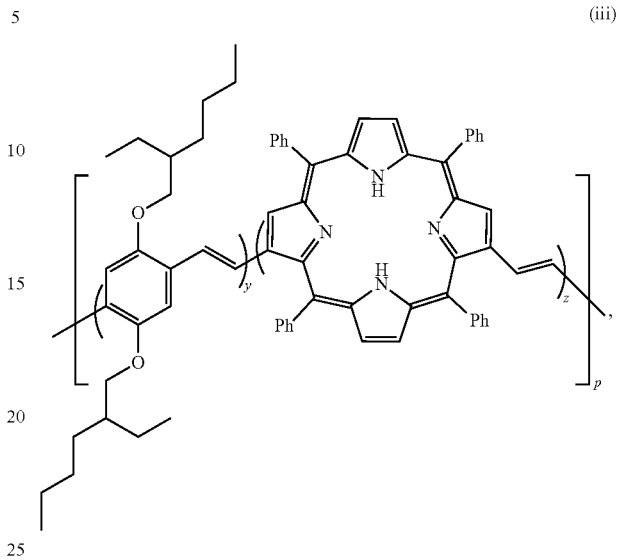

where m is as defined in any one of the preceding claims, optionally wherein the number of m repeating units provides a polymer having a number average molecular weight of from 15,000 Daltons to 100,000 Daltons, such as from 20,000 Dalton to 75,000 Daltons, such from 20,000 Daltons to 50,000 Daltons, such as around 26,565 Daltons; and (iii)

where p is 1 and the number of y and z repeating units provide a polymer having a number average molecular weight of from 5,000 to 20,000 Daltons, such as from 7,000 Daltons to 18,000 Daltons, such from 8,900 Daltons to 15,000 Daltons, such as around 13,000 Daltons and/or the molar ratio of y repeating units in the polymer is from 85 to 99% and the molar ratio of z repeating units in the polymer is from 1 to 15% (e.g. the molar ratio of y repeating units in the polymer is from 90.0 to 95.0% and the molar ratio of z repeating units in the polymer is from 5.0 to 10.0%).

In a third aspect of the invention, there is provided the use of a polymeric composite nanoparticle as defined in the first aspect of the invention and any technically sensible combination of its embodiments, in the preparation of an imaging agent for the diagnosis of a condition or disease in a deep tissue and/or an organ using afterglow luminescence. The imaging may be in vitro or, more particularly, in vivo.

In a fourth aspect of the invention, there is provided a method of performing in vivo imaging in a deep tissue and/or an organ using a polymeric composite nanoparticle as defined in the first aspect of the invention and any technically sensible combination of its embodiments, the method comprising irradiating the polymeric composite nanoparticle with a NIR laser before or after providing the polymeric composite nanoparticle to a living organism (e.g. injecting the polymeric composite nanoparticle subcutaneously, intradermally or intravenously into a living organism), and detecting the afterglow luminescence using an imaging system/device. In various embodiments of the invention, the afterglow luminescence of injected polymer nanoparticle may be re-activated in vivo by subjecting the living organism or part of the living organism of which the polymeric composite nanoparticle was injected subcutaneously, intradermally or intravenously to irradiation by a NIR laser.

In a fifth aspect of the invention, there is provided a polymeric composite nanoparticle as defined in the first aspect of the invention and any technically sensible combination of its embodiments, for use as an imaging agent for the diagnosis of a condition or disease in a deep tissue and/or an organ using afterglow luminescence. The imaging may be in vitro or, more particularly, in vivo.

In embodiments of the third to fifth aspects:
(ai) the in vivo imaging may be performed on a living organism, preferably an animal or a human;
(aii) the in vivo imaging may be for the purpose of mapping lymph nodes and/or visualizing tumors (e.g. breast, lung or liver tumours);
(aiii) the imaging agent may be for use in in vivo imaging for image-guided surgery. For example, the polymeric composite nanoparticle may be one where the amphiphilic copolymer further comprises a quenching moiety that is cleavable by a reactive moiety in an in vitro or in vivo test site as defined above.

In a sixth aspect of the invention, there is provided a use of a polymeric composite nanoparticle as defined above in the first aspect of the invention, where the amphiphilic copolymer further comprises a quenching moiety that is cleavable by a reactive moiety in an in vitro or in vivo test site as defined above (e.g. the amphiphilic copolymer may be $C_{18}PEG_{12}$-DNBS), in the preparation of an imaging agent for use in a method of in vivo imaging of oxidative stress in the liver of a subject, the method comprising the steps of supplying the polymeric composite nanoparticle into a living organism, then irradiating the polymeric composite nanoparticle with a NIR laser, and then detecting the afterglow luminescence in the liver using an imaging system/device.

In a seventh aspect of the invention, there is provided a method of performing in vivo imaging of oxidative stress in the liver of a subject, using a polymeric composite nanoparticle as defined above in the first aspect of the invention, where the amphiphilic copolymer further comprises a quenching moiety that is cleavable by a reactive moiety in an in vitro or in vivo test site as defined above (e.g. the amphiphilic copolymer may be $C_{18}PEG_{12}$-DNBS), the method comprising the steps of injecting the polymeric composite nanoparticle intravenously into a living organism, then irradiating the polymeric composite nanoparticle with a NIR laser, and then detecting afterglow luminescence in the liver using an imaging system/device. In various embodiments of the invention, the afterglow luminescence of injected polymer nanoparticle may be re-activated in vivo by subjecting the living organism or part of the living organism of which the polymeric composite nanoparticle was injected subcutaneously, intradermally or intravenously to irradiation by a NIR laser.

In an eighth aspect of the invention, there is provided a polymeric composite nanoparticle as defined above in the first aspect of the invention, where the amphiphilic copolymer further comprises a quenching moiety that is cleavable by a reactive moiety in an in vitro or in vivo test site as defined above (e.g. the amphiphilic copolymer may be $C_{18}PEG_{12}$-DNBS), for use as an imaging agent for determining oxidative stress in the liver of a subject using afterglow luminescence. Examples of such a test in mice is provided in the examples section.

In embodiments of the sixth to eighth aspects, the oxidative stress in the liver may be used to determine drug-induced hepatotoxicity.

DRAWINGS

FIG. 1a to h show the synthesis and characterization of SPNs. (FIG. 1a) Chemical structures of the SPs (MEHPP, POPPV, PFBT, MEHCPV, BOPPV, MDMOPPV and MEHPPV) and the amphiphilic triblock copolymer (PEG-b-PPG-b-PEG) used for the synthesis of SPNs. (FIG. 1b) Schematic illustration of the preparation of SPNs through nanoprecipitation. (FIG. 1c) Average hydrodynamic diameters of SPNs in 1×PBS buffer (pH=7.4). (FIG. 1d) Representative TEM image of SPN-MEHPPV. (FIG. 1e) White-light (up panel), afterglow luminescence (middle panel) and fluorescence (bottom panel) images of SPN-MEHPP, SPN-POPPV, SPN-PFBT, SPN-MEHCPV, SPN-BOPPV, SPN-MDMOPPV and SPN-MEHPPV in 1×PBS buffer (pH=7.4). Fluorescence and afterglow images of the SPNs were taken at the same absorption intensities at their respective maximum (the absorption is 0.5 after 10-fold dilution of the solution). The fluorescence images were acquired upon excitation at 465 nm for all SPNs except for SPN-MEHPP and SPN-POPPV (430 nm). The afterglow images were acquired for 30 s after the pre-irradiation of SPNs under white light at a power density of 0.1 W/cm² for 1 min. (FIG. 1f) Normalized fluorescence spectra of SPNs in 1×PBS buffer (pH=7.4). (FIG. 1g) Normalized afterglow luminescence spectra of SPN-BOPPV, SPN-MDMOPPV and SPN-MEHPPV in 1×PBS buffer (pH=7.4). (FIG. 1h) Quantification of fluorescence and afterglow intensities of the SPNs in FIG. 1e.

FIG. 2a to 2f show a mechanistic study of the afterglow of SPNs. (FIG. 2a) UV-Vis absorption spectra of MEHPPV (10 µg/mL) before and after light irradiation for 4 h in CHCl₃ (power: 0.1 W/cm²). (FIG. 2b) FTIR spectra of MEHPPV before and after light illumination 24 h in CHCl₃ (power: 0.1 W/cm²). (FIG. 2c) Fluorescence enhancement (F/F₀) of SOSG (1 µM) at 528 nm in the absence or presence of SPN-MEHPPV (1.25 µg/mL) as a function of light irradiation time. (FIG. 2d) Decay of afterglow luminescence of SPN-MEHPPV (62.5 µg/mL) at room temperature. The nanoparticle solution was pre-illuminated for 1 min under white light at a power density of 0.1 W/cm² before the collection of afterglow signals. (FIG. 2e) Afterglow images and intensities of SPN-MEHPPV (62.5 µg/mL) acquired at different temperatures (room temperature and 60° C.), after treatment by $N_2$, $O_2$ purging or in the presence of 50 w/w % $NaN_3$. (FIG. 2f) Proposed mechanism for the afterglow luminescence of PPV-based SP.

FIG. 3a to 3f show $^1O_2$-sensitizer amplified NIR afterglow. (FIG. 3a) Schematic illustration of the proposed mechanism for $^1O_2$-sensitizer-amplified NIR afterglow. (FIG. 3b) Schematic illustration of SPN-NCBS pre-irradiated by an 808 nm laser for afterglow enhancement versus a 514 nm laser. (FIG. 3c) Afterglow luminescence images of 12.5 µg/mL SPN-NCBS (based on the mass of MEHPPV) pre-irradiated at 514 (left) or 808 nm (right). The afterglow images were acquired under bioluminescence model with an acquisition time of 30 s. The nanoparticle solutions were pre-irradiated by 808 or 514 nm laser (1 W/cm²) for 1 min, and then the images were collected for 5 s after removal of the laser source. Fluorescence (FIG. 3d) and NIR-induced afterglow luminescence spectra (FIG. 3e) of SPN-MEHPPV and SPN-NCBS5 in 1×PBS buffer (pH=7.4). (FIG. 3f) Quantification of the absolute fluorescence and afterglow luminescence intensities of SPN-MEHPPV at different doping amounts of NCBS. The error bars represent the standard deviation (n=3).

FIG. 4a to 4e show a tissue-penetration study of NIR afterglow luminescence. (FIG. 4a) Afterglow luminescence (upper panel) and fluorescence (lower panel) imaging of the SPN-NCBS5 solutions through the chicken tissues of different thickness. (FIG. 4b) SBRs for afterglow luminescence and fluorescence of SPN-NCBS5 as a function of tissue depth. *Statistically significant difference in SBRs through chicken tissues at 4 cm (n=3, P<0.01). (FIG. 4c) Schematic illustration of afterglow luminescence imaging through a living mouse, where the SPN-NCBS5 solution is located under the mouse with a depth of 1.7 cm. (FIG. 4d) Afterglow luminescence and fluorescence images of the SPN-NCBS5 solution through a living mouse. The SPN-NCBS5 solutions (62.5 µg/mL, 50 µL) were pre-irradiated with 808 or 514 nm laser (1 W/cm$^2$) for 1 min and then the images were collected within 5 s after removing the laser. The fluorescence images were acquired at 780 nm upon excitation at 710 nm. (FIG. 4e) SBRs for afterglow luminescence and fluorescence imaging in FIG. 4d.

FIG. 5a to 5f show in vivo afterglow imaging of lymph nodes and tumor. (FIG. 5a) Schematic illustration of afterglow luminescence imaging of lymph node. SPN-NCBS5 was pre-irradiated with an 808 nm laser (1 W/cm$^2$) for 1 min followed by storage in $-20°$ C. for one day before being directly used for lymph node imaging. (FIG. 5b) Fluorescence (left) and afterglow luminescence (right) imaging of a lymph node in a living mouse at t=65 min after intradermal injection of SPN-NCBS5 (0.25 mg/mL, 0.05 mL) into the forepaw of mouse. (FIG. 5c) SBRs for afterglow luminescence and fluorescence imaging of lymph node in living mice as a function of post-injection time. In situ renewed afterglow of SPN-NCBS5 was conducted at t=65 min post-injection by irradiation at 808 nm (1 W/cm$^2$) for 1 min. *Statistically significant difference in SBRs between the fluorescence and afterglow luminescence at t=130 min post-injection of SPN-NCBS5 in living mice (n=3, P<0.01). (FIG. 5d) Schematic illustration of afterglow luminescence imaging of xenograft HeLa tumor in mouse models. (FIG. 5e) Afterglow luminescence (upper panel) and fluorescence images (lower panel) of tumor in living mice at representative time-points after systemic administration of SPN-NCBS5 (0.25 mg/mL, 0.2 mL) via tail vein injection. The tumor was on the right shoulder as indicated by the white dashed circles and arrows. (FIG. 5f) SBRs for afterglow luminescence and NIR fluorescence imaging of tumor in living mice as a function of time. Intensity values are the mean±s.d. for n=3 mice. The error bars were based on standard deviations (mice n=3). Afterglow luminescence images were acquired for 180 s after irradiation at 808 nm (0.5 W/cm$^2$) for 1 min. The fluorescence images were acquired for 0.1 s at 780 nm upon excitation at 710 nm.

FIG. 6a to 6h show in vivo afterglow luminescence imaging of drug-induced hepatotoxicity. (FIG. 6a) Schematic illustration of the design and turn-on mechanism of biothiol-activatable afterglow probe (SPN-thiol). (FIG. 6b) Afterglow luminescence spectra of SPN-thiol (12.5 µg/mL) in the absence or presence of Cys (1 mM) in 1×PBS buffer (pH=7.4). (FIG. 6c) Afterglow luminescence images of SPN-thiol (12.5 µg/mL) in the presence of Cys, Hcy, GSH and other amino acids (1 mM) in 1×PBS (pH=7.4) at 37° C. (FIG. 6d) Afterglow luminescence intensities of SPN-thiol in the presence of Cys, Hcy, GSH and other amino acids (1 mM) in 1×PBS (pH=7.4) at 37° C. 1: Blank, 2: Arg, 3: Asn, 4: Gln, 5: Gly, 6: His, 7: Leu, 8: Lys, 9: Met, 10: Pro, 11: Ser, 12: Val, 13: GSH, 14: Hcy, 15: Cys (FIG. 6e) Fitted calibration curve of the intensity of afterglow luminescence of SPN-thiol as a function of the concentration of Cys. (FIG. 6f) Schematic representation of the mechanism of APAP-induced toxicity with the effects of depletion of GSH resulting in the inactivated afterglow and NAC to remediate the depletion to activate the afterglow. (FIG. 6g) Representative afterglow luminescence images of mice treated intraperitoneally with APAP (300 mg/kg), saline, or NAC (200 mg/kg) with APAP (300 mg/kg), followed by an intravenous injection of SPN-thiol (0.25 mg/mL, 0.2 mL) at t=20 min later. Afterglow luminescence images were acquired for 180 s after in situ renew by irradiation at 808 nm (1 W/cm$^2$) for 1 min. (FIG. 6h) SBRs for afterglow luminescence and NIR fluorescence imaging of liver in living mice as a function of time. Intensities values are the mean±s.d. for n=3 mice. *Statistically significant difference in the afterglow luminescence intensities between saline- and APAP-treated groups at t=2 h post-injection of SPN-thiol (n=3, P<0.01); **No statistically significant differences were seen between saline and APAP/NAC treated groups at t=2 h post-injection of SPN-thiol (n=3, P>0.05).

FIG. 9a to 9c show (FIG. 9a) Fluorescence images (upper) and afterglow luminescence images (lower) of various SPs in THF solution at the same optical densities at their respective maximum absorption wavelength (the absorption is 0.5 after 10-fold dilution of the solution). Fluorescence images of all the SPs were acquired for 0.1 s with excitation at 465±10 nm, and emission at 580±10 nm except that MEHCPV and POPPV were excited at 430 nm and acquired at 520±10 nm. For the afterglow luminescence images, all the SPs were illuminated for 1 min by white light at power of 0.1 W/cm$^2$ and the signal were acquired 30 s with an open filter. (FIG. 9b) Normalized fluorescence spectra of SPs in THF solution. SPs including BOPPV, MDMOPPV, and MEHPPV are excited at 455 nm; PFBT, MEHCPV, POPPV, and MEHPP are excited at 440, 420, 360 and 320 nm, respectively. (FIG. 9c) Quantification of fluorescence and afterglow luminescence intensities for the SPs in THF. Error bars represent standard deviation of three separate measurements. Compared with MEHPPV, MEHCPV with an electron withdrawing cyan group on the vinylene backbone had the 5.1-fold lower afterglow luminescence. This is because the electron withdrawing substituents could slow down $^1O_2$ oxidation and thus decrease afterglow luminescence. Similarly, the substituent groups of POPPV have weaker electron donating groups than BOPPV, MDMOPPV, and MEHPPV [e.g. See Abdukayum, A., et al., J Am Chem Soc 135, 14125-14133 (2013)]; they showed weaker afterglow luminescence intensity.

FIG. 10a to 10f show UV-Vis absorption spectra of (FIG. 10a) MDMOPPV and (FIG. 10d) BOPPV (10 µg/mL) before and after light irradiation for 4 hours in CHCl$_3$ (power: 0.1 W/cm$^2$); Partial $^1$H NMR spectra of (FIG. 10b) MDMOPPV and (FIG. 10e) BOPPV before and after light illumination overnight in CDCl$_3$ (power: 0.1 W/cm$^2$) and Fourier-transform infrared spectroscopy (FT-IR) spectra of MDMOPPV (FIG. 10c) and (FIG. 10f) BOPPV before and after light illumination overnight in CHCl$_3$ (power: 0.1 W/cm$^2$).

FIG. 11a to 11d show UV-Vis absorption spectra of MEHPP (FIG. 11a), POPPV (FIG. 11b), PFBT (FIG. 11c), and MEHCPV (FIG. 11d) (10 µg/mL) before and after light irradiation for 4 hours in CHCl$_3$ (power: 0.1 W/cm$^2$).

Figure 12:
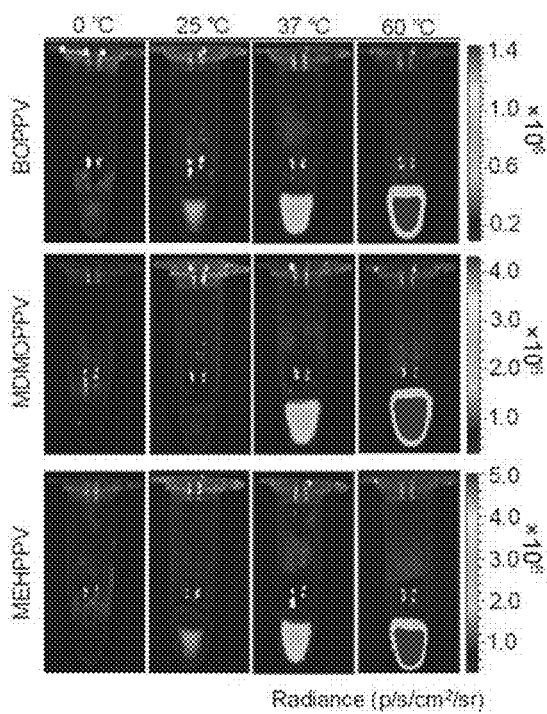

FIG. 12 shows afterglow luminescence images of SPN-BOPPV (upper, 180 µg/mL), SPN-MDMOPPV (middle, 83.3 µg/mL), SPN-MEHPPV (lower, 62.5 µg/mL) response to temperature by an IVIS Spectrum imaging system acquired for 30 s with open filter.

Figure 13:
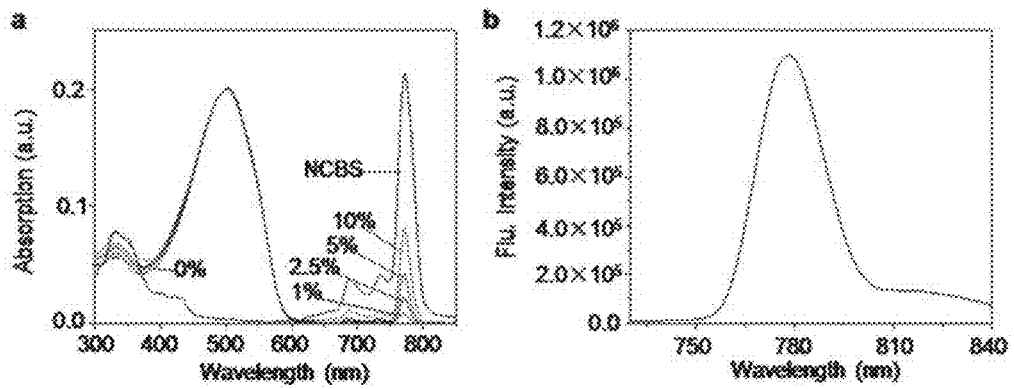

FIGS. 13a and 13b show (FIG. 13a) UV-Vis absorption of SPN-MEHPPV at various doping amounts of NCBS and NCBS only in PBS buffer (pH=7.4) and (FIG. 13b) Fluorescence spectra of SPN-NCBS5 in 1×PBS buffer (pH=7.4). Excitation: 710 nm.

FIGS. 14a and 14b show (FIG. 14a) representative TEM image of SPN-NCBS5 and (FIG. 14b) DLS of SPN-NCBS in 1×PBS buffer (pH=7.4).

FIG. 15a to 15c (FIG. 15a) Fluorescence images of SPN-MEHPPV at various doping amounts of NCBS (i.e., 0%, 1%, 2.5%, 5% and 10%) at the concentration of 12.5 μg/mL (based on the mass of MEHPPV) acquired for 0.1 s with excitation at 465±10 nm and emission at 580±10 nm or 780±10 nm; (FIG. 15b) Normalized fluorescence spectra of SPN-MEHPPV at various doping amount of NCBS (i.e., 0%, 1%, 2.5%, 5% and 10%) in 1×PBS buffer (pH=7.4). Excitation: 465 nm and (FIG. 15c) Afterglow luminescence (left) and fluorescence (right) images of NCBS nanoparticles (NCBS precipitated with PEG-b-PPG-b-PEG) at a concentration of 0.625 μg/mL (based on the mass of NCBS). The fluorescence images were acquired at 580±10 or 780±10 nm upon excitation at 465±10 nm. The afterglow images were acquired under bioluminescence model with the acquisition time of 30 s. The nanoparticle solutions were pre-irradiated with an 808 nm laser (1 W/cm$^2$) for 1 min and then the images were collected for 5 s after removal of the laser.

FIGS. 16a and 16b show (FIG. 16a) afterglow luminescence of SPN-NCBS5 (12.5 μg/mL) after illumination by 808 nm laser at different power densities and (FIG. 16b) Afterglow luminescence of SPN-NCBS5 (12.5 μg/mL) at different light irradiation time by 808 nm laser at power density of 1 W/cm$^2$. Error bars represent standard deviation of three separate measurements.

FIGS. 17a and 17b show (FIG. 17a) fitted calibration curve of the intensity of afterglow luminescence of SPN-NCBS5 after illumination by 808 nm or 514 nm (1 W/cm$^2$) laser as a function of the concentration and (FIG. 17b) fluorescence enhancement (F/F$_0$) of SOSG (1 μM) at 528 nm in the absence or presence of SPN-NCBS5 (1.25 μg/mL) as a function of the irradiation time by 808 nm or 514 nm laser. Error bars represent standard deviation of three separate measurements.

FIG. 18a to 18f show (FIG. 18a) chemical structure of meso-tetraphenylporphyrin (TPP); (FIG. 18b) UV-Vis absorption of SPN-MEHPPV with various doping amounts of TPP in PBS buffer (pH=7.4); (FIG. 18c) fluorescence (left) and afterglow luminescence (right) images of SPN-MEHPPV at various doping amounts of TPP in PBS buffer (pH=7.4). Fluorescence images were acquired for 0.1 s with excitation at 465±10 nm and emission at 580±10 nm and 660±10 nm. Bioluminescence images were acquired for 30 s at 580±10 nm and 660±10 nm; fluorescence (FIG. 18d) and afterglow luminescence (FIG. 18e) spectra of SPN-MEHPPV at various doping amount of TPP in PBS buffer (pH=7.4). Afterglow luminescence spectra were acquired for 30 s at each filter from 540±10 nm to 840±10 nm and were analyzed by region of interest (ROI) analysis; (FIG. 18f) quantification of fluorescence and afterglow luminescence intensities of SPN-MEHPPV at various doping amounts of TPP. Error bars represent standard deviation of three separate measurements. The total fluorescence was obtained by integrating the area of the fluorescence spectra by Origin 9.0. Total afterglow luminescence was obtained with open filters and region-of-interest (ROI) analysis. For the fluorescence spectra, [SPN]=2.5 μg/mL based on MEHPPV components and excitation wavelength was 465 nm. For the afterglow luminescence spectra, the fluorescence and afterglow luminescence images, [SPN]=62.5 μg/mL based on MEHPPV components. All SPNs were irradiated by white light for 1 min before acquisition of afterglow luminescence (power: 0.1 W/cm$^2$).

FIG. 19a to 19h show (FIG. 19a) UV-Vis absorption, (FIG. 19b) fluorescence and (FIG. 19c) afterglow luminescence spectra of SPN-MDMOPPV at various doping amount of NCBS in PBS buffer (pH=7.4); (FIG. 19d) quantification of fluorescence and afterglow luminescence intensities of SPN-MDMOPPV at various doping amount of NCBS; (FIG. 19e) UV-Vis absorption, (FIG. 19f) fluorescence, and (FIG. 19g) afterglow luminescence spectra of SPN-MDMOPPV at various doping amounts of TPP in PBS buffer (pH=7.4) and (FIG. 19h) quantification of fluorescence and afterglow luminescence intensities of SPN-MDMOPPV with various TPP doping amounts. Error bars represent standard deviation of three separate measurements. The total fluorescence was obtained by integrating the area of the fluorescence spectra by Origin 9.0. Afterglow luminescence spectra were acquired for 30 s at each filter from 540±10 nm to 840±10 nm and then quantitated by region-of-interest (ROI) analysis. The total afterglow luminescence was obtained for 30 s with open filters and ROI analysis. For the fluorescence spectra, [SPN]=3.3 μg/mL based on MDMOPPV components with excitation wavelength of 465 nm. For the afterglow luminescence spectra, [SPN]=83.3 μg/mL based on MDMOPPV components. All the SPNs were irradiated by white light for 1 min before acquisition of afterglow luminescence (power: 0.1 W/cm$^2$).

Figure 20:
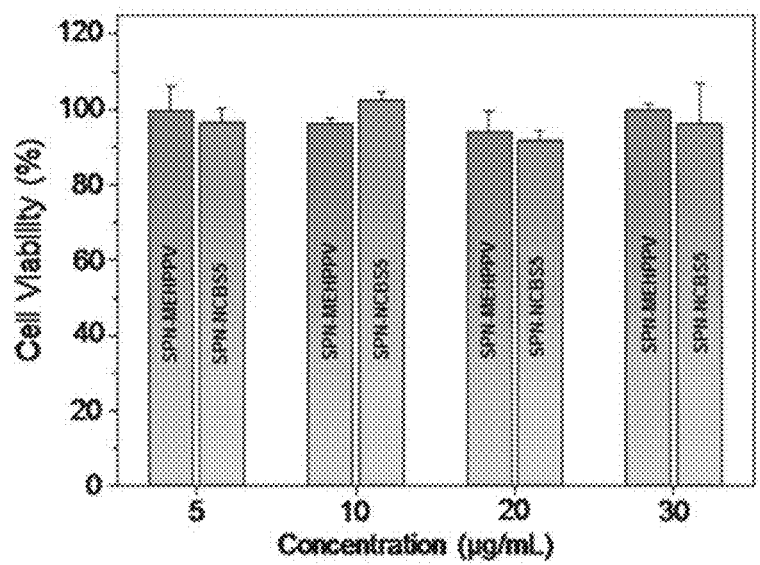

FIG. 20 shows cytotoxicity studies of SPN-MEHPPV and SPN-NCBS5. In vitro viability of HeLa cells treated with SPN-MEHPPV and SPN-NCBS5 solutions at concentrations of 5, 10, 20, and 30 μg/mL for 24 h. The percentage of viable cells after SPN treatment is calculated relative to cells treated with the same volume of saline (viability was arbitrarily defined as 100%). Error bars represent standard deviations of three separate measurements.

Figure 21:
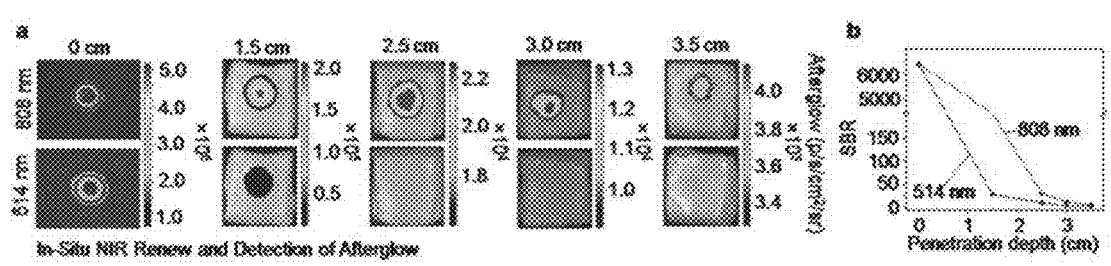
Figure 22:
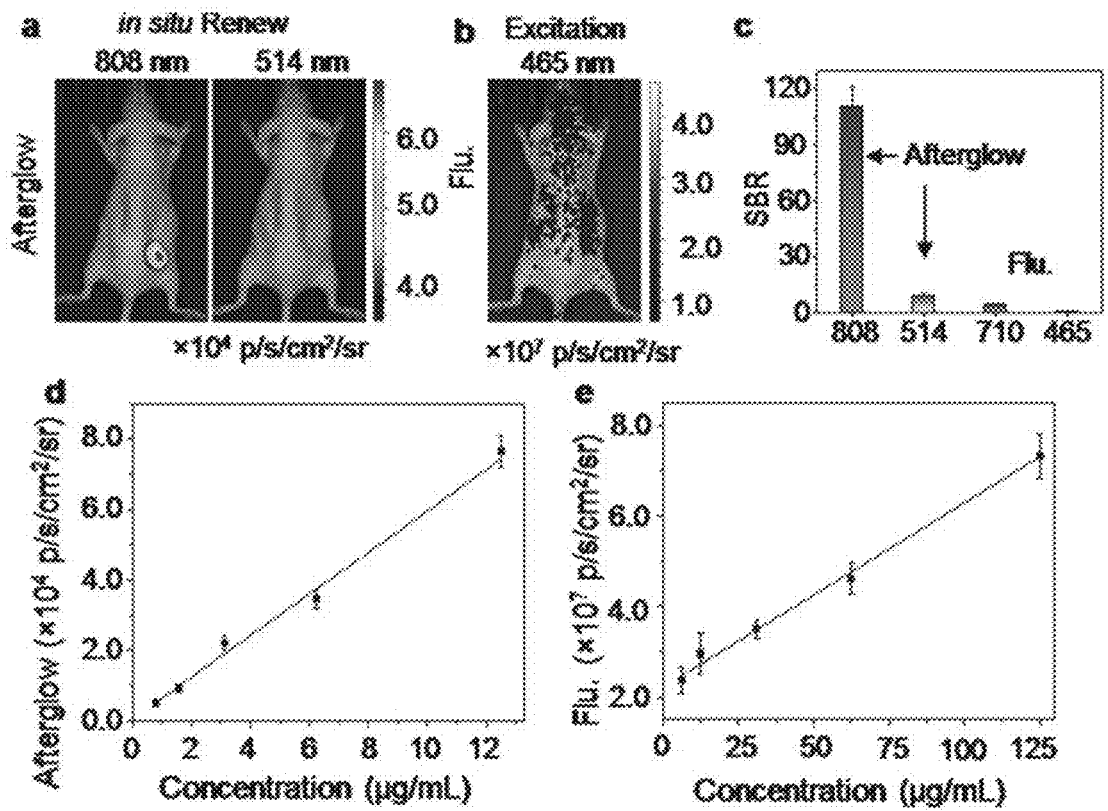

FIGS. 21a and 21b show (FIG. 21a) afterglow luminescence imaging of the SPN-NCBS5 solutions through the chicken tissues with different thicknesses in situ pre-irradiation by 808 nm (upper) or 514 nm (lower) and (FIG. 21b) SBRs for afterglow luminescence as a function of the depth of chicken tissue. Error bars represent standard deviations of three separate measurements.

FIG. 22a to 22e show (FIG. 22a) afterglow luminescence images of SPN-NCBS5 through a living mouse after in situ pre-illumination by 808 nm (1 W/cm$^2$) (left) or 514 nm (middle) as well as (FIG. 22b) fluorescence image (right) excited at 465 nm; (FIG. 22c) SBRs for afterglow luminescence and fluorescence in FIGS. 22a & b; (FIG. 22d) fitted calibration curve of the vivo intensity of afterglow luminescence of SPN-NCBS5 through a living mouse after pre-illumination by 808 nm (1 W/cm$^2$) as a function of the concentration of the nanoparticles (LOD: 40 ng/mL) and (FIG. 22e) fitted calibration curve of the vivo fluorescence intensity of SPN-NCBS5 through a living mouse as a function of the concentration of the nanoparticles (excitation: 710 nm, LOD: 8550 ng/mL). Error bars represent standard deviations of three separate measurements.

FIG. 23a to 23d show (FIG. 23a) calculation of SBRs from the in vivo afterglow luminescence image of a mouse with the subcutaneous inclusions of SPN-NCBS5 (12.5 μg/mL, 50 μL); (FIG. 23b) SBRs for afterglow luminescence and fluorescence of the subcutaneous inclusions of SPN-NCBS5 (12.5 μg/mL, 50 μL). SBR=[(afterglow signal, ROI 1)−(background 2, ROI 3)]/[(background 1, ROI 2)−(background 2, ROI 3)]; in vivo intensity of (FIG. 23c) afterglow luminescence and (FIG. 23d) fluorescence of subcutaneous inclusion of the nanoparticle as a function of the concentration of SPN-NCBS5. Error bars represent standard deviation of three separate measurements.

Figure 24:
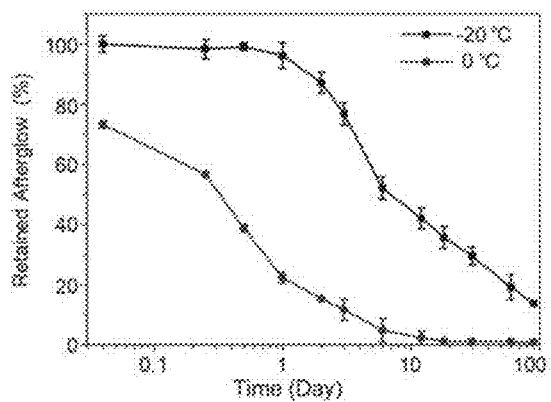

FIG. 24 shows afterglow luminescence intensities of SPN-NCBS (62.5 µg/mL) as a function of time stored at 0° C. or −20° C. after illumination for 1 min by 808 nm (power: 1 W/cm$^2$). Error bars represent standard deviation of three separate measurements.

Figure 25:
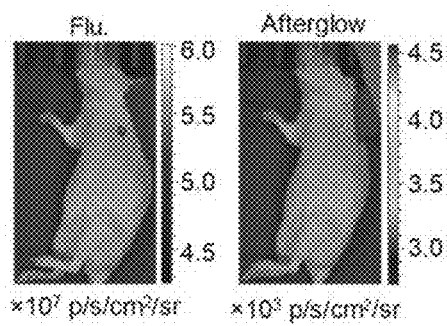

FIG. 25 shows fluorescence (left) and afterglow luminescence (right) images of lymph node in living mouse at t=30 min after intradermal injection of SPN-NCBS5 (0.25 mg/mL, 0.05 mL) into mice forepaws. The fluorescence image was acquired for 0.1 s at 780±10 nm upon excitation at 465±10 nm. The afterglow luminescence image was acquired for 180 s with an open filter without light re-irradiation.

Figure 26:
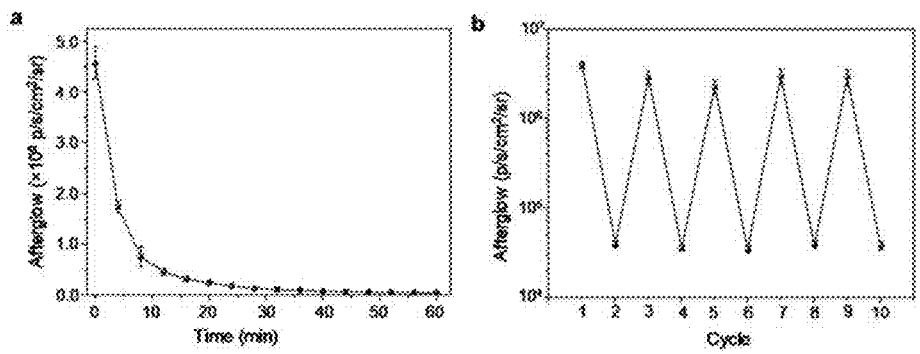

FIGS. 26a and 26b show (FIG. 26a) In vivo afterglow decay of SPN-NCBS5 recorded after light irradiation for 1 min by 808 nm (power: 1 W/cm$^2$) and (FIG. 26b) The afterglow luminescence intensities of the subcutaneous inclusion SPN-NCBS5 as a function of the cycle number of light activation. Error bars represent standard deviation of three separate measurements.

Figure 27:
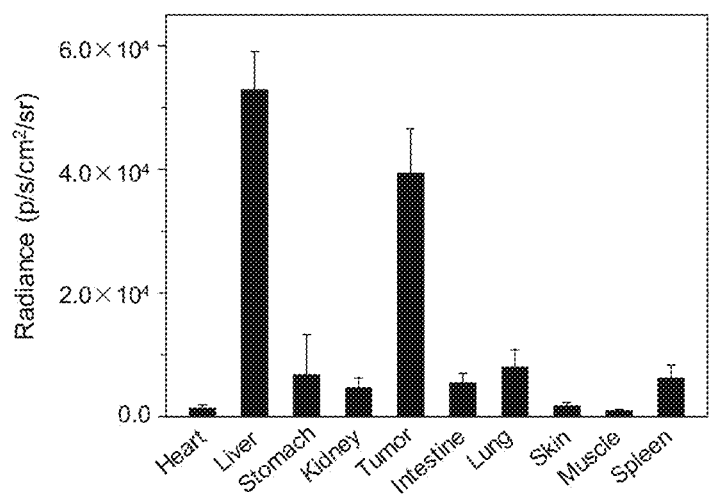

FIG. 27 shows ex vivo afterglow luminescence quantification of major organs of mice 48 h after systemic administration of SPN-NCBS5 (0.25 mg/mL, 0.2 mL) via tail vein injection. Values are the mean±s.d. for n=3 mice.

FIGS. 28a and 28b show (FIG. 28a) TEM images of SPN-thiol and (FIG. 28b) DLS of SPN-thiol in 1×PBS buffer (pH=7.4). Error bars represent standard deviation of three separate measurements.

FIG. 29a to 29d show (FIG. 29a) fluorescence spectra of SPN-thiol in 1×PBS buffer in the presence of different concentration of Cys (pH=7.4); (FIG. 29b) the fluorescence intensities of SPN-thiol at 780 nm as a function of the concentrations of Cys; (FIG. 29c) fluorescence intensities of SPN-thiol at 780 nm in 1×PBS in the presence of Cys, Hcy, GSH and other amino acids (1 mM) at 37° C. and (FIG. 29d) Fluorescence images of SPN-thiol (12.5 µg/mL) in the presence of Cys, Hcy, GSH and other amino acids (1 mM) at 37° C. Error bars represent standard deviation of three separate measurements.

Figure 30:
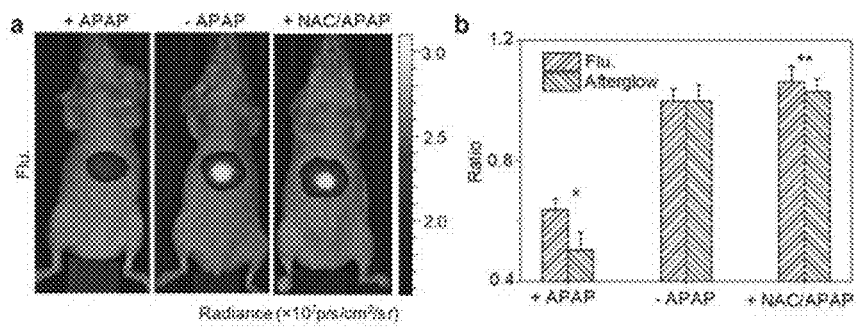

FIGS. 30a and 30b show (FIG. 30a) Representative fluorescence images of mice treated i.p. with APAP (300 mg/kg), saline, or NAC (200 mg/kg) with APAP (300 mg/kg), followed by an intravenous injection of SPN-thiol (0.25 mg/mL, 0.2 mL) at t=20 min later and (FIG. 30b) Ratiometric value for the fluorescence and afterglow luminescence intensities of all the groups (APAP treated, APAP untreated, NAC/APAP treated) towards that of APAP untreated group. Values are the mean±s.d. for n=3 mice. *Statistically significant differences were seen in the fluorescence and afterglow luminescence between APAP-untreated and APAP-treated groups (n=3, P<0.05); **No statistically significant difference between the APAP-untreated and the APAP with NAC remediation group (n=3, P>0.05).

Figure 31:
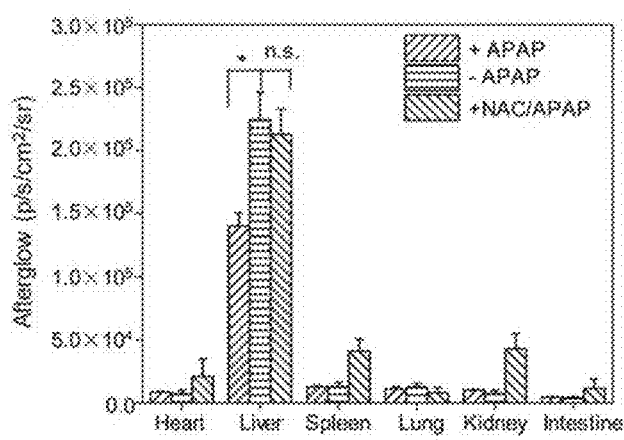

FIG. 31 shows ex vivo afterglow luminescence quantification of major organs of mice 3.5 h after systemic administration of SPN-thiol. *Statistically significant difference in the afterglow luminescence intensities between APAP untreated and APAP treated group (n=3, P<0.05); **No statistically significant difference between APAP untreated and APAP with NAC remediation group (n=3, P>0.05).

Figure 32:
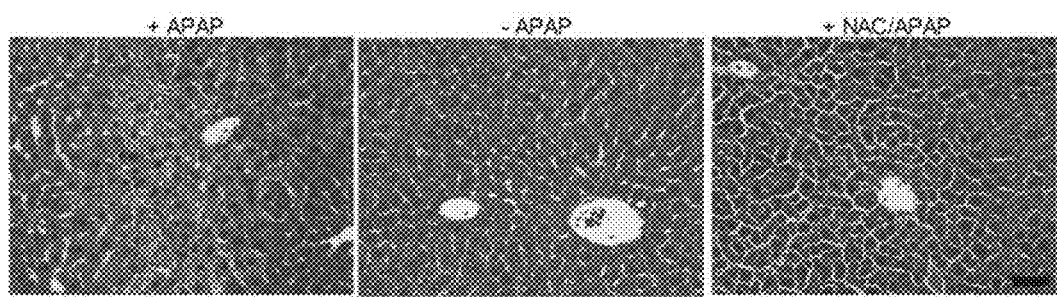

FIG. 32 shows representative histology (H&E) of the livers of mice at t=3.5 h after treatment with APAP (300 mg/kg). Scale bar represent 50 µm.

FIG. 33a to 33e show (FIG. 33a) Schematic illustration of degradation of SPN-MEHPPV by myeloperoxidase (MPO); (FIG. 33b) UV-Vis absorption spectra of SPN-NCBS5 (25 µg/mL) solutions before treatment (Blank, left) and after 4 times treatment with 300 µM $H_2O_2$ alone ($H_2O_2$, middle) or 300 µM $H_2O_2$ and 50 µg/mL MPO ($H_2O_2$+ MPO, right) at 37° C. for 8 h in phosphate buffer (50 mM, pH=7.0) containing NaCl (150 mM); (FIG. 33c) White-light (up panel), fluorescence (middle panel) and afterglow luminescence (bottom panel) images of SPN-NCBS5 (25 µg/mL) without treatment (Blank, left) or treatment with 300 µM $H_2O_2$ alone ($H_2O_2$, middle) or 300 µM $H_2O_2$ and 50 µg/mL MPO ($H_2O_2$+ MPO, right) at 37° C. for 8 h in phosphate buffer (50 mM, pH=7.0) containing NaCl (150 mM). The nanoparticle solutions were pre-irradiated by 808 nm laser (1 W/cm$^2$) for 1 min before collection of afterglow signals. The afterglow images were acquired under bioluminescence model with the acquisition time of 30 s. The fluorescence images were acquired for 0.1 s at 780 nm upon excitation at 465 nm; (FIG. 33d) Quantification of the afterglow luminescence intensities in c. The error bars were based on standard deviations (n=3) and; (FIG. 33e) Gel permeation chromatography (GPC) traces of the nanoparticle inclusions. Freeze dried samples were dissolved in THF solution for GPC test. Wavelength: 500 nm.

FIGS. 34a and 34b show (FIG. 34a) fluorescence images of liver in living mice at representative time-points after systemic administration of SPN-NCBS5 (0.25 mg/mL, 0.2 mL) via tail vein injection. The fluorescence images were acquired for 0.1 s at 780 nm upon excitation at 710 nm and (FIG. 34b) quantification of NIR fluorescence of liver in living mice as a function of time. Intensity values are the mean±s.d. for n=3 mice. The error bars were based on standard deviations (mice n=3).

Figure 35:
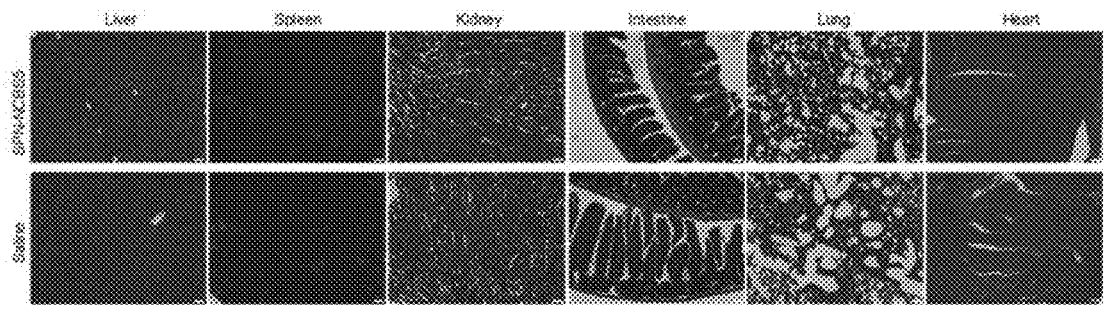

FIG. 35 shows representative histology (H&E) of the mice organs 3 day after systematic administration of SPN-NCBS5 (0.25 mg/mL, 0.2 mL) or saline via tail vein injection. Scale bar represent 50 µm.

Figure 36:
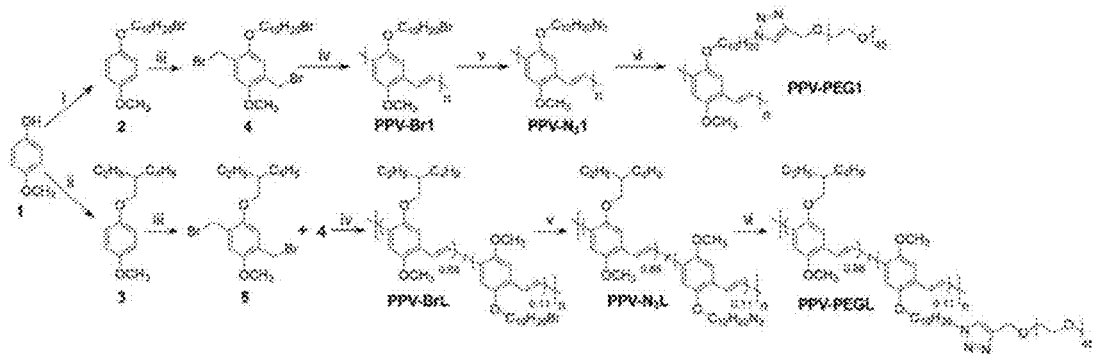

FIG. 36 shows the synthetic routes of PPV-PEG1 and PPV-PEGL. Reagents and conditions: (i) 1,10-dibromodecane, sodium methoxide, ethanol, refluxing, 2 h. (ii) 2-ethylhexyl bromide, sodium methoxide, ethanol, refluxing, 2 h. (iii) paraformaldehyde, HBr (33 wt % in acetic acid), acetic acid, 70° C., 4 h. (iv) potassium tert-butoxide, tetrahydrofuran (THF), 25° C., overnight. (v) sodium azide, THF/N,N-dimethylformamide (DMF), 40° C., overnight. (vi) CuBr, N,N,N',N'',N'''-pentamethyldiethylenetriamine (PMDETA), PEG-alkyne, THF, 25° C., 48 h.

FIG. 37a to 37f show several properties comparison between SPPVN and PPVP. Schematic illustration of the preparation of (FIG. 37a) SPPVN and (FIG. 37b) PPVP; (FIG. 37c) DLS of SPPVN and PPVP in 1×PBS buffer (pH=7.4) Inset: representative TEM images of SPPVN and PPVP. The scale bars represent 100 nm; (FIG. 37d) absorption and (FIG. 37e) fluorescence spectra of SPPVN and PPVP in 1×PBS buffer (pH=7.4). (FIG. 37f) Afterglow luminescence spectra of SPPVN and PPVP under a same mass concentration (130 µg/mL). SPPVN and PPVP solutions were pre-irradiated for 1 min by 514 nm light before the collection of afterglow luminescence signal. The laser power used in the experiments was 1 W/cm$^2$. The error bars represent the standard deviations of three separate measurements.

FIG. 38a to 38f show in vivo tissue-penetration study and lymph node imaging. (FIG. 38a) Fluorescence and afterglow luminescence images of SPPVN solution through a living mouse. The fluorescence image was acquired at 780 nm with excitation at 710 nm. Before the collection of afterglow luminescence images, the SPPVN solution (130 µg/mL, 50

μL) was pre-irradiated at 514 or 808 nm (1 W/cm$^2$) for 1 min. (FIG. 38b) SBRs of fluorescence and afterglow luminescence imaging in FIG. 38a. (FIG. 38c) Fluorescence and afterglow luminescence images of a lymph node in the living mouse at 60 min after intradermal injection of SPPVN (450 μg/mL, 50 μL) into the forepaw of mouse. Afterglow luminescence images were acquired for 30 s after laser irradiation at 808 nm (0.3 W/cm$^2$) for 1 min. (FIG. 38d) SBRs of fluorescence and afterglow luminescence imaging of lymph node in FIG. 38c. (FIG. 38e) Fluorescence and afterglow luminescence images of tumor and skin after local injection of SPPVN (130 μg/mL, 50 μL). (FIG. 38f) Fluorescence and afterglow intensities of tumor and skin after local injection of SPPVN (130 μg/mL, 50 μL). Error bars represent standard deviations of three separate measurements (n=3). n.s.: not significant, **statistically significant difference (p<0.01, n=3).

FIG. 39a to 39e show in vivo tumor imaging. Fluorescence and afterglow luminescence images of living mice at different time points after intravenous injection of (FIG. 39a) SPPVN or (FIG. 39b) PPVP (450 μg/mL, 200 μL). (FIG. 39c) SBRs for fluorescence and afterglow imaging of tumor in living mice treated with SPPVN or PPVP as a function of post-injection time. (FIG. 39d) Ex vivo fluorescence quantification of major organs from mice at 48 h post-injection of SPPVN or PPVP. (FIG. 39e) Ex vivo fluorescence images of major organs of mice at 48 h post-injection of SPPVN or PPVP. The afterglow luminescence images were acquired for 30 s after laser irradiation at 808 nm (0.3 W/cm$^2$) for 1 min. The fluorescence images were acquired at 780 nm with the excitation of 710 nm. Error bars represent standard deviations of three separate measurements (n=3). *Statistically significant difference (p<0.05, n=3).

FIG. 40a to 40e show in vivo peritoneal metastatic tumor imaging. (FIG. 40a) Schematic illustration of establish of metastatic 4T1 tumor model and the imaging procedure. (FIG. 40b) Afterglow luminescence intensities of lower quadrant region for SPPVN or PPVP-injected mice as a function of post-injection time. The injection dosage for SPPVN and PPVP is 450 μg/mL, 200 μL. *Statistically significant difference at t=1.5 h (p<0.01, n=3). (FIG. 40c) Fluorescence and afterglow luminescence images of mice after skin resection to expose the abdominal cavity at 1.5 h post-injection of SPPVN or PPVP. The tumor regions are marked by white circles. (FIG. 40d) Afterglow intensities of background and the tumor regions of SPPVN and PPVP-injected mice marked in figure (c). n.s.: not significant, **Statistically significant difference (p<0.01, n=3). (FIG. 40e) H&E stained slices and confocal images of slices of peritoneal metastatic tumor obtained from SPPVN or PPVP-injected mice. The tumor regions are marked by white frames. Error bars represent standard deviations of three separate measurements (n=3).

FIG. 41a to 41d show biodegradability and clearance studies. (FIG. 41a) Schematic illustration of the degradation of PPV-PEGL in the presence of myeloperoxidase (MPO) and H$_2$O$_2$. (FIG. 41b) Absorption spectra of PPV-PEGL solutions (10 μg/mL) after treatment with MPO (40 μg/mL) and H$_2$O$_2$ (100 μM) for different time. (FIG. 41c) Confocal fluorescence images of macrophages incubated with PPV-PEGL (30 μg/mL) and stimulated with LPS for different time. The macrophages were co-stained with Hoechst 33342. (FIG. 41d) Quantification of fluorescence intensities of liver in living mice injected with SPPVN (450 μg/mL, 200 μL) as a function of time. The fluorescence signals were acquired at 780 nm with the excitation of 710 nm. Error bars represent standard deviation of three separate measurements (n=3).

FIG. 42a to 42f show mechanistic study of the afterglow of PPV-PEG1. (FIG. 42a) Representative DLS of PPVPEG1. Inset: representative TEM image of PPV-PEG1, the scale bar represents 50 nm. (FIG. 42b) Schematic illustration of fluorescence and afterglow luminescence of PPV-PEG1. (FIG. 42c) Normalized absorption, fluorescence and afterglow luminescence spectra of PPV-PEG1 in 1×PBS buffer (pH=7.4). (FIG. 42d) Fluorescence enhancement (F/F$_0$) of SOSG (1 μM) in the absence or presence of PPV-PEG1 (0.6 μg/mL) at 528 nm as a function of 514 nm light irradiation time. (FIG. 42e) Afterglow luminescence intensities and images of PPV-PEG1 (40 μg/mL) acquired at room temperature, after purging by O$_2$ or in the presence of NaN$_3$ (50 w/w %). **Statistically significant difference (P<0.01, n=3, statistical significance calculated relative to control). (FIG. 42f) Proposed mechanism for the afterglow luminescence of PPV-PEG1. The error bars represent the standard deviations of three separate measurements.

FIG. 43a to 43f show (FIG. 43a) $^1$H NMR spectra of PPV-Br1 before and after 514 nm light irradiation for 12 h in CDCl$_3$. (FIG. 43b) FTIR spectra of PPV-Br1 before and after 514 nm light irradiation for 12 h in THF. Absorption (FIG. 43c) and fluorescence (FIG. 43d) spectra of PPV-Br1 (12 μg/mL) before and after 514 nm light irradiation for 12 h in THF. Absorption (FIG. 43e) and fluorescence (FIG. 43f) spectra of PPV-PEG1 (12 μg/mL) before and after 514 nm light irradiation for 12 h in water.

FIG. 44a to 44c show (FIG. 44a) absorption of PPV-PEG1 at various doping amounts (w/w %) of NCBS in 1×PBS (pH=7.4); (FIG. 44b) fluorescence spectra of PPV-PEG1 at various doping amount of NCBS in 1×PBS (pH=7.4) and (FIG. 44c) DLS of PPV-PEG1 at various doping amount of NCBS in 1×PBS (pH=7.4). The error bars represent the standard deviation of three separate measurements.

FIG. 45a to 45f show effect of doping photosensitizer on the physical and optical properties of nanoparticles. (FIG. 45a) DLS of NCBS doped PPV-PEGL with different doping amount of NCBS in 1×PBS buffer (pH=7.4). Absorption (FIG. 45b), fluorescence (FIG. 45c) and afterglow luminescence (FIG. 45d) spectra of NCBS doped PPV-PEGL with different doping amount of NCBS in 1×PBS buffer (pH=7.4). (FIG. 45e) Quantification of the absolute fluorescence and afterglow luminescence intensities of NCBS doped PPV-PEGL (70 μg/mL) with different doping amount of NCBS. (FIG. 45f) Decay of afterglow luminescence of NCBS doped PPV-PEGL (130 μg/mL) at room temperature. SPPVN solution was pre-irradiated for 1 min by 514 nm light before the collection of afterglow luminescence signal. The light power used in the experiments was 1 W/cm$^2$. The error bars represent the standard deviations of three separate measurements.

FIG. 46a to 46d show photosensitizer amplified NIR afterglow. (FIG. 46a) Afterglow luminescence images of NCBS doped PPV-PEGL (130 μg/mL) pre-irradiated by 514 or 808 nm. (FIG. 46b) Ratio of afterglow luminescence intensities of NCBS doped PPV-PEGL pre-irradiated by 808 nm to 514 nm ($I_{808}/I_{514}$) with different doping amount of NCBS. (FIG. 46c) Fluorescence enhancement (F/F$_0$) of SOSG at 528 nm in the presence of SPPVN as a function of irradiation time by 808 or 514 nm laser. (FIG. 46d) Schematic illustration of the proposed mechanism for afterglow luminescence of NCBS doped PPV-PEGL pre-irradiated by 514 or 808 nm laser. The laser power used in the experiments is 1 W/cm$^2$.

FIG. 47a to 47c show (FIG. 47a) Average diameter of SPPVT and SPPVN in 1×PBS (pH=7.4); (FIG. 47b) absorption, (FIG. 47c) fluorescence and (FIG. 47d) afterglow luminescence spectra of SPPVT (200 μg/mL) with 0 and 2% (w/w %) doping amount of TPP. The error bars represent the standard deviation of three separate measurements.

Figure 48:
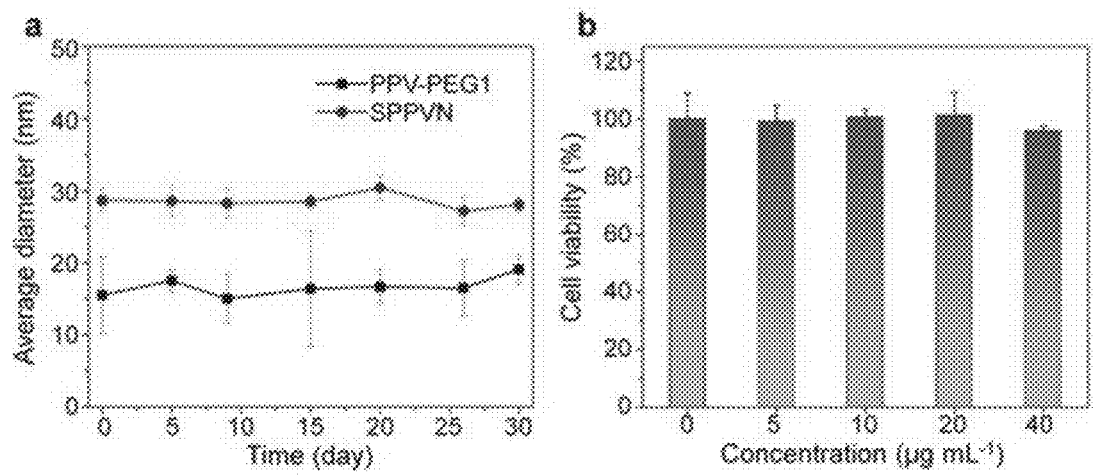

FIGS. 48a and 48b show (FIG. 48a) DLS of PPV-PEG1 and SPPVN as a function of time incubated with 1×PBS (pH=7.4). (FIG. 48b) Cell viability of Hela cells after incubation with SPPVN in various concentrations. The error bars represent the standard deviation of three separate measurements.

Figure 49:
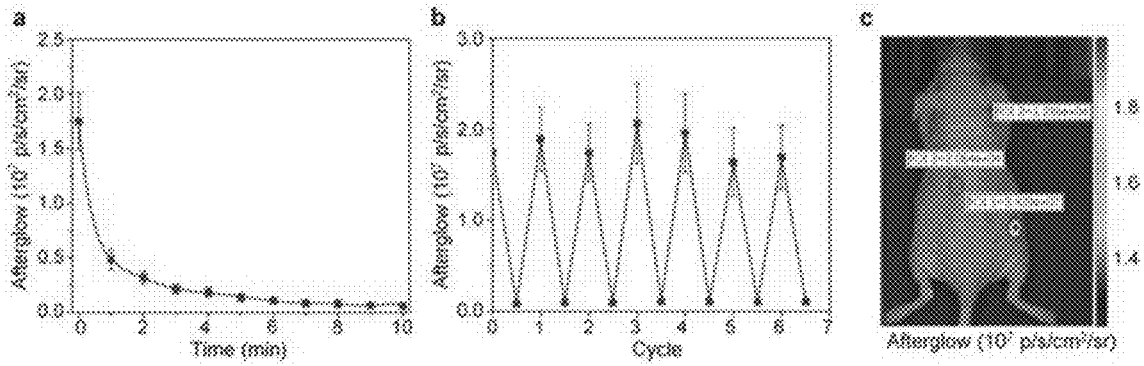

FIG. 49a to 49c show (FIG. 49a) In vivo afterglow decay of SPPVN (130 μg/mL, 50 μL) recorded after light irradiation for 1 min by 808 nm laser; (FIG. 49b) Afterglow luminescence intensities of the subcutaneous injection of SPPVN (130 μg/mL, 50 μL) as a function of cycle number of light irradiation. The laser power used in the experiments was 0.3 W/cm$^2$ and (FIG. 49c) Calculation of SBR from the in vivo afterglow luminescence image of a mouse with subcutaneous inclusion of SPPVN (130 μg/mL, 50 μL). Error bars represent standard deviations of three separate measurements (n=3).

FIG. 50a to 50c show In vivo imaging of tumor with the size of 1 mm$^3$. (FIG. 50a) Fluorescence and afterglow luminescence images of tumor in living mice at different time points after intravenous injection of SPPVN (450 μg/mL, 200 μL). (FIG. 50b) SBRs for fluorescence and afterglow luminescence imaging of tumor in living mice as a function of post-injection time. (FIG. 50c) Ex vivo quantification of fluorescence of major organs from mice 48 h after intravenous injection of SPPVN. Error bars represent standard deviations of three separate measurements (n=3). The afterglow luminescence images were acquired for 30 s after irradiation under 808 nm laser (0.3 W/cm$^2$) for 1 min. The fluorescence images were acquired at 780 nm with the excitation of 710 nm.

FIGS. 51a and 51b show (FIG. 51a) Fluorescence and (FIG. 51b) afterglow intensities of liver for 5 and 1 mm$^3$ tumor-bearing mice treated with SPPVN (450 μg/mL, 200 μL) as a function of post-injection time.

Figure 52:
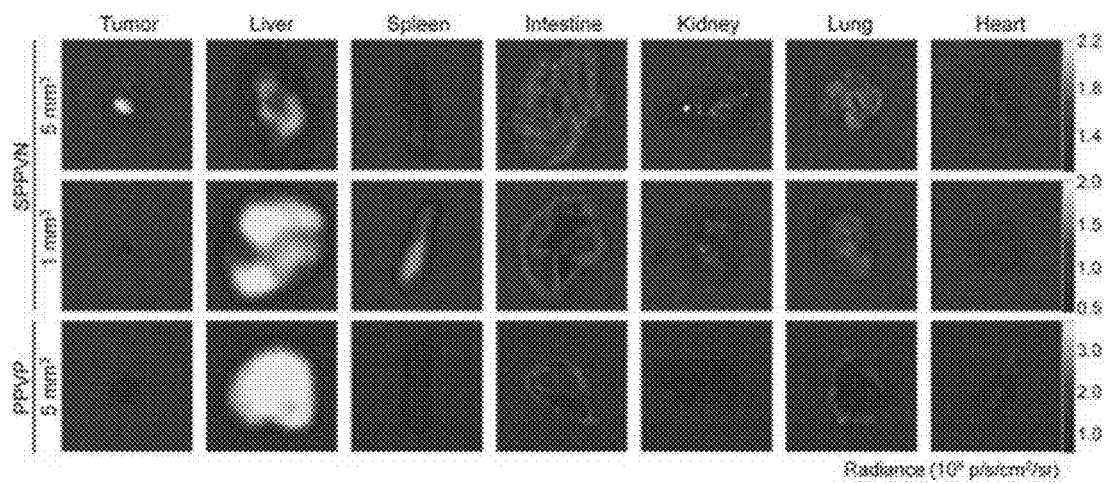

FIG. 52 show ex vivo fluorescence images of major organs of mice with 5 or 1 mm$^3$ tumor 48 h after systemic administration of SPPVN or PPVP.

Figure 53:
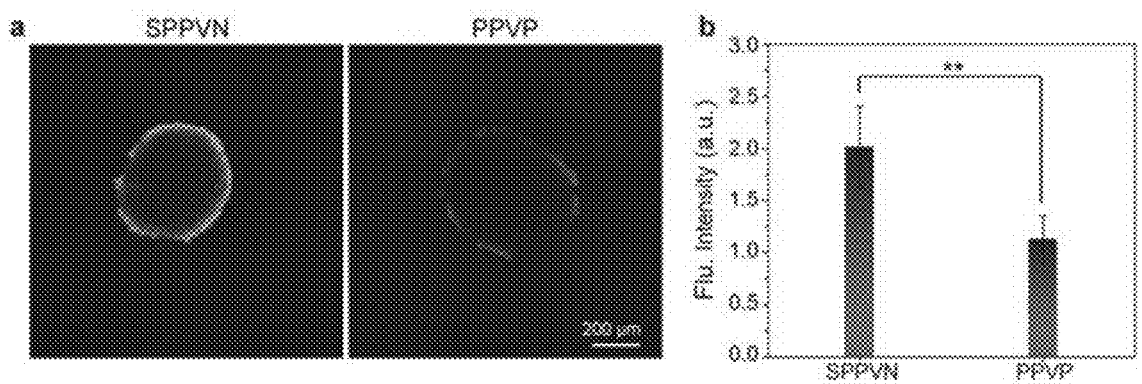

FIGS. 53a and 53b show (FIG. 53a) Confocal fluorescence images of multicellular tumor spheroids (MCTS) incubated with SPPVN or PPVP for 12 h. The fluorescence of SPPVN and PPVP was adjusted to the same before incubation. (FIG. 53b) Quantification of the fluorescence intensities of SPPVN and PPVP incubated multicellular tumor spheroids. **Statistically significant difference (p<0.01, n=3).

Figure 54:
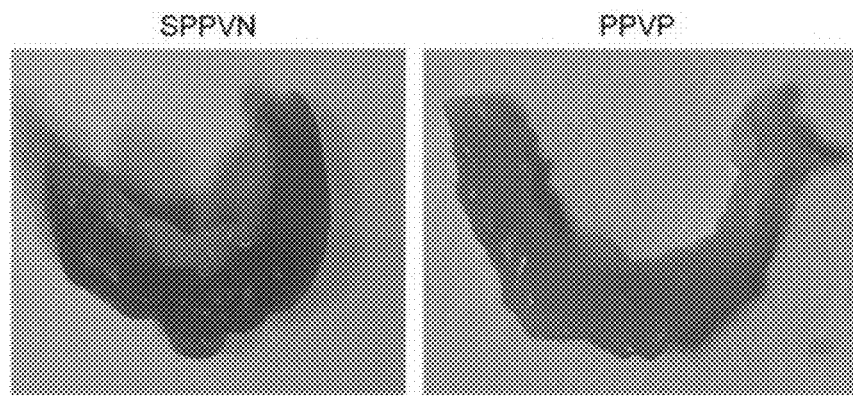

FIG. 54 shows the intestines resected from SPPVN or PPVP-injected peritoneal metastatic tumor-bearing mice for the H&E staining and confocal imaging.

Figure 55:
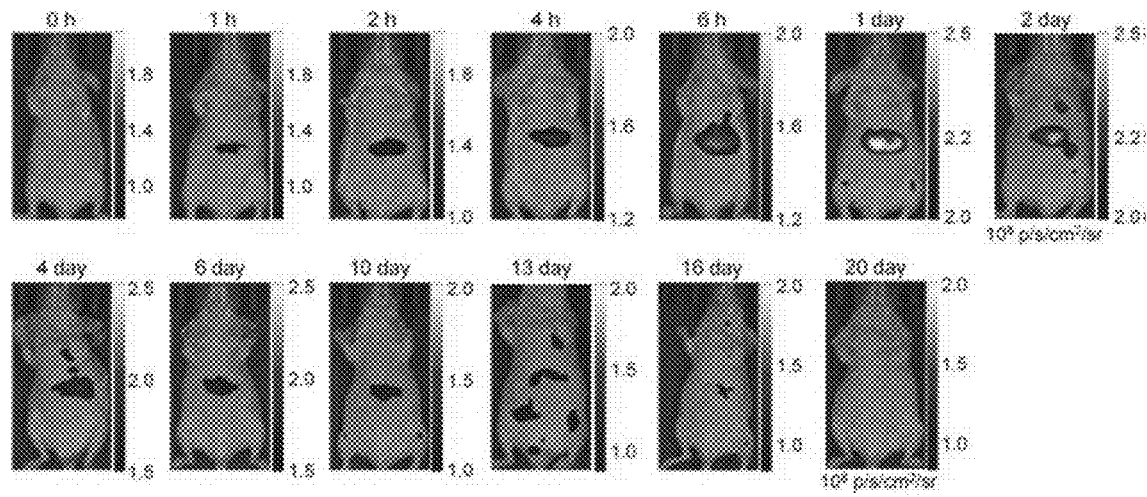

FIG. 55 shows the fluorescence images of living mice at different time points after systemic administration of SPPVN (450 μg/mL, 200 μL).

FIG. 56a to 56e show synthesis and characterization of SPN-PPV-TPPs. (FIG. 56a) Synthesis route of PPV, PPV-TPP$_{2.5\%}$ and PPV-TPP$_{5\%}$. Reagents and conditions: i) Tris (dibenzylideneacetone)dipalladium(0) [Pd2(dba)3], Tri(p-tolyl)phosphine (TP), Chlorobenzene, 100° C., 24 h. (FIG. 56b) Schematic illustration of the preparation of SPN-PPV-TPPs. (FIG. 56c) DLS of SPN2.5 in 1×PBS buffer (pH=7.4). (FIG. 56d) TEM images of SPN2.5. The scale bar represents 100 nm. (FIG. 56e) Cell viability of 4T1 cells after incubation with SPN2.5 solutions at various concentrations.

FIG. 57a to 57f show optical characterization of SPN-PPV-TPPs. (FIG. 57a) Normalized UV-visible absorption spectra of SPN-PPV-TPPs. (FIG. 57b) Fluorescence spectra of SPN-PPV-TPPs. The concentration of PPV component of both SPs were 30 μg/mL in 1×PBS (pH=7.4). (FIG. 57c) Afterglow luminescence spectra of SPN-PPV-TPPs (100 μg/mL). SPN-PPV-TPP solutions were pre-irradiated for 1 min by white light before the collection of afterglow luminescence signal. The error bars represent the standard deviations of three separate measurements. (FIG. 57d) Fluorescence images (up) and afterglow luminescence images (bottom) of SPN-PPV-TPPs in 1×PBS (pH=7.4). The fluorescence images were acquired upon excitation at 430 nm with the emission at 720 nm. The afterglow images were acquired for 30 s after the pre-irradiation of SPN-PPV-TPPs under white light at a power density of 1 W/cm$^2$ for 1 min. (FIG. 57e) Quantification of fluorescence and afterglow intensities of SPN-PPV-TPPs. The error bars represent the standard deviations of three separate measurements. (FIG. 57f) Normalized decay of afterglow luminescence of SPN-PPV-TPPs (100 μg/mL) at room temperature. SPN-PPV-TPP solutions were pre-irradiated for 1 min by white light before the collection of afterglow luminescence signal. The light power used in the experiments was 1 W/cm$^2$.

Figure 58:
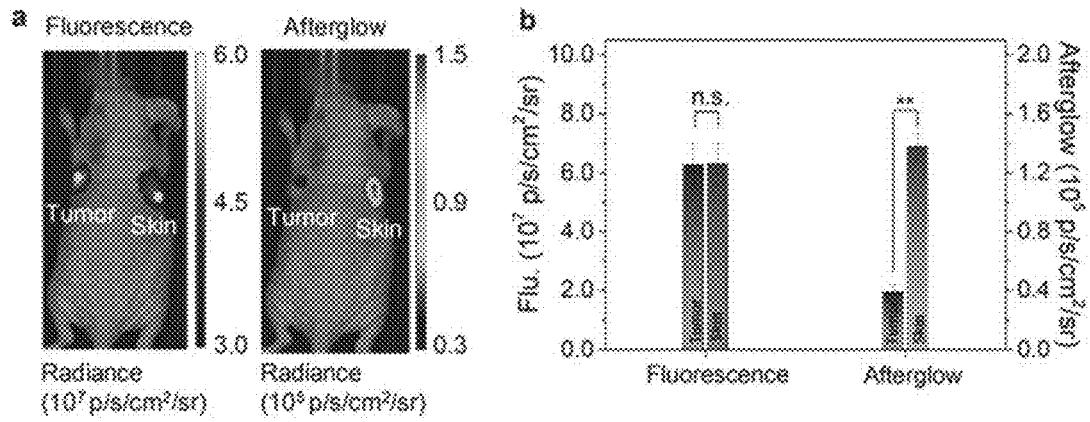

FIGS. 58a and 58b show in vivo imaging of tumor hypoxia. (FIG. 58a) Fluorescence and afterglow luminescence images of tumor and skin after local injection of SPN2.5 (100 μg/mL, 50 μL). (FIG. 58b) Fluorescence and afterglow intensities of tumor and skin after local injection of SPPVN (130 μg/mL, 50 μL). Error bars represent standard deviations of three separate measurements (n=3). n.s.: not significant, *statistically significant difference (p<0.01, n=3).

FIG. 59a to 59d show in vivo peritoneal metastatic tumor imaging. (FIG. 59a) Fluorescence and afterglow luminescence images of peritoneal metastatic tumor in living mice at different time points after intravenous injection of SPN2.5 (400 μg/mL, 200 μL). The liver site is marked by black circle. The tumor site is marked by white frame. (FIG. 59b) Fluorescence and afterglow luminescence images of mice with skin removed to expose the abdominal cavity at 4 h post-injection of SPN2.5. The tumor regions are marked by white circles. (FIG. 59c) Afterglow luminescence intensities of white frame region for SPN2.5 (400 μg/mL, 200 μL)-injected mice as a function of post-injection time in FIG. 4a. Error bars represent standard deviations of three separate measurements (n=3). (FIG. 59d) H&E stained slices of peritoneal metastatic tumor obtained from SPN2.5-injected mice. The tumor regions are marked by the dotted black lines.

Figure 60:
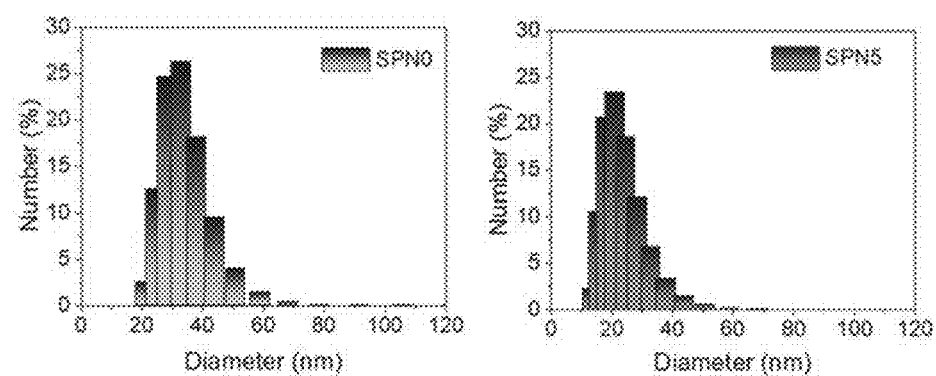

FIG. 60 show DLS data of SPN0 and SPN5 incubated with PBS (pH=7.4). The PDI of SPN0 is 0.31. The PDI of SPN5 is 0.346.

Figure 61:
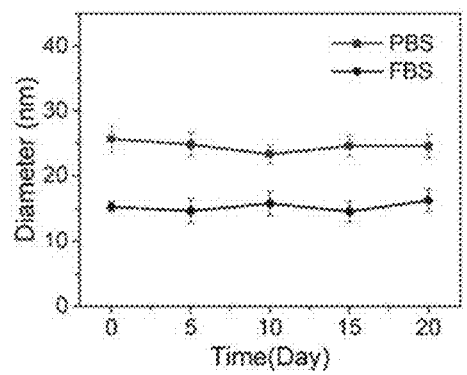

FIG. 61 show DLS data of SPN2.5 as a function of time incubated with PBS (pH=7.4) and FBS.

Figure 62:
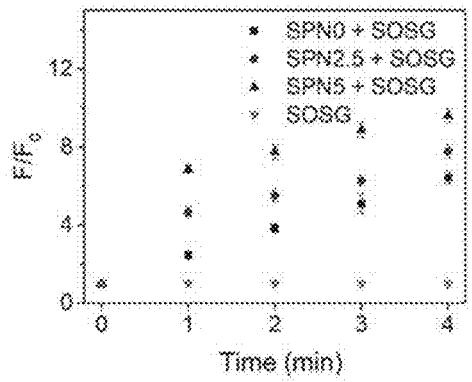

FIG. 62 show fluorescence enhancement ($F/F_0$) of SOSG (1 μM) in the absence or presence of SPN0, SPN2.5 and SPN5 (0.8 μg/mL) at 528 nm as a function of white light irradiation time.

Figure 63:
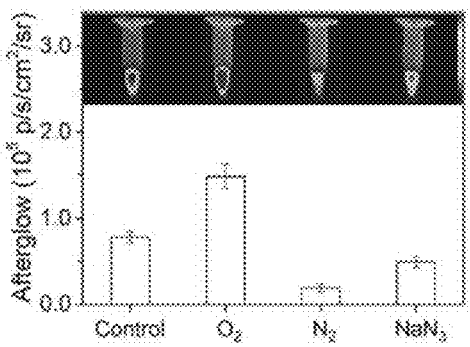

FIG. 63 show afterglow luminescence intensities and images of SPN2.5 (50 μg/mL) acquired at room temperature, after purging by $O_2$, $N_2$ or in the presence of $NaN_3$ (50 w/w %).

DESCRIPTION

We disclose herein the production and application of semiconducting polymer nanoparticles (SPNs) as afterglow luminescence probes for molecular imaging in living mice.

The SPNs disclosed herein are built from optically-active semiconducting polymers (SPs) and are an alternative class of photonic nanomaterials. They are completely organic and contain biologically benign ingredients to overcome metal-ion-induced toxicity. The irradiation of the PPV-based SPNs forms unstable chemical defects (dioxetane units) that can spontaneously and slowly break down to release photons that result in afterglow luminescence. Although the mechanism that governs the afterglow luminescence of PPV-based SPNs resembles chemiluminescence, it does not require exogenous ROS to trigger the reaction. Rather, the SPNs themselves can generate singlet oxygen ($^1O_2$) under light irradiation and subsequently induce afterglow luminescence. Such an afterglow mechanism also differs from that of rare-earth-doped inorganic nanoparticles wherein the absorbed photon energy is stored in intrinsic defect lattices rather than light-induced chemical defects.

Thus, disclosed herein is a polymeric composite nanoparticle that emits near-infrared afterglow luminescence, the nanoparticle comprising:

(a) a semiconducting polymer of formula I:

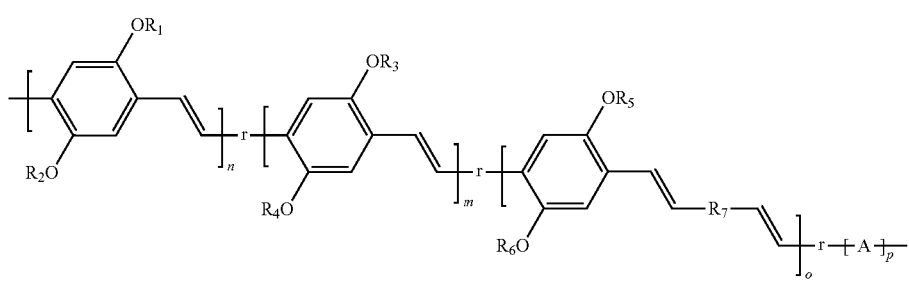

(b) optionally, an amphiphilic copolymer; and (c) optionally, a small molecular dye with near-infrared emission, wherein:

when present, the amphiphilic copolymer encapsulates the semiconducting polymer of formula I and, when present, the small molecular dye; and in the polymer of formula I:

$R_1$ to $R_3$ and $R_5$ independently represent an alkyl chain of the formula $C_qH_{2q+1}$, where $1 \leq q \leq 50$, $R_4$ represents a moiety of formula Ia or formula Ib:

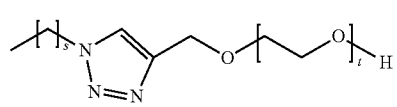

where $1 \leq s \leq 50$ and $10 \leq t \leq 500$;

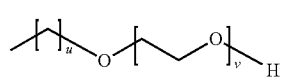

where $1 \leq u \leq 50$ and $10 \leq v \leq 500$:

$R_6$ represents an alkyl chain of the formula $C_qH_{2q+1}$, a moiety of formula Ia or a moiety of formula Ib where q, s, t, u and v are as defined above;

$R_7$ represents a singlet oxygen sensitizing moiety;

each of n, m and o are each greater than or equal to 0 and p is 0 or 1, where at least one of n, m, o and p are greater than 0;

A represents a moiety of formula Ic or Id:

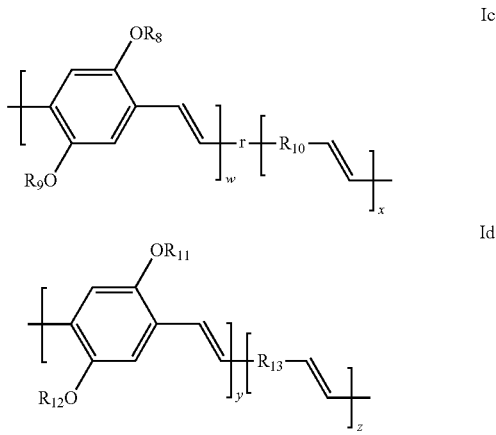

where $R_8$ and $R_{11}$ independently represent an alkyl chain of the formula $C_qH_{2q+1}$, where: $1 \leq q \leq 50$;

$R_9$ and $R_{12}$ independently represent an alkyl chain of the formula $C_qH_{2q+1}$, a moiety of formula Ia or a moiety of formula Ib, where q, s, t, u and v are as defined above;

$R_{10}$ and $R_{13}$ independently represent a singlet oxygen sensitizing moiety;

when p is 1, then w, x, y and z, when present, are independently greater than or equal to 0; and the small molecular dye is present when o and p are 0 and is optionally present when:

o is greater than or equal to 20;

p is 1 and x or z is greater than or equal to 20;

the sum of o and x is greater than or equal to 20;

the sum of o and z is greater than or equal to 20;

$(o+x)/(n+m+o+w+x) > 0.05$; or $(o+z)/(n+m+o+y+z) > 0.05$;

the amphiphilic copolymer is present when m, o and p are 0 and optionally present when:

$(m+o+w)/(n+m+o+w+x) > 0.1$; or $(m+o+y)/(n+m+o+y+z) > 0.1$; and provided that when n is greater than 0, one or more of m, o and p are also greater than 0.

As will be appreciated, the above composite nanoparticle covers situations where:
(aa) all three components (a), (b) and (c) are present;
(ab) only components (a) and (b) are present;
(ac) only components (a) and (c) are present; and
(ad) only component (a) is present.

In situations where all three components (a), (b) and (c) are present, the amphiphilic copolymer (component (b)) encapsulates the semiconducting polymer of formula I (component (a)) and the small molecular dye (component (c)). When used herein, the term "encapsulates" means that the other materials are wholly trapped within the polymeric matrix of the encapsulating material.

In situations where only components (a) and (b) are present, the amphiphilic copolymer (component (b)) encapsulates the semiconducting polymer of formula I (component (a)). As noted above, the small molecular dye may not be needed when: $(o+x)/(n+m+o+w+x) > 0.05$; or $(o+z)/(n+m+o+y+z) > 0.05$ or, more particularly, p is 1 and x or z is greater than or equal to 20 or, yet more particularly, o is greater than or equal to 20; the sum of o and x is greater than or equal to 20; or the sum of o and z is greater than or equal to 20. As will be appreciated, in the above-mentioned conditions, the reason that the small molecular dye may be excluded is because the semiconducting polymer of formula I incorporates an equivalent group (i.e. a singlet oxygen sensitizing moiety) that provides the same functionality. Thus, in certain embodiments, when any of the preceding conditions are met, then the small molecular dye is not present.

In situations where only components (a) and (c) are present, the semiconducting polymer of formula I (component (a)) encapsulates the small molecular dye (component (c)). As noted above, the amphiphilic copolymer may not be needed when: $(m+o+w)/(n+m+o+w+x) > 0.1$ or $(m+o+y)/(n+m+o+y+z) > 0.1$. In additional embodiments, the amphiphilic copolymer may not be needed when:
m is greater than or equal to 20 and $m/(n+m+o)$ is greater than 0.1 and $R^6$ is $C_qH_{2q+1}$, where $1 \leq q \leq 50$;
m is greater than or equal to 20 and $(m+o)/(x+y+z)$ is greater than 0.1 and $R^6$ is a moiety of formula Ia or a moiety of formula Ib; or
o is greater than or equal to 20 and $(m+o)/(x+y+z)$ is greater than 0.1 and $R^6$ is a moiety of formula Ia or a moiety of formula Ib. In certain embodiments, when any of the preceding conditions are met, then the amphiphilic copolymer is not present.

It will be appreciated that the above conditions as to the absence of components (b) and (c) also apply to the situation where only (a) is present. That is when any technically combination of the conditions set out above are met for the absence of the amphiphilic copolymer and the small molecular dye may result in the absence of both of these components.

Preferred embodiments of the current invention include those listed as (ac), more particularly, (ab) and, yet more particularly, (aa) above. In other words, preferred embodiments are those in which the amphiphilic copolymer is present.

Given the above, it will also be appreciated that the invention also relates to a semiconducting polymer of formula I:

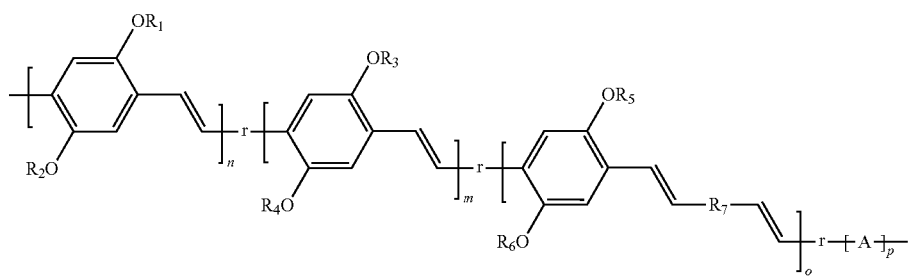

in the polymer of formula I:
$R_1$ to $R_3$ and $R_5$ independently represent an alkyl chain of the formula $C_qH_{2q+1}$, where $1 \leq q \leq 50$,
$R_4$ represents a moiety of formula Ia or formula Ib:
where $1 \leq s \leq 50$ and $10 \leq t \leq 500$;

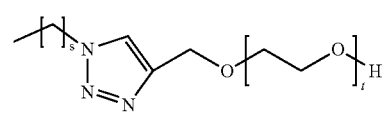

where $1 \leq u \leq 50$ and $10 \leq v \leq 500$;
$R_6$ represents an alkyl chain of the formula $C_qH_{2q+1}$, a moiety of formula Ia or a moiety of formula Ib, where

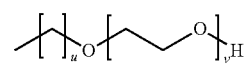

q, s, t, u and v are as defined above;
$R_7$ represents a singlet oxygen sensitizing moiety;
each of n, m and o are each greater than or equal to 0;
p is 0 or 1;
A represents a moiety of formula Ic or Id:

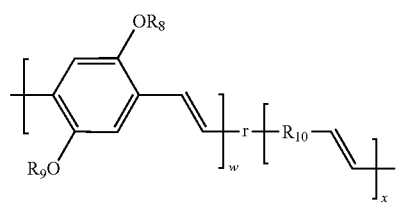

-continued

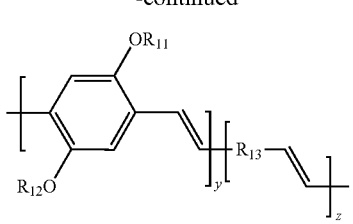

Id where $R_8$ and $R_{11}$ independently represent an alkyl chain of the formula $C_qH_{2q+1}$, where: $1 \leq q \leq 50$;

$R_9$ and $R_{12}$ independently represent an alkyl chain of the formula $C_qH_{2q+1}$, a moiety of formula Ia or a moiety of formula Ib, where q, s, t, u and v are as defined above;

$R_{10}$ and $R_{11}$ independently represent a singlet oxygen sensitizing moiety;

when p is 1, then w, x, y and z, when present, are independently greater than or equal to 0;

provided that:

when n is greater than 0, one or more of m, o and p are also greater than 0; and at least one of n, m, o and p are greater than 0.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

Unless otherwise explicitly stated, reference to embodiments of the semiconducting polymer of formula I may equally refer to the polymer per se or to the polymer as part of a composite material comprising one or more of amphiphilic copolymer and a small molecular dye with near-infrared emission.

Unless otherwise stated, the term "alkyl" refers to a saturated unbranched or branched, acyclic hydrocarbyl radical. The alkyl group may be any $C_{1-50}$ alkyl group and, more preferably, $C_{1-10}$ alkyl (such as ethyl, propyl, (e.g. n-propyl or isopropyl), pentyl or, more particularly, butyl (e.g. branched or unbranched butyl), octyl (e.g. unbranched or, more particularly, branched octyl (e.g. 2-ethylhexyl)) or methyl).

When used herein, the term "r" is used to refer to indicate that the semiconducting polymer of formula I is a random copolymer when two or more of n, m, o and p are greater than 0.

In certain embodiments of the invention, n and/or p may be 0.

In certain embodiments of the invention, when one or more of n, m, o and p are non-zero, then each of n, m, o, w, x, y and z may independently have a value of from 5 to 1000, such as from 10 to 750, such as from 15 to 500, such as from 20 to 250, such as from 50 to 100. When a list of ranges is provided herein, any technically sensible combination of the end values provided may be used to provide a further range. For example, in the above-mentioned list, further ranges that are explicitly included include:

5 to 10, 5 to 15, 5 to 20, 5 to 50, 5 to 100, 5 to 250, 5 to 500 and 5 to 750;

10 to 15, 10 to 20, 10 to 50, 10 to 100, 10 to 250, 10 to 500 and 10 to 1000;

15 to 20, 15 to 50, 15 to 100, 15 to 250, 15 to 750 and 5 to 1000;

20 to 50, 20 to 100, 20 to 500, 20 to 750 and 20 to 1000;

50 to 250, 50 to 500, 50 to 750, and 50 to 1000;

100 to 250, 100 to 500, 100 to 750 and 100 to 1000;

250 to 500, 250 to 750 and 250 to 1000;

500 to 750 and 500 to 1000; and 750 to 1000.

It will be appreciated that the same type of combinations for other listed ranges are explicitly contemplated.

In embodiments of the invention, the number average molecular weight of the polymer of formula I may be from 1,000 to 300,000 Daltons, such as from 1,000 to 100,000 Daltons, such as from 1,500 to 50,000 Daltons, such as from 25,000 to 75,000 Daltons.

When used herein, the term "singlet oxygen sensitizing moiety" refers to any suitable organic or organometallic moiety that is capable of causing oxygen in its triplet state to be converted to one of its singlet states and which can be incorporated into an organic polymer of the type disclosed herein. More particularly, the singlet oxygen sensitizing moiety may be a photosensitising moiety. Suitable photosensitizing compounds, which may be incorporated into the polymer of formula I as a singlet oxygen sensitizing moiety are disclosed in DeRosa, M. C. and Crutchley, R. J. *Photosensitized singlet oxygen and its applications, Coordination Chemistry Reviews* 233/234 (2002) 351/371, particularly on pages 354 to 359 of said review article, which are incorporated herein by reference. More particularly, the singlet oxygen sensitizing moiety of $R_7$, $R_{10}$ and $R_{13}$ may be independently selected from one or more of the group consisting of metallo-porphyrins, metallo-phthalocyanines, naphthalocyanines, metallo-naphthalocyanines, chlorins, rhodamine, cyanine, carotenoid, anthocyanin, rose bengal, methylene blue and, more particularly, silicon 2,3-naphthalocyanine bis(trihexylsilyloxide), porphyrins (octaethylporphine, tetraphenyl porphyrin), phthalocyanines, tetrapyrroles, transition metal complexes (Ir(III) complexes, Ru(II) complexes, Pt(II) complexes and Os(II) complexes) and boron-dipyrromethene (BODIPY)-based photosensitizers (e.g. the group may consist of one or more of silicon 2,3-naphthalocyanine bis(trihexylsilyloxide), porphyrins (octaethylporphine, tetraphenyl porphyrin), phthalocyanines, tetrapyrroles, transition metal complexes (Ir(III) complexes, Ru(II) complexes, Pt(II) complexes and Os(II) complexes) and boron-dipyrromethene (BODIPY)-based photosensitizers).

Similarly, when used herein the term "small molecular dye with near-infrared emission" refers to any suitable organic or organometallic molecule that is capable of causing oxygen in its triplet state to be converted to one of its singlet states as a separate entity from the semiconducting polymer of formula I. More particularly, the small molecular dye with near-infrared emission may be a photosensitising moiety. Suitable photosensitizing compounds are disclosed in DeRosa, M. C. and Crutchley, R. J. *Photosensitized singlet oxygen and its applications, Coordination Chemistry Reviews* 233/234 (2002) 351/371, particularly on pages 354 to 359 of said review article, which are incorporated herein by reference. More particularly, the small molecular dye with near-infrared emission may be selected from one or more of the group consisting of metallo-porphyrins, metallo-phthalocyanines, naphthalocyanines, metallo-naphthalocyanines, chlorins, rhodamine, cyanine, carotenoid, anthocyanin, rose bengal, methylene blue and, more particularly, silicon 2,3-naphthalocyanine bis(trihexylsilyloxide), porphyrins (octaethylporphine, tetraphenyl porphyrin), phthalocyanines, tetrapyrroles, transition metal complexes (Ir(III) complexes, Ru(II) complexes, Pt(II) complexes and Os(II) complexes) and boron-dipyrromethene (BODIPY)-based photosensitizers (e.g. the group may consist of one or more of silicon 2,3-naphthalocyanine bis(trihexylsilyloxide), porphyrins (octaethylporphine, tetraphenyl porphyrin), phthalocyanines, tetrapyrroles, transition metal complexes (Ir(III) complexes, Ru(II) complexes, Pt(II) complexes and Os(II) complexes) and boron-dipyrromethene (BODIPY)-based photosensitizers).

In embodiments of the current invention, the polymer of formula I may be selected from the list of:

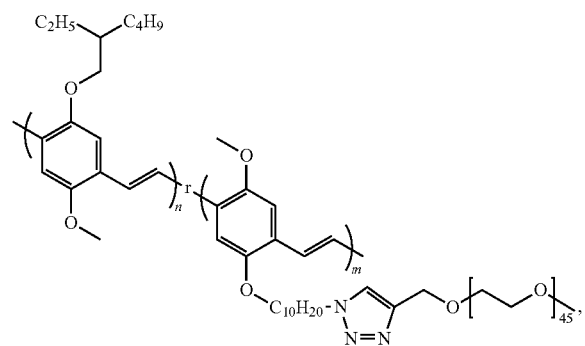

(i)

where n and m are as defined in any one of the preceding claims, optionally wherein the number of n and m repeating units provides a polymer having a number average molecular weight of from 25,000 to 200,000 Daltons, such as from 45,000 to 150,000 Daltons, such from 50,000 to 100,000 Daltons, such as around 59,781 Daltons and/or the molar ratio of n repeating units in the polymer is around 88% and the molar ratio of m repeating units in the polymer is around 11% (e.g. the molar ratio of n repeating units in the polymer is from 88.0 to 89.0% and the molar ratio of m repeating units in the polymer is from 11.0 to 12.0%);

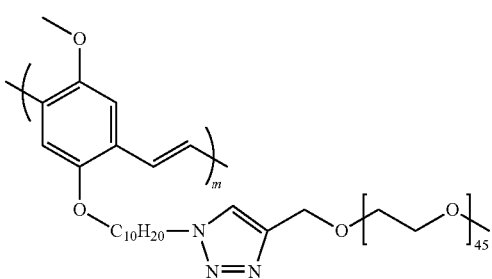

(ii)

where m is as defined in any one of the preceding claims, optionally wherein the number of m repeating units provides a polymer having a number average molecular weight of from 15,000 to 100,000 Daltons, such as from 20,000 to 75,000 Daltons, such as from 20,000 to 50,000 Daltons, such as around 26,565 Daltons;

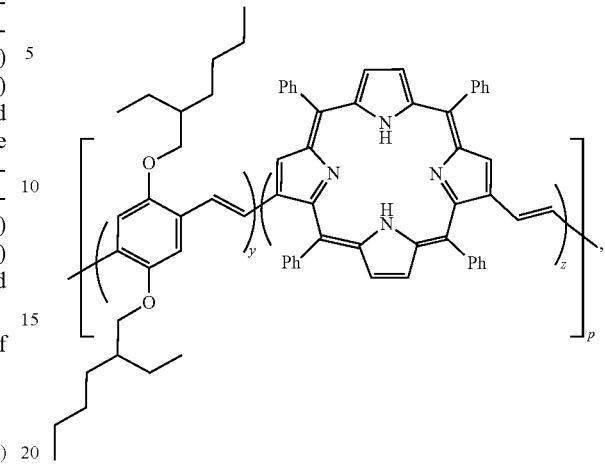

(iii)

where p is 1 and the number of y and z repeating units provide a polymer having a number average molecular weight of from 5,000 to 20,000 Daltons, such as from 7,000 to 18,000 Daltons, such from 8,900 to 15,000 Daltons, such as around 13,000 Daltons and/or the molar ratio of y repeating units in the polymer is from 85 to 99% and the molar ratio of z repeating units in the polymer is from 1 to 15% (e.g. the molar ratio of y repeating units in the polymer is from 90.0 to 95.0% and the molar ratio of z repeating units in the polymer is from 5.0 to 10.0%).

When used herein, the term "amphiphilic copolymer" refers to a polymeric material containing at least two monomeric units (providing a random or, more particularly, block copolymer), where the resulting polymer has one or more portions that are hydrophobic in nature and one or more portions that are hydrophilic in nature. Examples of suitable amphiphilic copolymers includes, but is not limited to one or more of the group comprising alky-substituted chitosan, and more particularly poly(alkyl)-b-poly(ethylene glycol), poly(ethylene glycol)-b-poly(propylene glycol)-b-poly(ethylene glycol), poly(ethylene glycol) methyl ether-block-poly(lactide-co-glycolide) (PEG-PLGA), poly(styrene)-block-poly(acrylic acid) (PS-PAA), poly(styrene-co-maleic anhydride) (PSMA), 1,2-dipalmitoyl-sn-glycero-3-phosphocholine (DPPC) and 1,2-distearoyl-sn-glycero-3-phosphoethanolamine-poly(ethylene glycol) (DSPE-PEG). Any suitable molecular weight of the amphiphilic copolymer may be used. For example, the amphiphilic copolymer may have a number average molecular weight of from 1,000 to 50,000 Daltons, such as from 1,500 to 40,000 Daltons, such as from 5,000 to 25,000 Daltons, such as from 4,000 to 20,000 Daltons.

In certain embodiments of the invention, the amphiphilic copolymer may further comprise a quenching moiety that is cleavable by a reactive moiety in an in vitro or in vivo test site. When used herein, the term "quenching moiety" is intended to refer to any moiety capable of absorbing excitation energy and re-emitting it as another form of energy that is not light. Examples of suitable quenching moieties include dark quenchers, which include, but are not limited to dabsyl (dimethylaminoazobenzenesulfonic acid), black hole quenchers, QxI quenchers, Iowa black RQ, Iowa black RQ, IRDye QC-1, and a 2,4-dinitrophenylsulfonyl moiety. Suitable dark quenchers include Black Hole Quencher (BHQ)-1, BHQ-2, BHQ-3, and QSY-7, as well as 2,4-dinitrophenylsulfonyl (DNBS) moiety.

As noted above, the quenching moiety is attached to the amphiphilic copolymer in such a way that it can be removed upon exposure to a reactive moiety under certain conditions that may be found at the site of testing/imaging. In other words, the quenching moiety comprises both a quenching group and a linking group that incorporates a reactive group that can be cleaved under certain conditions. Examples of suitable quenching moieties (incorporating linkers), includes, but is not limited to a thiol-sensitive, such as 2,4-dinitrophenylsulfonyl (DNBS) moiety, and

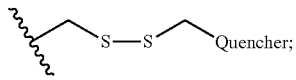

a reactive oxygen species-sensitive moiety

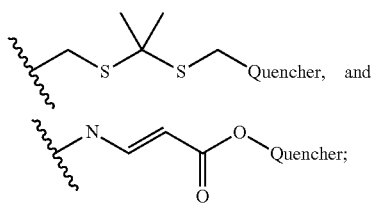

a pH-sensitive moiety such as

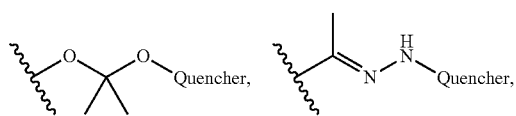

-continued

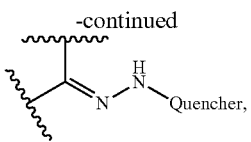

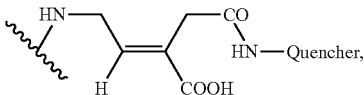

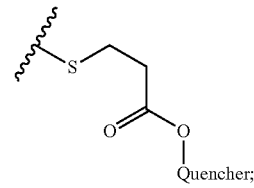

a peptide-quencher moiety, such as a furin-sensitive Arg-Arg-Val-Arg-Quencher, Caspase-3-sensitive Asp-Val-Glu-Asp-Quencher, a fibroblast activation protein-alpha (FAPα)-sensitive Gly-Pro-Quencher, a matrix metalloproteinase-2 (MMP-2)-sensitive Gly-Arg-Val-Gly-Leu-Pro-Quencher, a MMP-7-sensitive Gly-Met-Trp-Ser-Leu-Pro-Val-Quencher, a MMP-13-sensitive Leu-Gly-Arg-Met-Gly-Leu-Pro-Quencher, a Cathepsin B-sensitive Lys-lys-Quencher, a Cathepsin D-sensitive Leu-Arg-Phe-Phe-Cys-Ile-Pro-Quencher, a Cathepsin S-sensitive Arg-Leu-Quencher, a Urokinase-sensitive Arg-Gly-Quencher and a Legumain-sensitive Asn-Ala-Ala-Quencher, where the Quencher is a Dark Quencher (e.g. as defined above).

In particular embodiments of the invention where the amphiphilic copolymer further comprises a quenching moiety, the amphiphilic copolymer may be selected from one or more of:

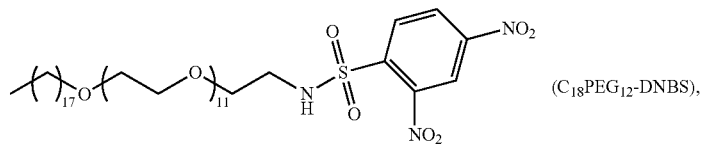

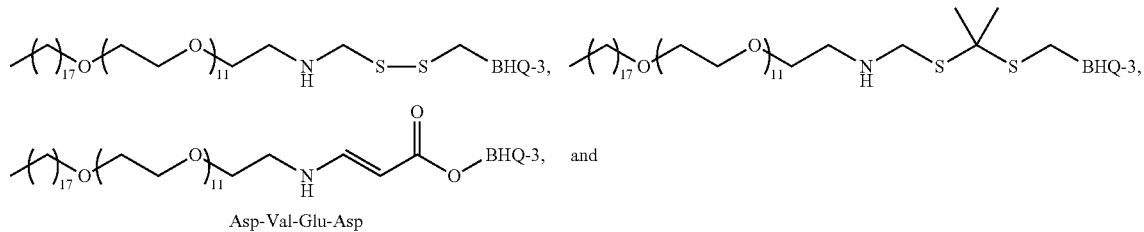

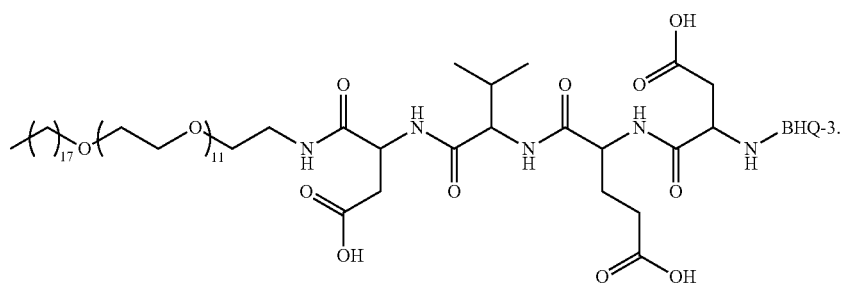

For example, amphiphilic copolymer comprising a quenching moiety may be $C_{18}PEG_{12}$-DNBS.

Thus, in particular embodiments of the invention, the amphiphilic copolymer is selected from one or more of poly(ethylene glycol)-b-poly(propylene glycol)-b-poly(ethylene glycol) (e.g. $(PEG)_{100}$-b-$(PPG)_s$-b-$(PEG)_{100}$), 1,2-distearoyl-sn-glycero-3-phosphoethanolamine-poly(ethylene glycol) (DSPE-PEG), and

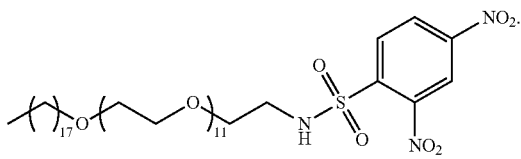

It will be appreciated that the polymer of formula I and the polymeric composite nanoparticle defined herein are capable of emitting NIR afterglow luminescence. Therefore, the composite material and/or polymer of formula I can be used in afterglow imaging techniques. With that in mind, there is provided a:

(ia) use of a polymeric composite nanoparticle as defined above, in the preparation of an imaging agent for the diagnosis of a condition or disease in a deep tissue and/or an organ using afterglow luminescence;

(ib) method of performing in vivo imaging in a deep tissue and/or an organ using a polymeric composite nanoparticle as defined above, the method comprising irradiating the polymeric composite nanoparticle with a NIR laser before or after providing the polymeric composite nanoparticle to a living organism (e.g. injecting the polymeric composite nanoparticle subcutaneously, intradermally or intravenously into a living organism), and detecting the afterglow luminescence using an imaging system/device; and (ic) polymeric composite nanoparticle as defined above, for use as an imaging agent for the diagnosis of a condition or disease in a deep tissue and/or an organ using afterglow luminescence.

It will be appreciated that the imaging mention in (ia) and (ic) may be in vitro or, more particularly, in vivo.

When used herein the term "a polymeric composite nanoparticle" with reference to the modes of use may refer to a nanoparticle as described in options (aa) to (ad) above. That is, the polymeric composite nanoparticle may only contain the semiconducting polymer of formula I or, in addition, one or both of the amphiphilic copolymer and the small molecular dye. In particular embodiments that may be referred to herein, the polymeric composite nanoparticle may contain at least one of the amphiphilic copolymer and the small molecular dye and preferably both of these components in addition to the polymer of formula I. In preferred embodiments of the invention, the polymeric composite nanoparticle may be ones in which the the amphiphilic copolymer is present and further comprises a quenching moiety that is cleavable by a reactive moiety in an in vitro or in vivo test site, such quenching moieties are described in detail above.

When used herein, the term "deep" when used with respect to tissues and/or organs means that the tissue and/or organ has an imaging depth of more than 2 cm. Organs and/or tissues that may be mentioned herein include, but are not limited to brain, lung, liver, stomach, intestine, kidney and bladder.

The terms "organism", "organisms", "patient" and "patients" include references to mammalian (e.g. human) patients. As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

When used herein the term "near infrared" or "NIR" refers to a wavelength of from 700 to 1,400 nm, such as between 700 to 1400 nm. When used herein a "NIR laser" may refer to a laser that has a wavelength of from 700 to 1,400 nm, such as from 750 to 1,000 nm, such as from 800 to 900 nm, such as 808 nm.

The term "effective amount" refers to an amount of a compound, which confers a therapeutic effect on the treated patient (e.g. sufficient to treat or prevent the disease). The effect may be objective (i.e. measurable by some test or marker) or subjective (i.e. the subject gives an indication of or feels an effect).

The polymeric composite nanoparticle may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include subcutaneous, intradermal or intravenous administration. In alternative embodiments (e.g. during surgery), the mode of administration may be by spraying a composition containing the polymeric composite nanoparticle onto the site of interest in a subject.

The polymeric composite nanoparticle will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy,* 19th ed., Mack Printing Company, Easton, Pennsylvania (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527, which is also broadly applicable to the current invention.

Otherwise, the preparation of suitable formulations may be achieved routinely by the skilled person using routine techniques and/or in accordance with standard and/or accepted pharmaceutical practice.

The amount of the polymeric composite nanoparticle formulation used in accordance with the present invention will depend on various factors, such as the size of the tissue and/or organ to be imaged, the particular patient, as well as the nanoparticles that is/are employed. In any event, the amount of the polymeric composite nanoparticle in the formulation may be determined routinely by the skilled person.

For example, a solid oral composition such as a tablet or capsule may contain from 1 to 99% (w/w) of the polymeric composite nanoparticle; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment.

A parenteral formulation (such as a solution or suspension for injection or a solution for infusion) may contain from 1 to 50% (w/w) of the polymeric composite nanoparticle; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the organ/tissue to be imaged, and the patient, to be treated, as well as the route of administration, the polymeric composite nanoparticle may be administered at varying doses to a subject in need thereof. When used herein, the term "dose" is intended to refer to the amount of the polymeric composite nanoparticle provided to an organism/subject to provide the desired image. It is not intended to imply any therapeutic efficacy.

However, the dose administered to a mammal, particularly a human, in the context of the present invention should be sufficient to effect enable imaging of the organ and/or tissue in the mammal over a reasonable timeframe. One skilled in the art will recognize that the selection of the exact dose and composition and the most appropriate delivery regimen will also be influenced by inter alia the pharmacological properties of the formulation, the nature of the organ and/or tissue to be imaged, and the physical condition and mental acuity of the recipient, the age, condition, body weight, sex of the subject, and the stage/severity of the disease that may be affecting said organ/tissue.

Administration may be continuous or intermittent (e.g. by bolus injection). The dosage may also be determined by the timing and frequency of administration. In the case of oral or parenteral administration the dosage can vary from about 0.01 mg to about 1000 mg of a polymeric composite nanoparticle according to the invention per imaging cycle.

In any event, the medical practitioner, or other skilled person, will be able to determine routinely the actual dosage, which will be most suitable for an individual subject. The above-mentioned dosages are exemplary of the average case; there can, of course, be individual instances where higher or lower dosage ranges are merited, and such are within the scope of this invention.

Nanoparticles according to the invention, in any suitable formulation can be supplied by any suitable route of administration (e.g. subcutaneous, intradermal or intravenous injection into a living subject (e.g. a mouse)). As noted above, activation of the polymeric composite nanoparticles may be accomplished after or, in some cases before, administration and delivery to the site of action. Activation before administration may be accomplished by pre-illuminating the composition for a suitable period of time with an NIR laser (e.g. 808 nm laser). If the pre-illuminated nanoparticles lose afterglow illumination before the imaging testing is concluded then they can be reactivated by illuminating the desired imaging site for a suitable period of time (e.g. 1 minute with an 808 nm laser for a mouse) before continuing the acquisition of the afterglow luminescence images. In situations where the nanoparticles are supplied in an inactive state, they can be activated by pre-illuminating the desired imaging site for a suitable period of time (e.g. 1 minute with an 808 nm laser for a mouse) before acquisition of the afterglow luminescence images is started.

As will be appreciated, when the polymeric composite nanoparticles comprise a quenching moiety as part of the amphiphilic copolymer, then a pre-activation step is not required, as the activation energy supplied would be absorbed by the quencher. In such cases, there is no pre-activation before administration, but rather a first activation is conducted in vivo once the polymeric composite nanoparticles have reached the site of interest. It will be noted that an advantage associated with polymeric composite nanoparticles that comprise a quenching moiety as part of the amphiphilic copolymer is that the tissues and/or organs to be imaged may be the only tissues and/or organs that display afterglow luminescence. More particularly, the tissues and/or organs that display afterglow luminescence may only do so when they suffer from a disease or a condition that causes the rapid cleavage of the linker group (as defined above) in the quenching moiety, so as to enable afterglow luminescence to occur. Such diseases and conditions may include a cancer/tumour or oxidative stress of the liver.

In a general example, when the subject is a mouse, the afterglow luminescence images may then be acquired at various times such as at t=0.5, 1, 2, 4, 8, 12, 24, 36 and 48 h post-injection using the IVIS Spectrum imaging system, with (re)activation of the polymeric composite nanoparticles as required. It will be appreciated that the times and frequencies of imaging may be varied depending on the subject organ and/or tissue to be imaged. As discussed in more detail below in the examples section, once the afterglow imaging has taken place, the intensities of afterglow are analysed by t-test and a guiding diagnosis result is summarized.

One particular application of the above imaging techniques is to map lymph nodes and/or visualizing tumours. Tumours that may be mentioned herein include, but are not limited to breast, lung, and liver tumours. It will be appreciated that such tissues/organs may display enhanced metabolic activity, thereby enabling the rapid removal of the quenching moieties described in certain embodiments of the current invention (i.e. polymeric composite nanoparticles where the amphiphilic copolymer comprises a quencher moiety). Thus, in particular embodiments of the invention, when the polymeric composite nanoparticles include an amphiphilic copolymer that includes a quencher it is possible to conduct the imaging techniques while conducting surgery on a subject (e.g. to remove a tumour). In this circumstance, the polymeric composite nanoparticles may be sprayed onto the site of interest directly or otherwise delivered to the site of action as described above to determine whether all of the diseased organ/tissue has been removed during said surgical procedure.

Finally, when the composite nanoparticles polymeric composite nanoparticles comprise an amphiphilic copolymer that further comprises a quenching moiety that is cleavable by a reactive moiety in an in vitro or in vivo test site as defined above (e.g. the amphiphilic copolymer may be $C_{18}PEG_{12}$-DNBS), the resulting material may be particularly suited to determining the oxidative stress in the liver of a subject. Given this, there is provided:

(iia) use of a polymeric composite nanoparticle as defined above in the first aspect of the invention, where the amphiphilic copolymer further comprises a quenching moiety that is cleavable by a reactive moiety in an in vitro or in vivo test site as defined above (e.g. the amphiphilic copolymer may be $C_{18}PEG_{12}$-DNBS), in the preparation of an imaging agent for use in a method of in vivo imaging of oxidative stress in the liver of a subject, the method comprising the steps of supplying the polymeric composite nanoparticle into a living organism, irradiating the polymeric composite nanoparticle with a NIR laser, and detecting the afterglow luminescence in the liver using an imaging system/device; (ib) a method of performing in vivo imaging of oxidative stress in the liver of a subject, using a polymeric composite nanoparticle as defined above in the first aspect of the invention, where the amphiphilic copolymer further comprises a quenching moiety that is cleavable by a reactive moiety in an in vitro or in vivo test site as defined above (e.g. the amphiphilic copolymer may be $C_{18}PEG_{12}$-DNBS), the method comprising the steps of injecting the polymeric composite nanoparticle intravenously into a living organism, then irradiating the polymeric composite nanoparticle with a NIR laser, and then detecting afterglow luminescence in the liver using an imaging system/device. In various embodiments of the invention, the afterglow luminescence of injected polymer nanoparticle may be re-activated in vivo by subjecting the living organism or part of the living organism of which the polymeric composite nanoparticle was injected subcutaneously, intradermally or intravenously to irradiation by a NIR laser; and (ic) a polymeric composite nanoparticle as defined above in the first aspect of the invention, where the amphiphilic copolymer further comprises a quenching moiety that is cleavable by a reactive moiety in an in vitro or in vivo test site as defined above (e.g. the amphiphilic copolymer may be $C_{18}PEG_{12}$-DNBS), for use as an imaging agent for determining oxidative stress in the liver of a subject using afterglow luminescence. Examples of such a test in mice is provided in the examples section.

While the oxidative stress may be any oxidative stress suffered by the liver of a subject, it may be particularly suited for determining drug-induced hepatotoxicity.

Further aspects and embodiments of the current invention and disclosure are provided by the following non-limiting examples.

EXAMPLES

The invention will be further described in connection with the following examples, which are set forth for the purposes of illustration only.

Experimental

Materials and Methods
Chemicals and Other Materials

All chemicals used in the experiments were purchased from Sigma-Aldrich unless otherwise stated. Poly(2,5-dioctyl-1,4-phenylenevinylene) (POPPV), poly[(9,9'-dioctylfluorenyl-2,7-diyl)-alt(benzo[2,1,3]thiadiazol-4,7-diyl)] (PFBT), poly(5-(2-ethylhexyloxy)-2-methoxycyanoterephthalylidene) (MEHCPV), poly[2-methoxy-5-(2-ethylhexyloxy)-1,4-phenylene] end-capped with dimethylphenyl (MEHPP) and poly[2,5-bisoctyloxy]-1,4-phenylenevinylene] (BOPPV) were purchased from Luminescence Technology Corp. Paraformaldehyde was purchased from VWR Singapore Pte Ltd. 1,10-Dibromodecane and 2-ethylhexyl bromide were purchased from TCI Ltd. Dialysis membrane with 3 kDa MWCO was purchased from Spectrum Labs.

Instrumentation and Characterizations

Proton nuclear magnetic resonance ($^1$H NMR) spectra were recorded by using a Bruker Avance II 300 MHz NMR, $CDCl_3$ or $D_2O$ was used as the solvent. The spectrum was internally referenced to the Tetramethylsilane signal at 0 ppm. Afterglow signals and images were collected and obtained with the IVIS Spectrum imaging system under bioluminescence (without excitation) mode. Fourier transform infrared (FT-IR) spectra were obtained by a Nicolet 8700 FT-IR Spectrometer. GPC results were measured by Shimadzu LC-VP system with polystyrenes as the standard and THF as the eluent. Dynamic light scattering (DLS) measurements were carried out on a Malvern Nano-ZS Particle Sizer. Transmission electron microscope (TEM) images were captured from a JEM 1400 TEM with the accelerating voltage from 40 to 120 kV.

Absorption spectra were recorded on a Shimadzu UV-2450 spectrophotometer. Fluorescence measurements were conducted on a Fluorolog 3-TCSPC spectrofluorometer (Horiba Jobin Yvon). Confocal fluorescence images of the cells were obtained by using a LSM510 confocal laser scanning microscopy (Carl Zeiss, Germany) with the excitation wavelength of 488 nm.

Fluorescence and afterglow luminescence images were acquired by an IVIS Spectrum imaging system. The 514 nm laser excitation was acquired using a green light laser (Stellar-Pro ML/150, Modu-Laser, Centerville, UT, United States) with a 514 nm filter. An 808 nm high power NIR Lasers (operating mode: CW, output power after fiber: 2.5 W, LED display: diode current, multimode fiber, fiber core diameter: 400 μm, fiber connector: SMA905, with tunable laser driver module: 0-100%, laser spot size: 1 $cm^2$) purchased from CNI Co., Ltd. was used to irradiate the samples or other irradiation sites for 1 min to generate the afterglow luminescence unless otherwise noted.

For in vitro imaging of nanoparticles, fluorescence images were acquired for 0.1 s with excitation at 465±10 nm or 430±10 nm, and emission at 580±10 or 780±10 nm unless otherwise mentioned. The intensities of the fluorescence images were calculated by integrating the area. In some experiments, emission was at 520±20 nm or 720±20 nm. For in vivo experiments, fluorescence imaging was conducted for 0.1 s with excitation at 465±10 nm or 710±10 nm and emission at 780±10 nm. For afterglow luminescence imaging, samples were pre-irradiated by 514 nm or 808 nm for 1 min at a power density of 1 $W/cm^2$ for in vitro and 0.3 $W/cm^2$ for in vivo experiments unless otherwise noted. For the in vivo experiments, the laser output was equipped with a concave lens and equipped about 10 cm above from the mouse so that the output laser can cover the whole body of mouse. In vitro acquisition of afterglow luminescence images used 0.1 s of acquisition with an open filter or a specific emission filter. In vivo acquisition of afterglow luminescence images used 30 s with an open filter.

Biological Tests
Lymph Node Imaging

For SPN-NCBS5: Test sizes were 3 mice per treatment, balancing sufficient replication of results with a reduction in mice number. All mice images were included in the analyses. Cages of mice were randomly selected for the following treatments. The solutions of SPN-NCBS5 (0.25 mg/mL, 0.05 mL) were illuminated and stored at −20° C. for one day. Warmed SPN-NCBS5 was then immediately administered to the forepaw of living mice anesthetized using 2% isoflurane in oxygen via intradermal injection. At t=30 min post-injection, the afterglow luminescence and fluorescence images were collected. At t=65 min post injection, the mice were illuminated for 1 min by 808 nm laser at a power density of 1 W/cm². The afterglow luminescence and fluorescence images were then collected at 70 min, 100 min and 130 min post injection using the without light illumination again. During the imaging process, the mice were warmed with a heating pad under continuous isoflurane anesthesia.

For SPPVN: SPPVN (450 μg/mL, 0.05 mL) was administered to the forepaw of living mice which was anesthetized using 2% isoflurane in oxygen via intradermal injection. At t=60 min post-injection, the mice were irradiated by 808 nm laser for 1 min, the afterglow luminescence and fluorescence images were acquired. The afterglow luminescence images were collected for 30 s with an open filter. The fluorescence images were acquired for 0.1 s with excitation at 710±10 nm and emission at 780±10 nm.

Tumor Mouse Model

All animal experiments were performed in compliance with the Guidelines established by the Institutional Animal Care and Use Committee (IACUC), Sing Health.

To establish tumors in eight-week-old BALB/c mice, HeLa cells ($3-5\times10^6$ cells per mouse) were suspended in DMEM supplemented medium (1 mL, 10% FBS, 1% penicillin/streptomycin antibiotics), and each mouse was injected subcutaneously on the right shoulder with 0.1 mL. Tumors were allowed to grow to a single aspect of 6-8 mm (approximately 10-15 days) before imaging experiments.

To establish tumor-bearing mouse model, 4T1 cell suspension (200 μL, $1\times10^6$) was injected subcutaneously in the left shoulder of the nude mice. Tumors were grown for approximately 7 days before imaging experiments. To establish the small-size tumor-bearing mouse model for sensitive tumor imaging, two million 4T1 cells suspended in 50 mL of 50% v/v mixture of Matrigel in supplemented DMEM (10% FBS, 1% pen/strep (100 U/mL penicillin and 100 μg/mL streptomycin) were injected subcutaneously in the shoulders of the mice to establish tumor models in six-week-old female nu/nu mice. The tumor-bearing mice were then divided into two groups, each group had three mice. For one group, tumors were grown until a single aspect was approximately 2 mm before used for in vivo imaging experiments. For another group, tumors were grown until a single aspect was approximately 1 mm before use.

The volume of tumor was calculated as follows: Volume= (½) Dd² In the equation, D represents the maximum diameter of tumor while d represents the minimum diameter of tumor.

To establish the peritoneal metastases mouse model, 4T1 cell suspension (100-200 μL, $2-4\times10^5$) was injected intraperitoneally into nude mice. Tumors were grown for approximately 3-4 days before imaging experiments.

Animals and Tumor Imaging

For SPN-NCBS5: Test sizes were 3 mice per treatment, balancing sufficient replication of results with a reduction in mice number. All mice images were included in the analyses. Cages of tumor-bearing mice were randomly selected for the following treatments. SPN-NCBS5 (0.25 mg/mL, 0.2 mL) (n=3) was systematically injected through the tail vein. Afterglow luminescence and fluorescence images were acquired at t=0.5, 1, 2, 4, 8, 12, 24, 36 and 48 h post-injection. Fluorescence images were captured with a 0.1 s acquisition time with excitation at 710±10 nm and emission at 780±10 nm. Before acquiring afterglow luminescence images, the mice was illuminated for 1 min with an 808 nm laser at a power density of 0.5 W/cm² (the 808 nm high power NIR laser was adjusted the 5.5 W output power and was used to irradiate the whole body of mouse with a distance of 15 cm). Afterglow luminescence images were captured with a 180 s acquisition time with an open filter.

For SPPVN or PPVP: SPPVN or PPVP (450 μg/mL, 200 μL) was systematically injected into 4T1 tumor bearing mice with different tumor volumes through tail vein. Afterglow luminescence and fluorescence images were then obtained at different time points post-injection. Fluorescence images were acquired for 0.1 s with excitation at 710±10 nm and emission at 780±10 nm. Before capturing afterglow luminescence images, the mice were irradiated by 808 nm laser for 1 min. Afterglow images were then acquired with a 30 s acquisition time with an open filter. For ex vivo biodistribution study, the mice were sacrificed by $CO_2$ asphyxiation, then the tumor, liver, spleen, intestine, kidney, lung and heart were harvested for fluorescence imaging to estimate the tissue distribution of SPPVN or PPVP.

In Vivo Imaging of Drug-Induced Hepatotoxicity Test group sizes were 3 mice per treatment, balancing sufficient replication of results with a reduction in mice number. With this sample size, the large projected difference in signal with drug-induced hepatotoxicity can ensure adequate power (d=4.2, α=0.003, power=0.90 using G*Power analysis) [e.g. See Liu, F. et al., Sci Rep-Uk 3 (2013)]. All mice images were included in the analyses. Mice were fasted for 8 hours prior to imaging for all drug-induced hepatotoxicity imaging. Cages of mice were randomly selected for the following treatments. Mice were treated i.p. with APAP (300 mg/kg), saline, or N-acetyl-L-cysteine (NAC, 200 mg/kg) prior to APAP (300 mg/kg) treatment. After 20 min, the APAP, saline and NAC/APAP-treated nude mice were anesthetized using 2% isoflurane in oxygen, and SPN-thiol (0.25 mg/mL, 0.2 mL) was then systematically injected through the tail vein. The fluorescence and afterglow luminescence images were collected 2 h after SPN-thiol injection. Fluorescence images were captured with a 0.1 s acquisition time, excitation at 710±10 nm, and emission at 780±10 nm. Before acquiring afterglow luminescence images, the mice were illuminated for 1 min by 808 nm laser at a power density of 1 W/cm². Afterglow luminescence images were captured with 180 s of acquisition time and an open filter. To determine the biodistribution of SPN-thiol, mice were euthanized 4 h later. The heart, lungs, liver, kidneys, and spleen were resected and placed onto black paper. All organs were pre-irradiated by 808 nm laser (1 W/cm²) for 1 min, and the afterglow luminescence images were acquired for 180 s. The afterglow luminescence intensities for each individual organ were analyzed by the ROI analysis using the Living Image 4.0 Software.

Cell Culture and Cytotoxicity Test

HeLa cervical adenocarcinoma epithelial cells were purchased from the American Type Culture Collection (ATCC). HeLa cells were cultured in DMEM (GIBCO) with 10% FBS (GIBCO) in a humidified environment at 37° C. which contains 5% CO2 and 95% air. HeLa cells were then seeded in 96-well plates (5000 cells in 200 μL per well) and cultured for 24 h, then SPPVN (final concentrations: 0, 5, 10, 20 and 40 μg/mL) solutions were added into wells. Cells were then incubated for another 24 h followed by the addition of MTS (100 μL, 0.1 mg/mL) for another 4 h. The absorbance of MTS was measured by using a microplate reader at 490 nm. Cell viabilities were calculated by the ratio of the absorbance of the cells incubated with SPPVN to that of the cells incubated with cell culture medium only.

The in vitro cytotoxicity was measured using [3-(4,5-dimethylthiazol-2-yl)-5-(3-carboxymethoxyphenyl)-2-(4-sulfophenyl)-2H-tetrazolium (MTS) viability assay in 4T1 cell line. The 4T1 cells were cultured in DMEM containing 10% FBS in a humidified environment containing 5% CO2 and 95% air at 37° C. 4T1 cells were seeded in 96-well plates (Costar, Ill., U.S.A.) at a concentration of $3\times10^4$ cells/mL. After 24 h incubation, the medium was replaced by fresh medium containing SPN-PPV-TPP suspensions at different concentrations (0, 2.5, 5, 10, 20, 30 µg/mL) and the cells were then incubated for 24 h. After the designated time intervals, MTS reagent was added into cell culture medium in 1 to 10 volume ratios for cell incubation. UV measurement (490 nm) was taken after 3 h in an incubator and normalized against untreated samples to the cell viability.

Confocal Fluorescence Imaging of Multicellular Tumor Spheroids (MCTS)

To produce MCTS, a layer of poly(2-hydroxyethylmethacrylate) (PHEMA) film was coated on the bottom of tissue culture flasks (T25). PHEMA (450 mg) was dissolved into 95% ethanol solution (30 mL) and the mixture was shaken slowly for 24 h at 37° C. After PHEMA was completely dissolved, 4 mL of solution was added into a tissue culture flask. The flask was then allowed to dry for 48 h at 37° C. To sterilize, the PHEMA coated flask must be exposed to ultraviolet light for 1 h before use. The 4T1 monolayer cells were trypsinized to ensure single-cell suspension and the cell number was counted using a hemocytometer. $5\times10^5$ 4T1 cells in 5 mL of fresh DMEM medium were placed into PHEMA-coated flask. The cells were incubated at 37° C. in humidified atmosphere with 5% $CO_2$ and the culture medium was refreshed every other day. 4T1 MCTS (about 400 µm in diameter) formed spontaneously in about 7 days. The uptake of nanoparticles by MCTS was observed by confocal laser scanning microscopy (CLSM). For each experiment, about 20 4T1 MCTS were handpicked with a Pasteur pipette and transferred into a 5 mL eppendorf tube. SPPVN or PPVP (25 µg/mL) was added to the MCTS suspension and co-cultured at 37° C. for 12 h. The medium was then removed and MCTS were washed with PBS (pH=7.4) before observation with CLSM.

In Vitro Biodegradability Study of PPV-PEGL

PPV-PEGL solution (10 µg/mL) were treated with $H_2O_2$ (100 µM) and MPO (40 µg/mL) at 37° C. in phosphate buffer (50 mM, pH=7.0) with NaCl (150 mM). $H_2O_2$ and MPO were replenished for three times after every 36 h incubation due to the loss of enzyme activity. Macrophage RAW264.7 cells were utilized for in vitro biodegradability study. RAW264.7 cells were purchased from ATCC. The cells were cultured in DMEM supplemented with 10% FBS and Penicillin/Streptomycin antibiotics (1%) in a humidified environment at 37° C. which contains 5% $CO_2$ and 95% air. After seeding the cells into the imaging dish, the cells were cultured with the medium containing PPV-PEGL (30 µg/mL) for 12 h. The cells were stimulated by lipopolysaccharide (LPS) (1 µg/mL) containing medium for 0, 4 and 12 h. The cells were stained with Hoechst 33342 (NucBlue Live ReadyProbes Reagent) for the nuclei and fixed with 4% paraformaldehyde before imaging. Confocal microscopy images of the cells were obtained with CLSM.

In Vivo Tissue-Penetration of Fluorescence and NIR Afterglow Luminescence

For fluorescence imaging, a solution of SPPVN (50 µL, 130 µg/mL) was placed under the abdomen of a living mouse. The fluorescence image was acquired for 0.1 s with excitation of 710 nm and emission at 780 nm. For the afterglow luminescence imaging, the solutions of SPPVN (50 µL, 130 µg/mL) were pre-irradiated with 514 or 808 nm laser for 1 min, and then placed the solution under the abdomen of a living mouse. The afterglow luminescence images were acquired for 30 s with an open filter.

In Vivo Imaging for Differentiating Hypoxia and Normoxia Environment

SPPVN solution was purged by $N_2$ for 5 min to remove oxygen in the solution before injection. 4T1-bearing mice were treated with purged SPPVN (130 µg/mL, 50 µL) through intratumoral injection and subcutaneous injection, respectively. Fluorescence images were acquired for 0.1 s with excitation at 710±10 nm and emission at 780±10 nm. Before capturing afterglow luminescence images, the mice were irradiated by 808 nm laser for 1 min. Afterglow images were acquired with a 30 s acquisition time with an open filter.

After anesthesia, pre-implanting tumor in the left shoulders of nude mice (n=2) were injected in situ with 50 µL of SPN2.5 (100 µg/mL, oxygen was removed via purging the solution with nitrogen). The same SPN2.5 solution was injected subcutaneously in the right shoulder of these mice. The fluorescence images of the mice were acquired at 720 nm upon excitation at 500 nm. After pre-irradiated with white light for 1 min, and afterglow images were acquired with a 30 s acquisition time with an open filter.

In Vivo Peritoneal Metastatic Tumor Imaging

For SPPVN or PPVP: SPPVN or PPVP (450 µg/mL, 200 µL) was systemically injected into peritoneal metastatic 4T1 tumor-bearing mice through the tail vein. Afterglow luminescence and fluorescence images were then obtained at different time points post-injection. At 1.5 h post-injection, the skin and peritoneum of injected mice were resected and afterglow luminescence and fluorescence images in the lower quadrant regions of mice were then obtained. Fluorescence images were acquired for 0.1 s with excitation at 710±10 nm and emission at 780±10 nm. Before capturing afterglow luminescence images, the mice were irradiated by 808 nm laser for 1 min. Afterglow images were then acquired with a 30 s acquisition time with an open filter.

SPN2.5: SPN2.5 (400 µg/mL, 200 µL) was intravenously injected into peritoneal metastatic 4T1 tumor-bearing mice. At different post injection time point (0 h, 20 min, 40 min, 1 h, 2 h, 4 h), the fluorescence images of the mice were acquired at 720 nm upon excitation at 500 nm, while the afterglow luminescence images were then acquired with a 30 s acquisition time with an open filter after irradiated with white light for 1 min. The mice were euthanized at 4 h post-injection and fluorescence and afterglow luminescence images of the organs and tumors with skin and peritoneum removed were acquired.

In Vivo Clearance of SPPVN

SPPVN (450 µg/mL, 200 µL) was systematically injected into mice through tail vein. Fluorescence images of mice were captured at t=0 h, 1 h, 2 h, 4 h, 6 h, 1 day, 2 day, 4 day, 6 day, 10 day, 13 day, 16 day and 20 day post-injection. Fluorescence images were acquired for 0.1 s acquisition time with excitation at 710±10 nm and emission at 780±10 nm.

Histological Analysis

To confirm the peritoneal metastatic tumor cells, the mice were euthanized and the tumors (tissues) were extracted and fixed in 4% paraformaldehyde. The tumors (tissues) were then embedded in paraffin S15 and cut into sections with a thickness of 10 µm for hematoxylin and eosin (H&E) staining according to the standard protocols. Images of stained slices were captured by a Nikon ECLIPSE 80i microscope (Nikon Corporation, Towa Optics, New Delhi, India).

Data Analysis

The fluorescence and afterglow luminescence images were quantified with ROI analysis using Living Image 4.0 Software. Results are expressed as the mean±SD deviation unless otherwise stated. Statistical comparisons between two groups were determined by student t-test. For all tests, p<0.05 was considered as statistically significant. All statistical calculations were performed using GraphPad Prism v.6 (GraphPad Software Inc., CA, USA.)

Preparation of Components and/or Intermediates

Preparation 1: Synthesis of Propargyl End-Capped poly(ethylene glycol) Methyl Ether ($M_n$=2000) (PEG-alkyne)

Poly(ethylene glycol) methyl ether ($M_n$=2000 g/mol) (1.0 g, 0.5 mmol) was dissolved in anhydrous THF (20 mL) under ice bath followed by the addition of sodium hydride (24 mg, 1 mmol). The resulting mixture was stirred for 1 h at 0° C. Propargyl bromide in toluene (80 wt %, 110 μL) was subsequently added into the mixture and the reaction was carried out at room temperature for 24 h. The mixture was then filtered to remove any precipitates. The obtained solution was concentrated and precipitated into excess diethyl ether to obtain a white solid. The solid was dissolved into water and dialysed against water to remove the impurities. The product was obtained after lyophilization. $^1$H NMR (300 MHz, CDCl$_3$, δ): 4.20 (d, 2H), 3.65 (s, 165H), 3.38 (s, 3H), 2.44 (t, 1H).

Preparation 2: Synthesis of 1-(10-bromodecyloxy)-4-methoxybenzene (Compound 2)

4-Methoxyphenol (0.5 g, 4 mmol) and sodium methoxide (0.24 g, 4.4 mmol) were dissolved in ethanol (10 mL) with stirring for 10 min at ambient temperature. 1,10-dibromodecane (6 g, 20 mmol) added to the solution and the reaction was carried out for 2 h under reflux conditions. After cooling the solution to room temperature, water (50 mL) was added to dilute the solution. The resulting solution was then extracted with diethyl ether (50 mL×3) and the combined organic phase was dried over anhydrous sodium sulfate overnight. After removal of diethyl ether, the crude product was purified by column chromatography using petroleum ether/dichloromethane (DCM) (100:0 to 100:25) as the eluent to give rise to the product (isolated yield: 92.4%). $^1$H NMR (300 MHz, CDCl$_3$, δ): 6.84 (s, 4H), 3.91 (t, 2H), 3.78 (s, 3H), 3.42 (t, 2H), 1.86 (m, 2H), 1.76 (m, 2H), 1.51-1.39 (m, 4H), 1.37-1.27 (m, 8H).

Preparation 3: Synthesis of 1-(2-ethylhexyloxy)-4-methoxybenzene (Compound 3)

4-Methoxyphenol (0.5 g, 4 mmol) and sodium methoxide (0.24 g, 4.4 mmol) were dissolved in ethanol (10 mL) with stirring for 10 min at ambient temperature. 2-Ethylhexyl bromide (0.96 g, 5 mmol) was added to the solution and the reaction was carried out for 2 h under reflux conditions. After cooling the solution to room temperature, water (50 mL) was added to dilute the solution. The resulting solution was extracted with diethyl ether (50 mL×3) and the combined organic phase was dried over anhydrous sodium sulfate overnight. After removal of diethyl ether, the crude product was purified by column chromatography using petroleum ether/DCM (100:0 to 100:25) as the eluent to give rise to the product (isolated yield: 87.5%). $^1$H NMR (300 MHz, CDCl$_3$, δ): 6.84 (s, 4H), 3.78 (s, 5H), 1.71 (m, 1H), 1.56-1.36 (m, 4H), 1.36-1.25 (m, 4H), 0.97-0.84 (m, 6H).

Preparation 4: Synthesis of 1-(10-bromodecyloxy)-2,5-bis(bromomethyl)-4-methoxybenzene (Compound 4)

Compound 2 (0.5 g, 1.5 mmol), paraformaldehyde (0.21 g) and hydrobromic acid in acetic acid (33 wt %, 0.7 mL) were added into acetic acid (2.8 mL). The reaction was carried out at 70° C. under nitrogen atmosphere for 4 h. DCM (40 mL) was then added into the solution and the organic phase was washed sequentially with water (30 mL×2), saturated sodium bicarbonate (30 mL) and brine (30 mL). The organic phase was dried over anhydrous sodium sulfate overnight. After removal of DCM, the crude product was purified by column chromatography using petroleum ether/DCM (100:0 to 100:20) as the eluent to give rise to the product (isolated yield: 91.1%). $^1$H NMR (300 MHz, CDCl$_3$, δ): 6.86 (s, 2H), 4.54 (s, 4H), 4.00 (t, 2H), 3.87 (s, 3H), 3.42 (t, 2H), 1.86 (m, 4H), 1.54-1.29 (m, 12H).

Preparation 5: Synthesis of 1-(2-ethylhexyloxy)-2,5-bis(bromomethyl)-4-methoxybenzene (Compound 5)

Compound 3 (0.34 g, 1.4 mmol), paraformaldehyde (0.21 g) and hydrobromic acid in acetic acid (33 wt %, 0.7 mL) were added into acetic acid (2.8 mL). The reaction was conducted at 70° C. under nitrogen atmosphere for 4 h. DCM (40 mL) was then added into the solution and the organic phase was washed sequentially with water (30 mL×2), saturated sodium bicarbonate (30 mL) and brine (30 mL). The organic phase was dried over anhydrous sodium sulfate overnight. After removal of DCM, the crude product was purified by column chromatography using petroleum ether/DCM (100:0 to 100:20) as the eluent to give rise to the product (isolated yield: 93.6%). $^1$H NMR (300 MHz, CDCl$_3$, δ): 6.86 (s, 2H), 4.53 (s, 4H), 3.87 (s, 5H), 3.87 (s, 3H), 1.71 (m, 1H), 1.56-1.36 (m, 4H), 1.41-1.29 (m, 4H), 0.96-0.79 (m, 6H).

Preparation 6: Synthesis of $C_{18}PEG_{12}$-DNBS

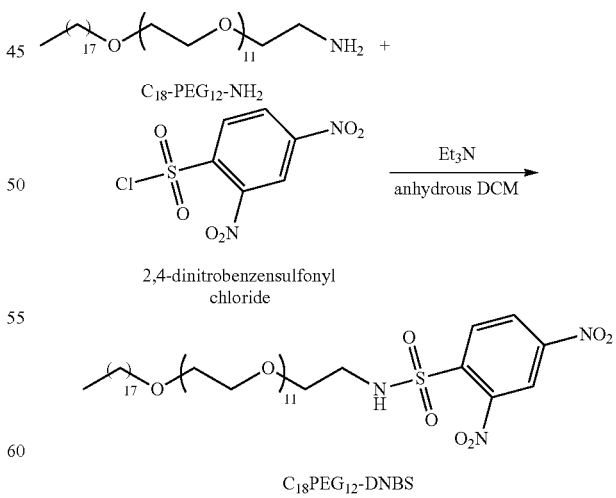

Dodecaethylene glycol octadecyl ether amine ($C_{18}$-$PEG_{12}$-$NH_2$, 80 mg, 0.1 mmol) and Et$_3$N (27.5 μL, 0.2 mmol) were dissolved in anhydrous CH$_2$Cl$_2$. The 2,4-dinitrobenzensufonyl chloride (53 mg, 0.2 mmol) was added dropwise to the above solution at 0° C., and then the solution was stirred for 8 h at room temperature under nitrogen. After the reaction, the mixture was diluted with $CH_2Cl_2$ and washed with water. The organic solvent was removed under reduced pressure, and the reaction mixture was purified by column chromatography ($CH_3OH/CH_2Cl_2$, 1:8) to yield the pure product $C_{18}PEG_{12}$-DNBS (103 mg, 80%). Mass of $C_{18}PEG_{12}$-DNBS: calculated for $C_{48}H_{90}N_3O_{18}S$, $[(M+H)^+]$: 1028.59, obsvd. ESI/MS: 1028.18. $^1H$ NMR of $C_{18}PEG_{12}$-DNBS (300 MHz, $CDCl_3$) δ (ppm): 8.52 (dd, $J_1$=8.4 Hz, $J_2$=2.1 Hz, 1H), 8.35 (d, J=8.4 Hz, 1H), 6.66 (t, 1H), 3.61 (m, 51H), 3.45-3.55 (m, 8H), 3.42 (t, 2H), 3.33 (m, 2H), 1.54 (t, 2H), 1.22 (m, 47H), 0.84 (m, 3H). $^{13}C$ NMR of $C_{18}PEG_{12}$-DNBS (75 MHz, $CDCl_3$) δ (ppm): 149.61, 147.97, 139.80, 132.54, 126.92, 120.54, 71.56, 70.55, 70.42, 70.34, 70.04, 69.12, 43.79, 31.92, 29.69, 29.65, 29.50, 29.35, 26.09, 22.68, and 14.11.

Preparation 7: Synthesis of PPV-Br1 and PPV-BrL

Compound 4 (50 mg for PPV-Br1, 5 mg for PPV-BrL) and compound 5 (0 mg for PPV-Br1, 50 mg for PPV-BrL) were dissolved in anhydrous THF (5 mL) under nitrogen atmosphere. A solution of potassium tert-butoxide in THF (1 M, 0.4 mL) was added dropwise to the solution over 40 min. The reaction was conducted at room temperature for 8 h. The solution was filtered to remove any precipitates. The obtained solution was precipitated into excess methanol to give a red solid which was washed with methanol twice. The solid collected was dried under vacuum to obtain PPV-Br1 or PPV-BrL. PPV-Br1: $^1H$ NMR (300 MHz, $CDCl_3$, δ): 7.50, 7.18, 6.66, 4.65, 4.09, 3.96, 3.75, 3.40, 1.86, 1.48-0.93. PPV-BrL: 1H NMR (300 MHz, $CDCl_3$, δ): 7.53, 7.19, 6.62, 5.13, 4.65, 4.16-3.66, 3.39, 2.04, 1.83, 1.68, 1.37, 1.25, 1.08-0.75.

Preparation 8: Synthesis of PPV-$N_3$1 and PPV-$N_3$L

PPV-Br1 or PPV-BrL (5 mg) was dissolved in a mixture of THF (2.5 mL) and N,N-dimethylformamide (1 mL). Sodium azide (2 equiv. to bromide group of PPV-Br1 or PPV-BrL) was added into the solution. The reaction was carried out at 40° C. overnight. The solvents were then removed under reduced pressure and DCM (40 mL) was added to dissolve the residue. The obtained solution was washed with water (40 mL×3) and the collected organic phase was dried over anhydrous sodium sulfate overnight. The resulting solution was concentrated and precipitated into excess methanol to give a red solid which was washed with methanol twice. The solid collected was dried under vacuum to obtain PPV-$N_3$1 or PPV-$N_3$L. PPV-$N_3$1: $^1H$ NMR (300 MHz, $CDCl_3$, δ): 7.52, 7.19, 5.36, 5.12, 4.55, 4.09, 3.96, 3.76, 3.24, 1.86, 1.47-0.99. PPV-$N_3$L: $^1H$ NMR (300 MHz, $CDCl_3$, δ): 7.53, 7.19, 6.63, 5.12, 5.01, 4.64, 4.14-3.58, 3.23, 2.04, 1.83, 1.68, 1.37, 1.26, 1.09-0.71.

Preparation 9: Synthesis of 1,4-dibromo-2,5-bis((2-ethylhexyl)oxy)benzene 2,5-Dibromohydroquinone (500 mg, 1.87 mmol), potassium carbonate (780 mg, 5.61 mmol) and dimethylformamide (DMF) were added to a 50 mL round-bottomed flask, followed by 3-(bromomethyl)heptane (0.8 mL, 4.58 mmol) addition. The reaction was carried out at 80° C. for 12 hours. The product was cooled to room temperature and extracted with dichloromethane (DCM). The organic layer was washed with water/brine and dried over anhydrous sodium sulfate. The solvent was removed under vacuum, and the crude was purified via column chromatography over silica/hexane, yielding 1,4-dibromo-2,5-bis((2-ethylhexyl)oxy)benzene (697.5 mg, 76.3% yield) as a pale viscous oil. $^1H$ NMR (300 MHz, $CDCl_3$) δ 7.08 (s, 2H), 3.82 (d, J=5.6 Hz, 4H), 1.73 (dd, J=12.1, 6.0 Hz, 2H), 1.61-1.20 (m, 16H), 0.93 (t, J=7.5 Hz, 12H).

Preparation 10: Synthesis of PPV-TPP 1,4-Dibromo-2,5-bis((2-ethylhexyl)oxy)benzene, 7,18-dibromo-5,10,15,20-tetraphenylporph-yrin, trans-1,2-Bis(tributylstannyl)ethene, tris(dibenzylideneacetone) dipalladium(0) and tri(p-tolyl)phosphine were added to a 50 mL Schlenk tube, followed by addition of chlorobenzene via syringe (degassed). The tube was charged with argon through freeze-pump-thaw cycles thrice. The reaction was carried out at 100° C. under vigorous stirring for 24 h. The mixture was cooled to room temperature and the solvent was removed under vacuum. The crude product was poured into methanol and the brown solid obtained was washed with methanol thrice. PPV: $^1H$ NMR (300 MHz, $CDCl_3$) δ 7.46 (s, 1H), 7.12 (d, J=21.9 Hz, 2H), 3.95 (t, J=29.7 Hz, 4H), 3.40 (s, 1H), 1.89 (s, 2H), 1.30 (d, J=26.2 Hz, 3H), 0.90 (s, 4H). PPV-$TPP_{2.5\%}$: $^1H$ NMR (300 MHz, $CDCl_3$) δ 8.22 (s, 1H), 7.77 (s, 2H), 7.42 (d, J=25.4 Hz, 4H), 7.12 (d, J=18.6 Hz, 4H), 4.03 (d, J=30.0 Hz, 7H), 3.43 (d, J=6.7 Hz, 8H), 1.90 (s, 14H), 1.26 (s, 6H), 0.96-0.69 (m, 5H). PPV-$TPP_{5\%}$: $^1H$ NMR (300 MHz, $CDCl_3$) δ 8.21 (s, 1H), 7.77 (s, 1H), 7.49 (s, 2H), 7.23-6.97 (m, 2H), 3.95 (t, J=31.0 Hz, 4H), 3.28 (s, 1H), 1.96 (d, J=47.6 Hz, 2H), 1.62 (d, J=34.3 Hz, 6H), 1.27 (t, J=18.3 Hz, 5H), 1.08-0.67 (m, 5H).

Example 1

Synthesis of Semiconducting Polymer Nanoparticles (SPNs): SPN-MEHPPV, SPN-PFBT, SPN-MEHPP, SPN-MEHCPV, SPN-POPPV, SPN-BOPPV, SPN-MDMOPPV, SPN-NCBS and SPN-thiol A mixed tetrahydrofuran (THF) solution (1 mL) containing MEHPPV (0.25 mg/mL) (Sigma-Aldrich) and PEG-b-PPG-b-PEG (20 mg/mL) (Sigma-Aldrich) was used to prepare SPN-MEHPPV by rapidly injecting the mixture into distilled-deionized water (9 mL, Milli-Q water) under continuous sonication with a microtip-equipped probe sonicator (Branson, W-150) at a power output of 6 watts RMS for 2 min. For SPN-NCBS, the mixed THE solution (1 mL) contained MEHPPV (0.25 mg/mL) (Sigma-Aldrich), PEG-b-PPG-b-PEG (20 mg/mL) (Sigma-Aldrich) and NCBS (from 0 to 0.025 mg/mL according to the doping amount). Other SPNs, such as SPN-PFBT, SPN-MEHPP, SPN-MEHCPV, SPN-POPPV, SPN-BOPPV and SPN-MDMOPPV were prepare in a similar manner.

For tetraphenyl porphyrin (TPP)-doped SPN-MEHPPV, the mixed THE solution (1 mL) contained MEHPPV (0.25 mg/mL) (Sigma-Aldrich), PEG-b-PPG-b-PEG (20 mg/mL) (Sigma-Aldrich) and TPP (from 0 to 0.025 mg/mL according to the doping amount). For NCBS- or TPP-doped SPN-MDMOPPV, the mixed THF solution (1 mL) contained MDMOPPV (0.25 mg/mL) (Sigma-Aldrich), PEG-b-PPG-b-PEG (20 mg/mL) (Sigma-Aldrich) and NCBS or TPP (from 0 to 0.025 mg/mL according to the doping amount).

For SPN-thiol, the mixed THE solution (1 mL) was constituted by MEHPPV (0.24 mg/mL), NCBS (12.5 µg/mL) (Sigma-Aldrich), $C_{18}PEG_{12}$-DNBS (0.5 mg/mL)

(Preparation 6) and DSPE-PEG (0.125 mg/mL) (Sigma-Aldrich). After sonication, THF was evaporated at 65° C. under nitrogen atmosphere.

The aqueous solution was filtered through a polyethersulfone (PES) syringe driven filter (0.22 μm) (Millipore), and washed thrice using a 50 K centrifugal filter units (Millipore) under centrifugation at 3,500 rpm for 15 min at 4° C. The concentrations of SPN-MEHPPV or SPN-NCBS solutions were determined by UV-Vis absorption according to their absorption coefficients. The SPN solutions were finally concentrated to 0.1 mg/mL (based on the mass of MEHPPV) by ultrafiltration and stored in dark at −4° C. All the concentrations of SPNs were based on the mass of SP.

Example 2

Screening of Semiconducting Polymers (SPs) for Afterglow

Figure 1:
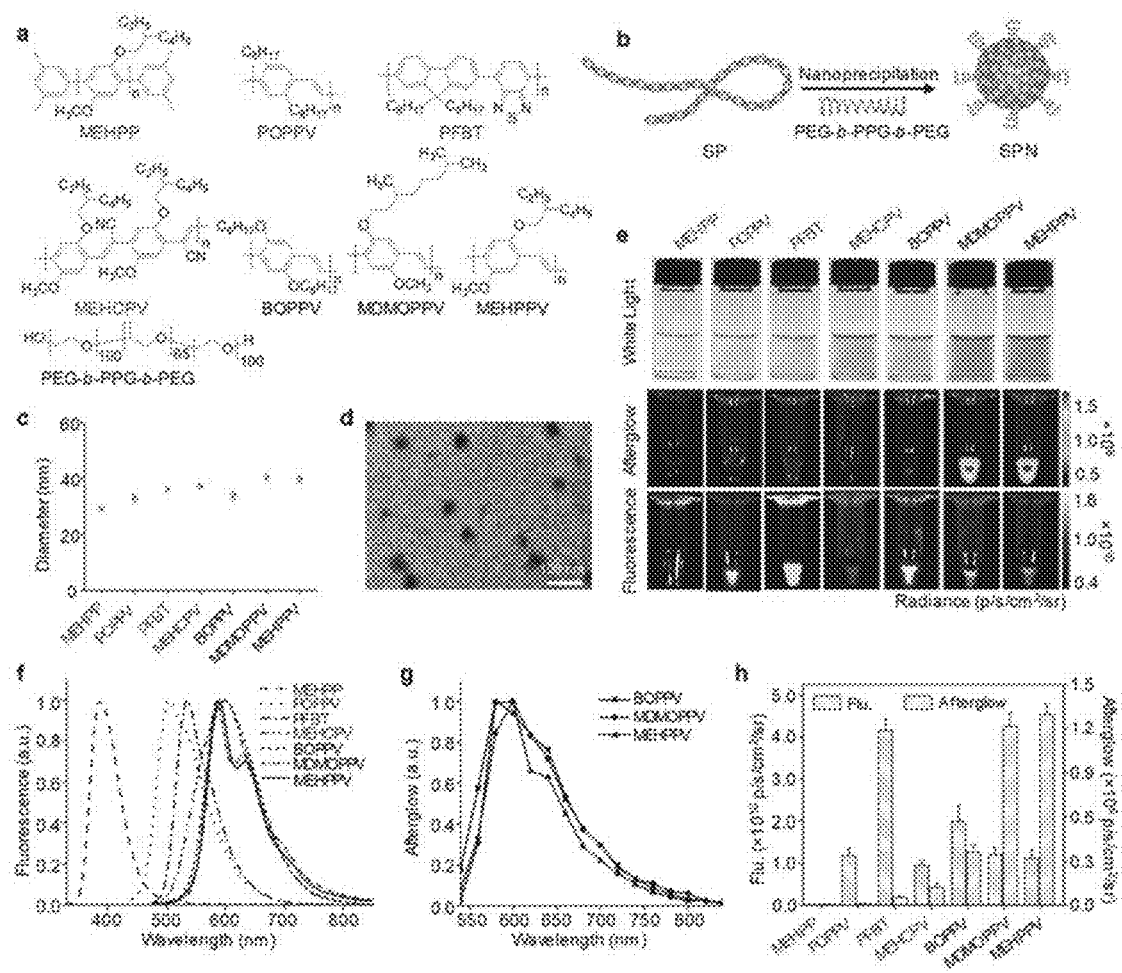
Figure 7:
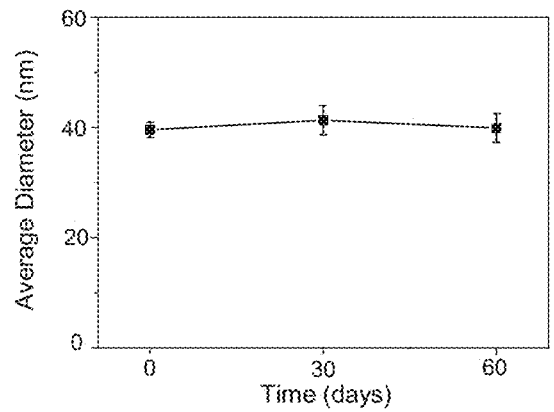
FIG. 7 show the stability of SPN-MEHPPV (10 µg/mL) in 1×PBS (pH=7.4) after storage under dark over a period of 60 days. Error bars represent standard deviation of three separate measurements.

Semiconducting polymers (SPs) such as MEHPP (Luminescence Technology Corp.), POPPV (Luminescence Technology Corp.), PFBT (Luminescence Technology Corp.), MEHCPV (Luminescence Technology Corp.), BOPPV (Luminescence Technology Corp.), MDMOPPV (Sigma-Aldrich) and MEHPPV (Sigma-Aldrich) with different molecular structures were tested to identify structures in favor of afterglow luminescence (FIG. 1a), based on the procedure described in Example 1. Nanoprecipitation was used to transform seven SPs into water-soluble nanoparticles in the presence of an amphiphilic triblock copolymer (PEG-b-PPG-b-PEG) (Sigma-Aldrich) (FIG. 1b). The hydrodynamic diameters of the SPNs measured by DLS were similar, ranging from 30 to 40 nm (FIG. 1c). Transmission electron microscopy (TEM) imaging further confirmed the spherical morphology with an average diameter of 33.9±4.3 nm (FIG. 1d), which was nearly identical to the DLS data. The nanoparticle solutions were translucent (FIG. 1e) with no precipitates or size changes even after two months of storage (FIG. 7), suggestive of excellent stability in aqueous solution.

Figure 8:
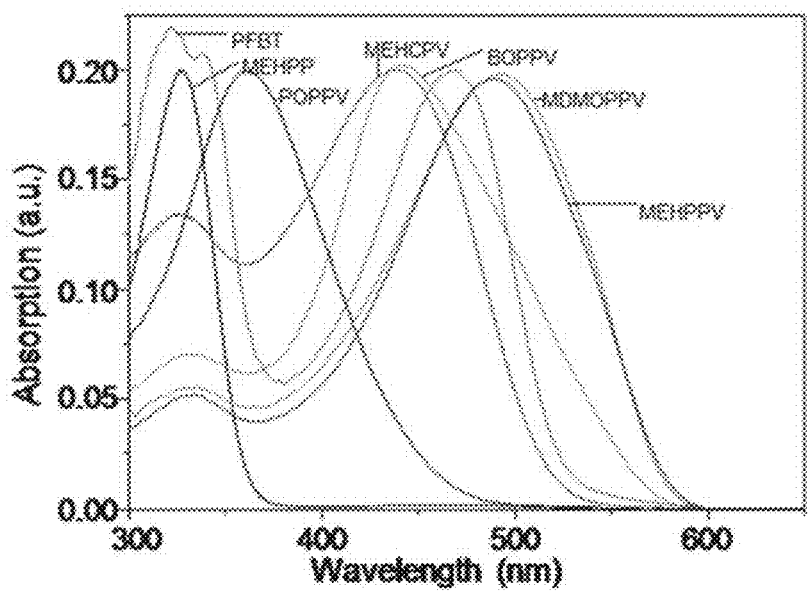
FIG. 8 shows UV-Vis absorption spectra of SPN-MEHPP, SPN-POPPV, SPN-PFBT, SPN-MEHCPV, SPN-BOPPV, SPN-MDMOPPV and SPN-MEHPPV in 1×PBS buffer (pH=7.4).
Figure 9:
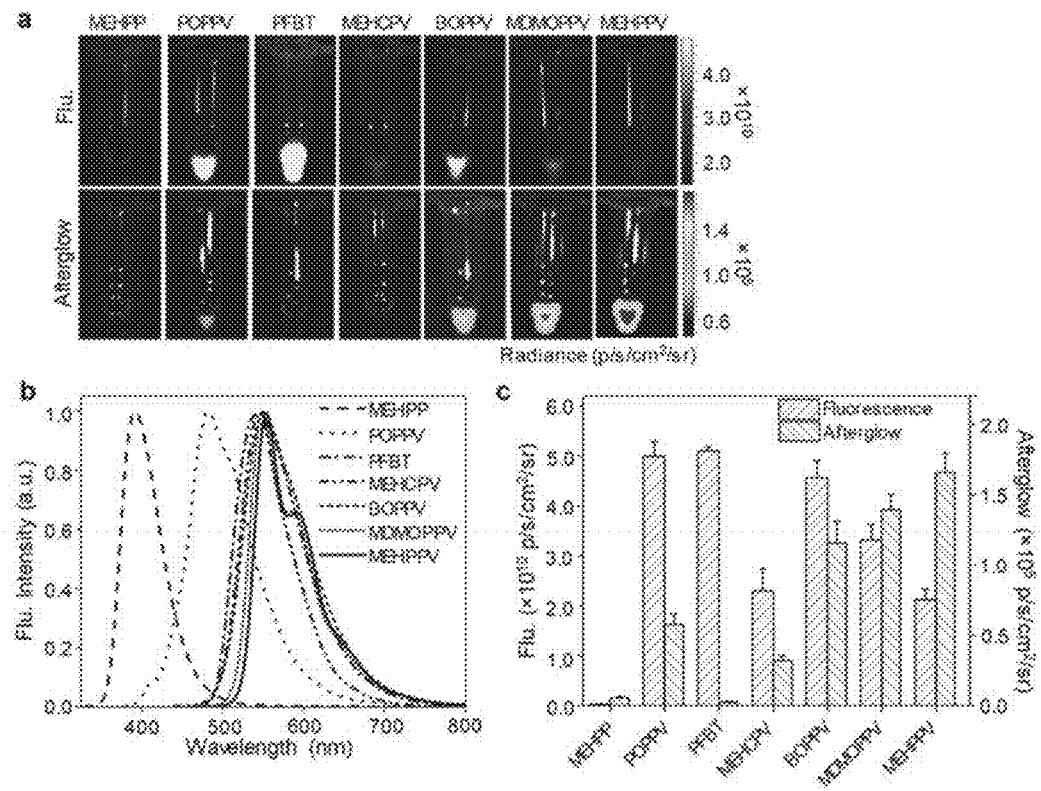
Figure 10:
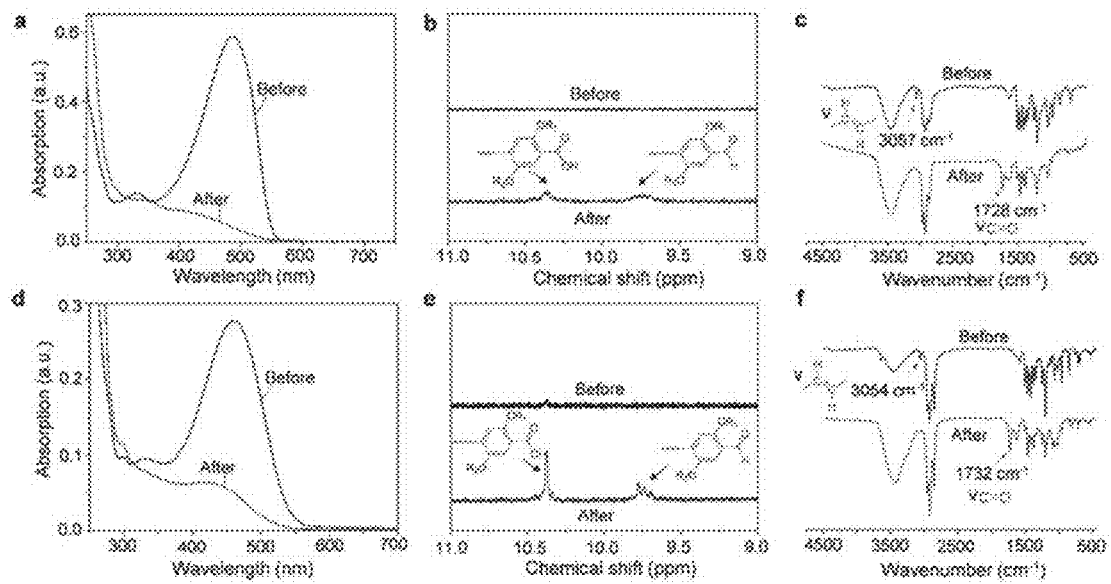

The fluorescence and afterglow signals of SPNs were collected under fluorescence (with excitation) and bioluminescence (without excitation) modes, respectively. Only PPV-based SPNs such as SPN-BOPPV, SPN-MDMOPPV and SPN-MEHPPV (synthesized based on Example 1) showed obvious afterglow luminescence (FIG. 1e, h) although their luminescence spectral profiles were similar to the fluorescence spectra (FIG. 1f, g). However, all SPNs were highly fluorescent (FIG. 1e, f). The fluorescence of SPN-MEHPP (synthesized based on Example 1) was undetectable because its absorption wavelength is too short to be excited by IVIS Spectrum imaging system (FIG. 8). Afterglow signal was only seen in PPV-based SPs suggesting that phenylenevinylene plays an essential role in the production of this real-time, excitation-free luminescence. However, some PPV-based SPs including SPN-MEHCPV and SPN-POPPV (synthesized based on Example 1) did not emit detectable afterglow luminescence suggesting that the substituents on the PPV backbone are also important. Similar afterglow behaviours were observed for SPs dispersed in THF (FIG. 9). This confirms that the chemical structure of SPs rather than the nanoparticle structure controls SPN afterglow.

Example 3

Mechanistic Study of Afterglow

Figure 2:
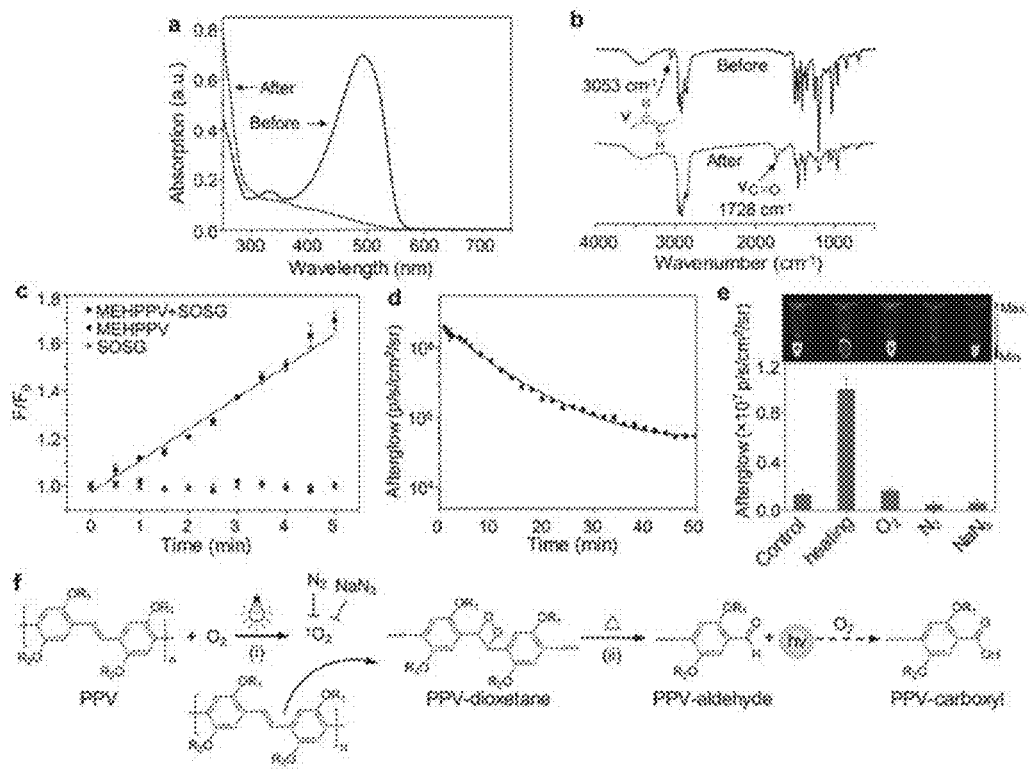
Figure 11:
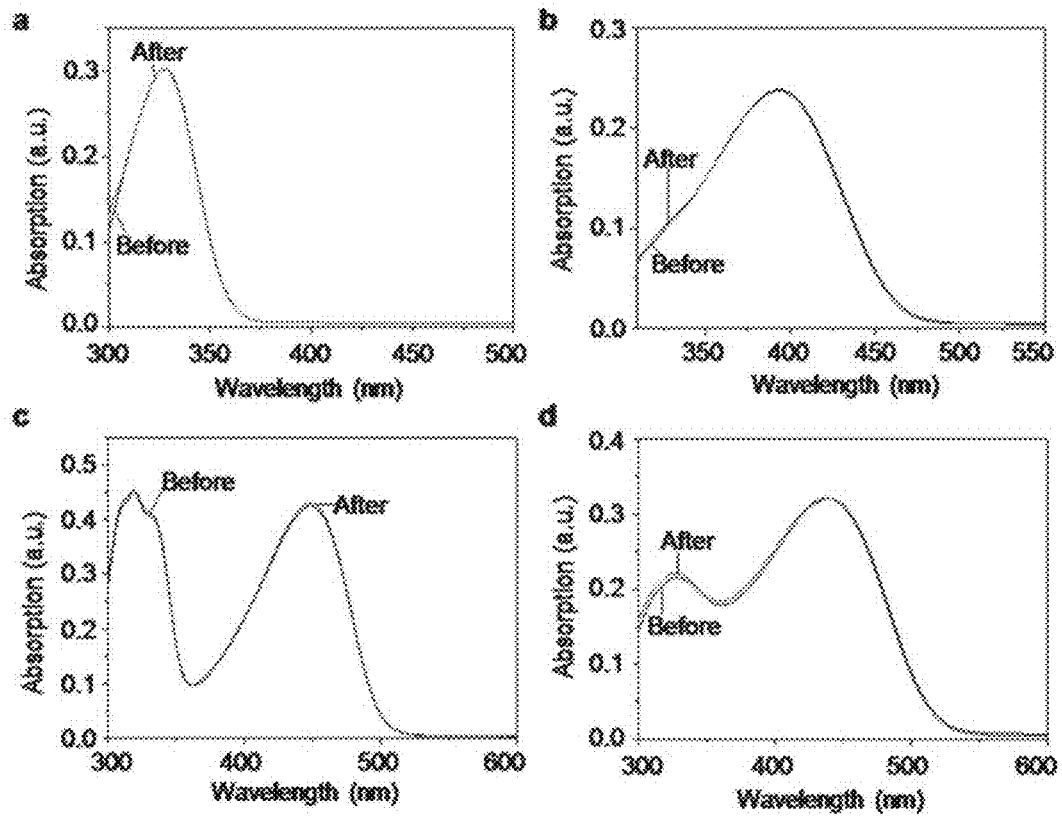

To identify the underlying mechanism governing SPN afterglow luminescence, we studied the effect of light irradiation on the chemical structures of SPs. The absorption peak of MEHPPV at 493 nm showed a remarkable hypochromatic shift and an intensity decrease after irradiation indicating a breakdown in the conjugation length and thus the decomposition of MEHPPV (Sigma-Aldrich) (FIG. 2a). Proton nuclear magnetic resonance ($^1$H NMR) analysis showed two new peaks at 9.88 and 10.47 ppm after light irradiation. These were assigned to the aldehyde and carboxyl peaks, respectively. Peak broadening and division are caused by different chemical environments and indicate the formation of inhomogeneous fragments. The characteristic peaks of oxidized MEHPPV fragments were also detected in Fourier transform infrared spectroscopy (FTIR) at 1728 cm$^{-1}$. In addition, the peak at 3053 cm$^{-1}$ corresponding to ethene-1,2-diyl groups attenuated after light irradiation, further proving the oxidation of vinylene bonds. Similar spectral changes were also observed for BOPPV (Luminescence Technology Corp.) and MDMOPPV (Sigma-Aldrich) (FIG. 10) but other SPs didn't show obvious change (FIG. 11). These data clearly suggest that light irradiation oxidizes vinylene bonds in some PPVs to break them into inhomogeneously oxidized fragments.

Next, a singlet oxygen sensor green (SOSG) was applied to test for the generation of singlet oxygen ($^1O_2$) during light-induced oxidation. After light irradiation of the SPN-MEHPPV (synthesized based on Example 1) solution for 5 min, the fluorescence intensities of SOSG at 528 nm increased by 1.69-fold (FIG. 2c). This proves that $^1O_2$ was produced during irradiation and was responsible for the oxidization of MEHPPV. Based on the results, a proposed mechanism of afterglow luminescence of PPV-based SPNs is as shown in FIG. 2f. Light irradiation of PPVs generates $^1O_2$ that oxidize the vinylene bond (C=C) via $\pi^2$-$\pi^2$ cycloaddition to form a PPV-dioxetane intermediate. This intermediate is unstable [e.g. See Scurlock, R. D., et al., *J Am Chem Soc* 117, 10194-10202 (1995)] and can spontaneously degrade into a PPV-aldehyde and generate photons. Further oxidation of the PPV-aldehyde yields PPV-carboxyl as the final product of the light-irradiation reaction. Thus, the key step in afterglow luminescence is $^1O_2$-induced formation of PPV-dioxetane, which is determined by the oxidative sensitivity of the vinyl bond in PPVs. This explains why not all PPV-based SPNs had afterglow as well as the role of the substituent. In fact, only PPVs with electron-donating substituents (alkoxyl groups) such as BOPPV, MDMOPPV and MEHPPV (synthesized based on Example 1) showed detectable afterglow luminescence whereas derivatives with weak electron-donating (alkyl groups for POPPV) (synthesized based on Example 1) or strong electron-withdrawing substituents (cyano groups for MEHCPV) (synthesized based on Example 1) do not have detectable afterglow luminescence.

The afterglow luminescence of PPV-based SPNs is long lasting with a half-life of 6.6 min at biologically relevant conditions (pH=7.4 at 37° C.) (FIG. 2c). The afterglow conditions can be controlled by changing the reaction conditions such as temperature and oxygen levels as well as the addition of an $^1O_2$ scavenger. By modulating the first pre-light-irradiation step (FIG. 2e), the afterglow of SPN-MEHPPV (synthesized based on Example 1) could be increased by 1.25-fold or decreased by 2.82-fold when measured in $O_2$- and $N_2$-saturated solutions, respectively. Moreover, the addition of the $^1O_2$ scavenger (NaN$_3$) can reduce the afterglow intensity by 2.06-fold. By modulating the second decomposition step (FIG. 2e), the afterglow intensity could be increased by 5-fold upon elevating the temperature from 37 to 60° C. However, at 0° C. afterglow was nearly completely inhibited (FIG. 12). Similar afterglow behaviour was observed for SPN-MDMOPPV and SPN-BOPPV (synthesized based on Example 1) (FIG. 12). Taken together, these data not only further validated the proposed mechanism of afterglow but also highlighted the important role of the $^1O_2$ species in determining the afterglow brightness of SPNs.

Although the mechanism that governs the afterglow luminescence of PPV-based SPNs resembles chemiluminescence [e.g. See Dodeigne, C., et al., *Talanta* 51, 415-439 (2000)], it does not require exogenous ROS to trigger the reaction. Rather, SPNs themselves can generate $^1O_2$ under light irradiation and subsequently induce afterglow luminescence. Such an afterglow mechanism also differs from that of rare-earth-doped inorganic nanoparticles wherein the absorbed photon energy is stored in intrinsic defect lattices rather than light-induced chemical defects [e.g. See Maldiney, T., et al., *J Am Chem Soc* 133, 11810-11815 (2011)].

Example 4

Optimization of Afterglow

Figure 3:
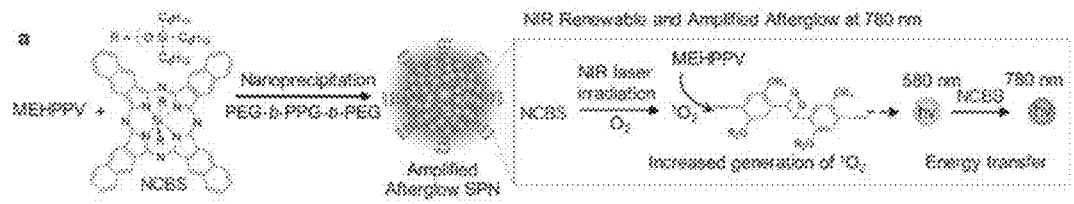
Figure 14:
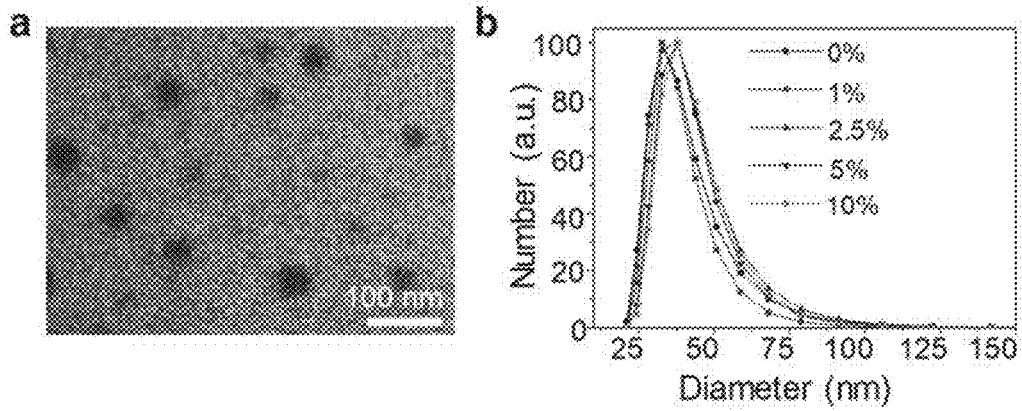
Figure 15:
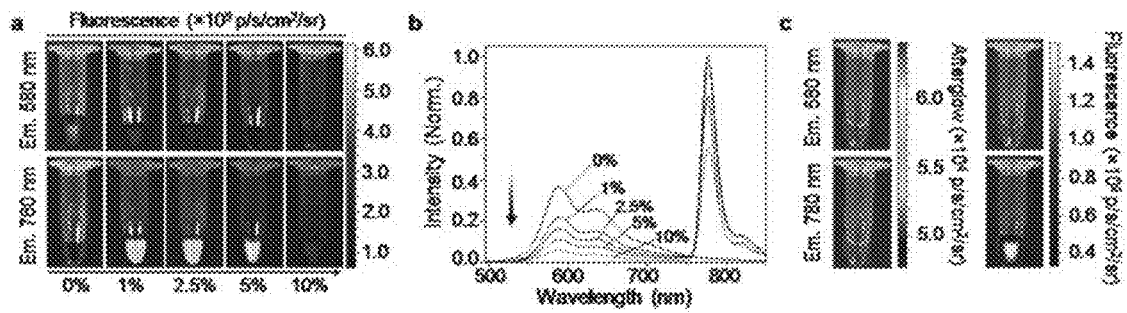
Figure 37:
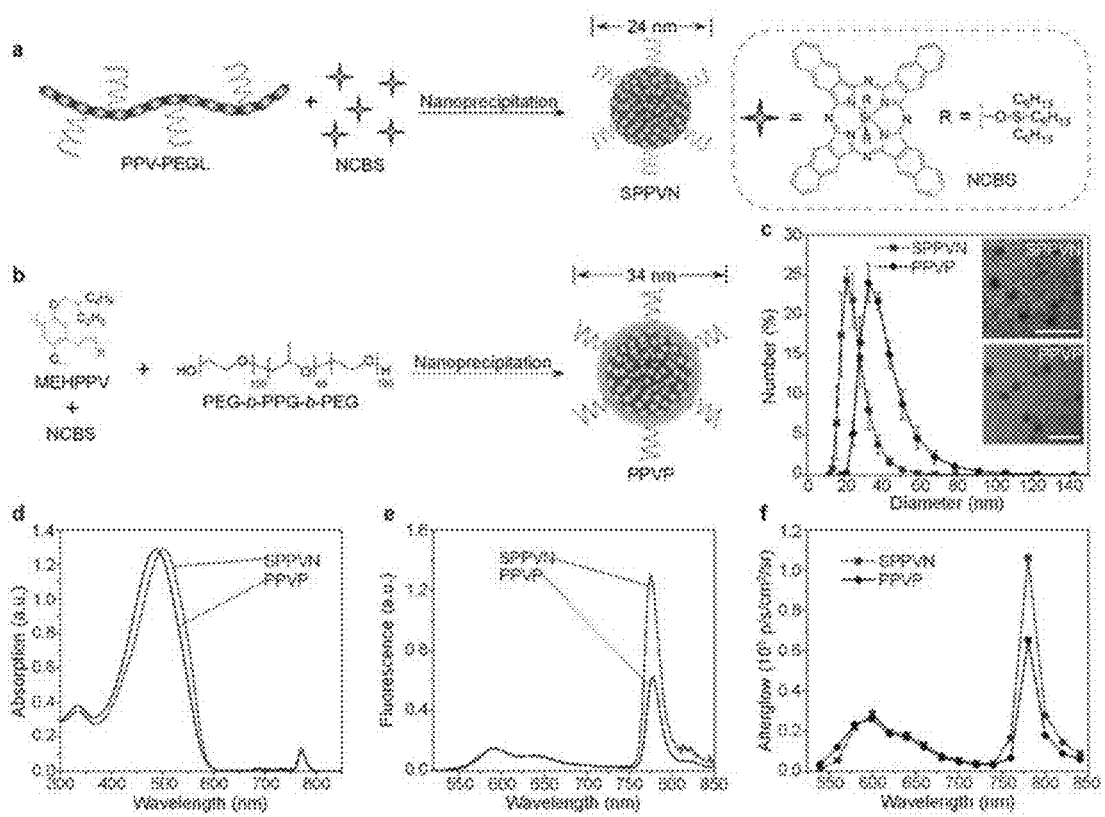

The NIR light ranging from 700 to 2,500 nm penetrates biological tissues more efficiently than visible light due to reduced tissue scattering and minimized biological autofluorescence in this region [e.g. See Smith, A. M., et al., *Nat Nanotechnol* 4, 710-711 (2009)]. To amplify afterglow and red-shift into the ideal NIR optical imaging window, a $^1O_2$ sensitizer, silicon 2,3-naphthalocyanine bis(trihexylsilyloxide) (NCBS), was doped into SPN-MEHPPV (synthesized based on Example 1) via nanoprecipitation (FIG. 3a and FIG. 37b). Since NCBS can absorb in the NIR region (FIG. 13a), it induces afterglow by pre-irradiation at 808 nm. Thus, in accordance to the synthesis of SPN-NCBS in Example 1, SPNs with different weight percentages of NCBS (1, 2.5, 5 and 10 w/w %) were prepared and referred to as SPN-NCBS1, SPN-NCBS2.5, SPN-NCBS5 and SPN-NCBS10, respectively. Doping had no obvious effect on the size and morphology of the SPNs (FIG. 14). The MEHPPV (synthesized based on Example 1) fluorescence at 580 nm gradually decreased with increasing doping concentration along with a gradual increase in NCBS emission at 775 nm (FIG. 3d, f and FIG. 15). This spectral change confirmed the efficient energy transfer from MEHPPV to NCBS. Saturation occurred at 5% and further increases in doping concentration decreased the emission of NCBS (FIG. 15) due to the self-quenching of NCBS at elevated local concentrations within the nanoparticles.

Figure 16:
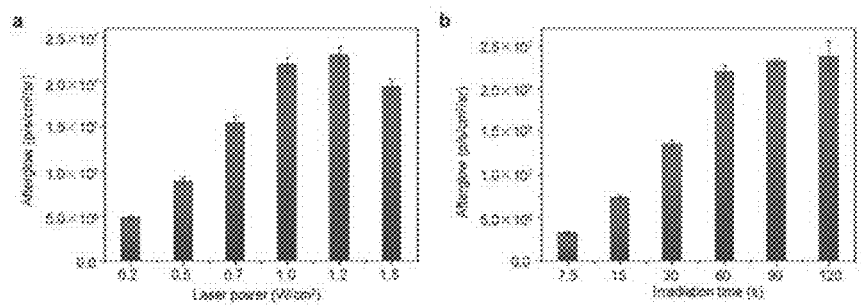
Figure 17:
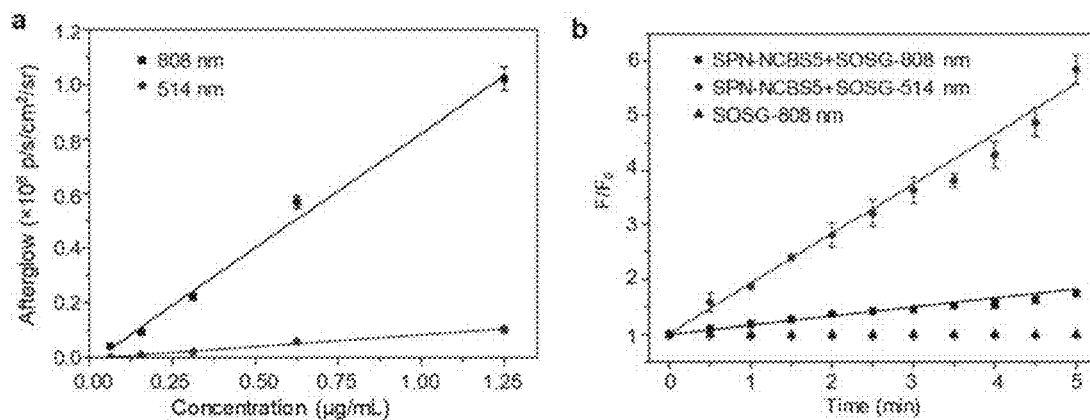
Figure 18:
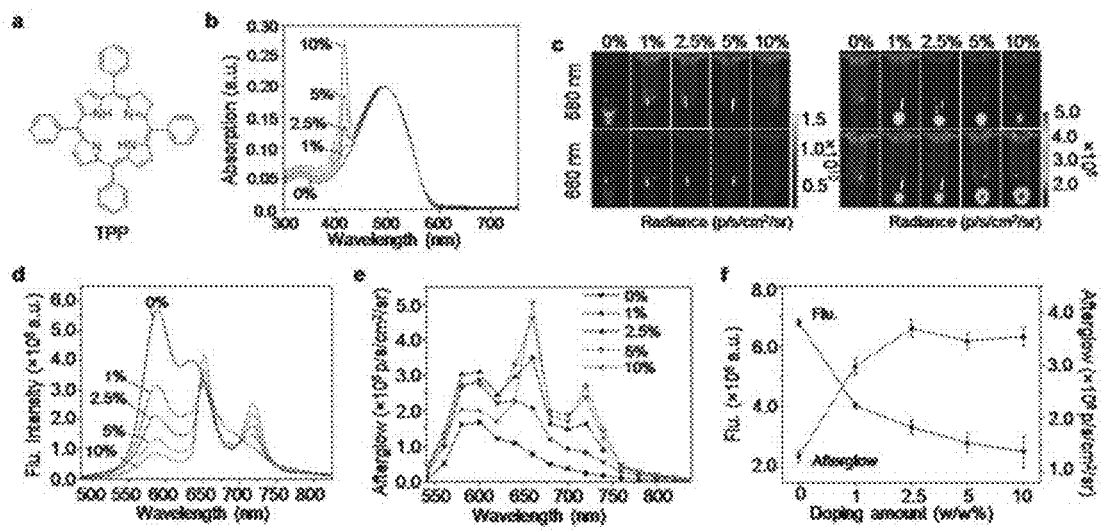
Figure 19:
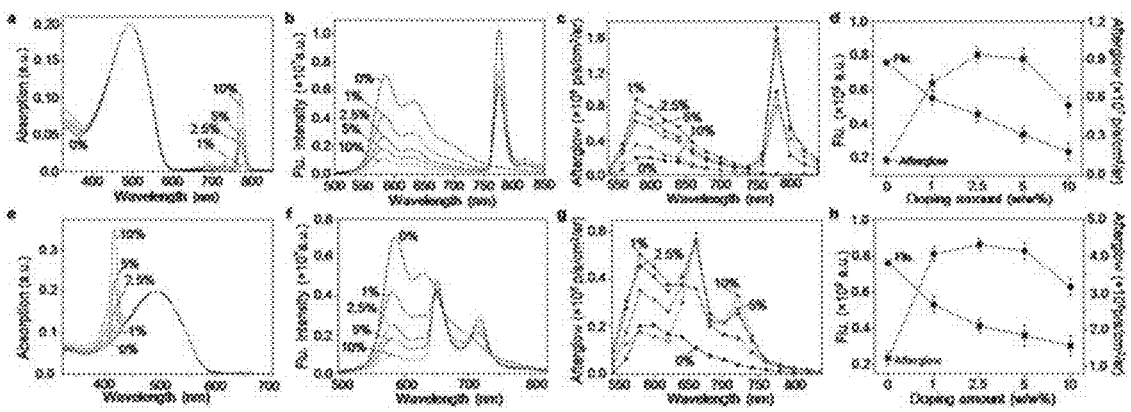

Irrespective of the pre-irradiation laser wavelength (808 or 514 nm), the afterglow intensities at both 590 and 775 nm continuously increased with increasing doping concentration (FIG. 3c, e, f). FIG. 16 shows results from the optimization of the laser irradiation conditions. Signal quantification showed that the absolute afterglow intensities induced by pre-irradiation at 514 nm increased by 6.8-fold when comparing the optimal SPN (SPN-NCBS5) with the non-doped control SPN (SPN-MEHPPV) (synthesized based on Example 1) (FIG. 3f). Moreover, the afterglow of SPN-NCBS5 could be further enhanced by 11-fold at 808 nm versus 514 nm at the same power density (FIG. 3b, c, e, f). This was attributed to NCBS' stronger ability to generate $^1O_2$ relative to MEHPPV (FIG. 17). No afterglow was detected for the nanoparticles composed of NCBS only (FIG. 15c). The $^1O_2$ sensitizer-amplified afterglow was also observed fortetraphenyl porphyrine (TPP)-doped SPN-MEHPPV and NCBS- or TPP-doped SPN-MDMOPPV (synthesized as described in Example 1) (FIGS. 18 and 19). These data suggest that $^1O_2$ sensitizers are intraparticle promoters to effectively amplify the afterglow of SPNs and modulate their emission wavelengths.

Example 5

In Vivo and In Vitro Evaluation of SPN-NCBS5

Next, in vivo and in vitro evaluation of SPN-NCBS5 was conducted in accordance to the protocols in the biological tests section. Based on the good cytocompatibility of SPN-NCBS5 (synthesized in Example 4) (FIG. 20), the amplified afterglow nanoparticle (SPN-NCBS5) is suitable for biological applications.

Tissue Penetration Study of Afterglow

The penetration depth and imaging sensitivity for the afterglow of SPN-NCBS5 (synthesized in Example 4) were examined both in vitro and in vivo. Since SPN-NCBS5 has absorption and emission in the NIR region (FIGS. 13 and 15), the fluorescence signal was acquired at 780 nm upon excitation at 710 nm (FIG. 13b); the afterglow was induced by pre-irradiation at 808 nm.

Figure 4:
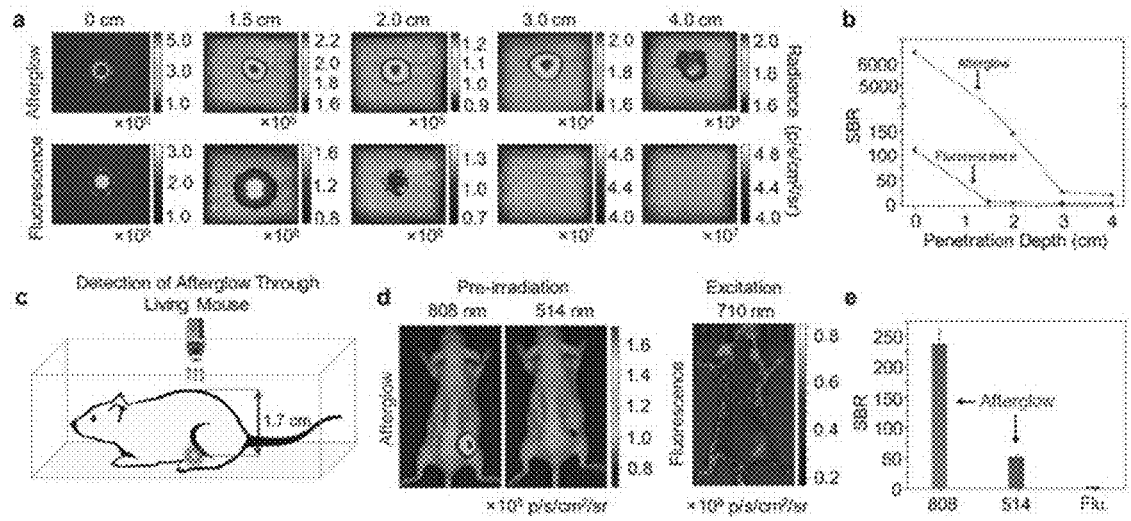

Next, chicken tissues of increasing thickness of were placed on top of the samples. The signals for both afterglow and fluorescence decreased with increased penetration depth (FIG. 4a, b). However, due to the low background noise for afterglow (824±109 p/s/cm$^2$/sr) vs fluorescence (2.53× 10$^7$±1.76×10$^6$ p/s/cm$^2$/sr), the SBR for afterglow (291±18) was 67-times higher than that for fluorescence (4.33±0.96) at a thickness of 1.5 cm. Moreover, the NIR fluorescence was close to the background noise at the thickness of 4 cm, while the SBR for afterglow was still 17.7±0.27. Similarly, the background for afterglow luminescence imaging of a living mouse was as low as 867±80 p/s/cm$^2$/sr because tissue autofluorescence was eliminated in the absence of real-time excitation. Thus, when detecting the NIR-induced afterglow signals from SPN-NCBS5 at a depth of 1.7 cm through a living mouse (FIG. 4c-e), the SBR reached 237±22, which was 4.7- and 120-times higher than the visible-light-induced afterglow (50.7±4.5) and the NIR fluorescence (1.98±0.09), respectively. Importantly, the afterglow could be repeatedly recharged by in situ irradiation at 808 nm through a chicken tissue or a living mouse (FIGS. 21 and 22) confirming the feasibility of long-term in vivo imaging.

Figure 23:
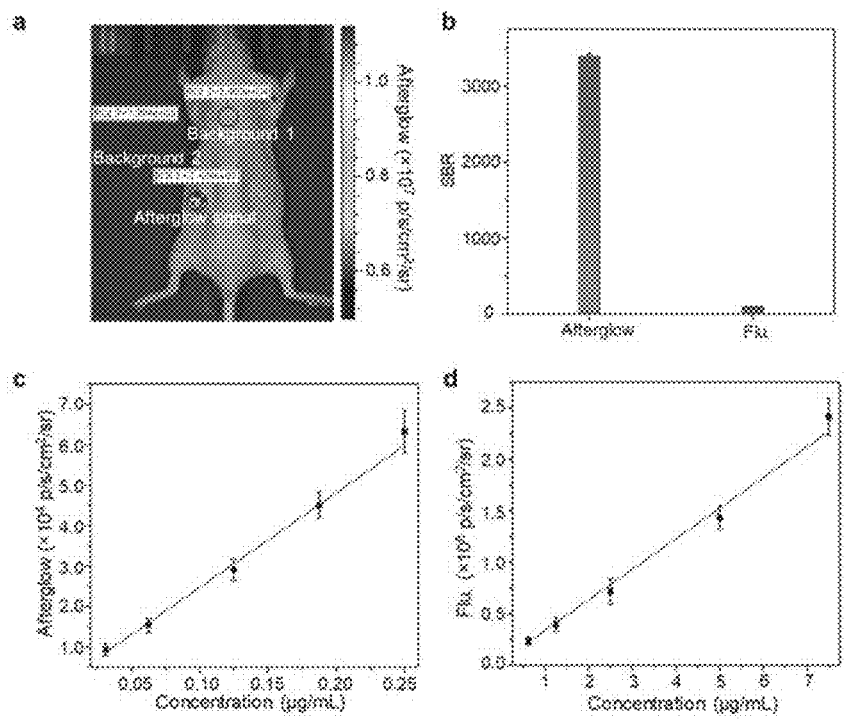

The afterglow signals of subcutaneously-implanted SPN-NCBS5 (synthesized in Example 4) in living mice has a linear correlation with its concentrations (FIG. 23c). As a result of the high SBR of afterglow, the limit of detection (LOD) of SPN-NCBS5 in living mice was 1.35 ng/mL (FIG. 23c) which is 80-times lower than that for NIR fluorescence (FIG. 23d). Furthermore, the afterglow of SPN-NCBS5 could be preserved at −20° C. after pre-irradiation, and the intensity only dropped by 3.8% after one day of storage (FIG. 24). This showed the feasibility of using the pre-irradiated afterglow SPNs directly from storage for in vivo imaging without any need for optical pre-treatment.

Afterglow Imaging of Lymph Nodes and Tumors

The storable and NIR-renewable afterglow of the amplified SPN (SPN-NCBS5) (synthesized in Example 4) was used for real-time mapping of lymph nodes in living mice (FIG. 5a) and in accordance to the protocol in the biological tests section. Lymph node mapping is clinically important in guiding surgical resection of tumor tissues [e.g. See Kim, S., et al., *Nat Biotechnol* 22, 93-97 (2004)], but has not been done using afterglow imaging previously. The pre-irradiated SPN-NCBS5 was stored at −20° C. for a day, warmed to room temperature, and then directly injected into the forepaw of living mice for continuous imaging without re-irradiation. At t=30 min post-injection, afterglow and fluorescence images were acquired. The axillary lymph node was clearly delineated with both afterglow and fluorescence imaging (FIG. 25) indicating an efficient accumulation and retention of SPN-NCBS5 in sentinel lymph nodes. Despite the decay of afterglow over 30 min at 37° C. in living mice (FIG. 26a), the SBR of afterglow images was still 7.8±1.2, which is twice as high as the fluorescence images (3.9±0.3) (FIG. 5c). After the in situ renewal of afterglow at t=65 min post-injection by irradiation at 808 nm for 1 min, the SBR of afterglow image substantially increased to 419±32: 127-fold higher than fluorescence (FIG. 5b, c). Thus, the NIR afterglow of SPN-NCBS5 could map the lymph nodes with high contrast and no need for real-time excitation during imaging.

Figure 5:
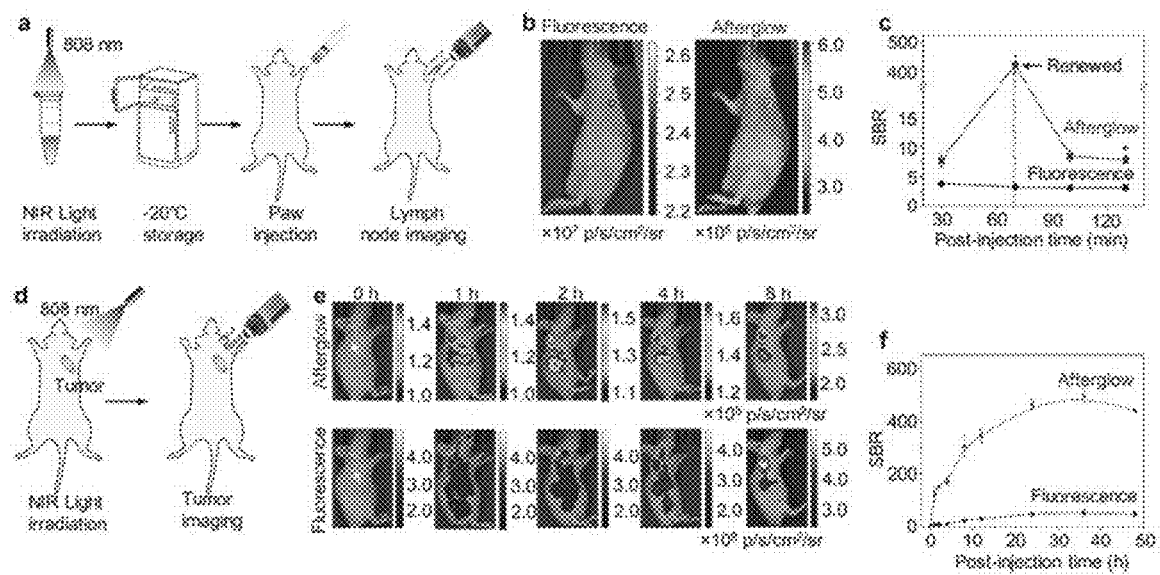

The afterglow luminescence of SPN-NCBS5 was also tested and compared with NIR fluorescence for passively targeted imaging of tumor in living mice. After tail vein injection of SPN-NCBS5, afterglow and NIR fluorescence signals were acquired in real-time. Both signals gradually increased over time, but the SBR of afterglow images were higher than NIR fluorescence at all time points (FIG. 5d, e, f). Due to the low background of afterglow, the tumor was visible at t=1 h post-injection and clearly visualized at t=2 h post-injection for afterglow imaging (FIG. 5e). In contrast, the tumor could only be visualized at t=8 h post-injection for NIR fluorescence imaging. At t=2 h, the SBR of afterglow images was 149.7±9.0, which is 23.3-fold higher than the NIR fluorescence images (6.4±0.9) (FIG. 5f). Both afterglow and fluorescence signals reached a plateau at t=36 h post-injection indicating an efficient accumulation of SPN-NCBS5 in tumor. Ex vivo data further illustrate that SPN-NCBS5 has the highest uptake in liver followed by tumor, lung, and other major organs (FIG. 27). Thus, the afterglow of SPN-NCBS5 permits faster and higher contrast imaging of tumor in living mice when compared with NIR fluorescence imaging. Moreover, the ultrasensitive NIR afterglow of SPN-NCBS5 allows for faster delineation of tumor within 2 h, which is not possible with NIR fluorescence imaging. SPN-NCBS5 has an emission of 780 nm and half-life of 396 s. With such a strong NIR afterglow, the SBR for the subcutaneously-implanted SPN-NCBS5 in living mice can reach 3387±39 at a concentration of 12.5 µg/mL. Because of this high SBR, afterglow SPNs permitted in vivo imaging of tumors after systemic administration at a much lower dosage (50 µg per mouse) than other existing afterglow agents (200 to 1000 µg per mouse), while still offering a higher SBR (FIG. 5).

Activatable Afterglow Probes for Imaging of Drug-Induced Hepatotoxicity

Drug-induced hepatotoxicity is a long-standing concern of modern medicine [e.g. See Nasr, A., et al., *Adv. Ther.* 28, 842-856 (2011)] and is one of the most common reasons that the Food and Drug Administration (FDA) withholds drug approval [e.g. See Kola, I. & Landis, J. *Nat Rev Drug Discov* 3, 711-715 (2004)]. Evaluation of potential hepatotoxicity prior to regulatory approval is challenging because current safety assays only accommodate in vitro studies and have low predictive power [e.g. See Willmann, J. K., et al., *Nat Rev Drug Discov* 7, 591-607 (2008)]. Oxidative stress and the consumption of antioxidants in the liver are concurrent early events in hepatotoxicity [e.g. See Pessayre, D., et al., *Handb. Exp. Pharmacol.*, 311-365 (2010)]. Among the antioxidants in living organisms, biothiols including cysteine (Cys), homocysteine (Hcy) and glutathione (GSH) constitute a major portion of the total body antioxidants that defend against oxidative stress. Therefore, real-time in situ imaging of biothiol levels could be a feasible way to evaluate drug-induced hepatotoxicity.

Figure 6:
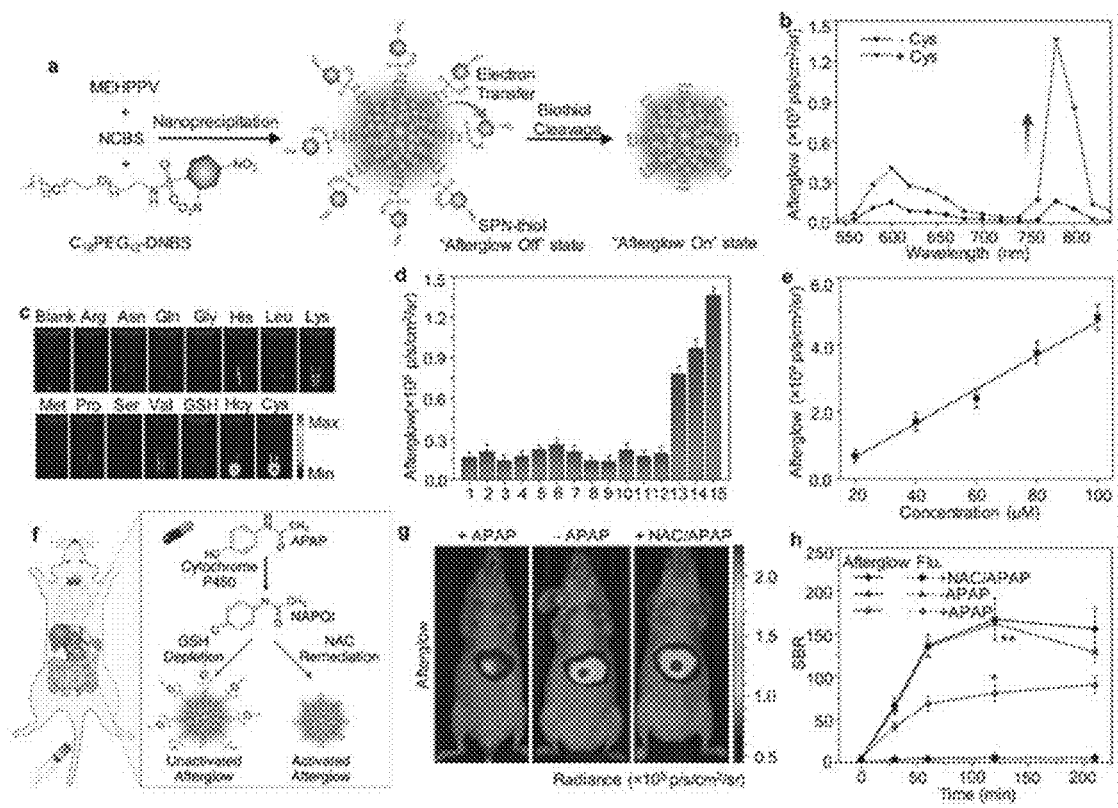
Figure 28:
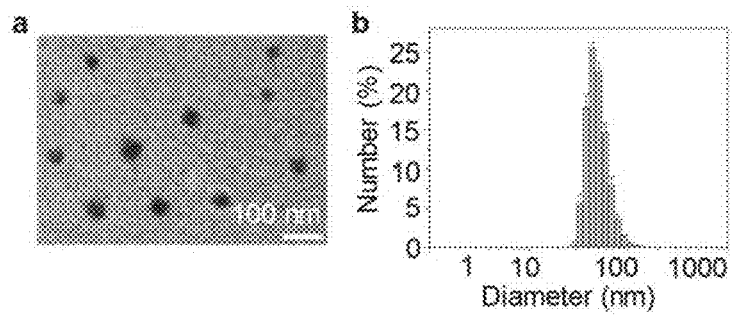
Figure 29:
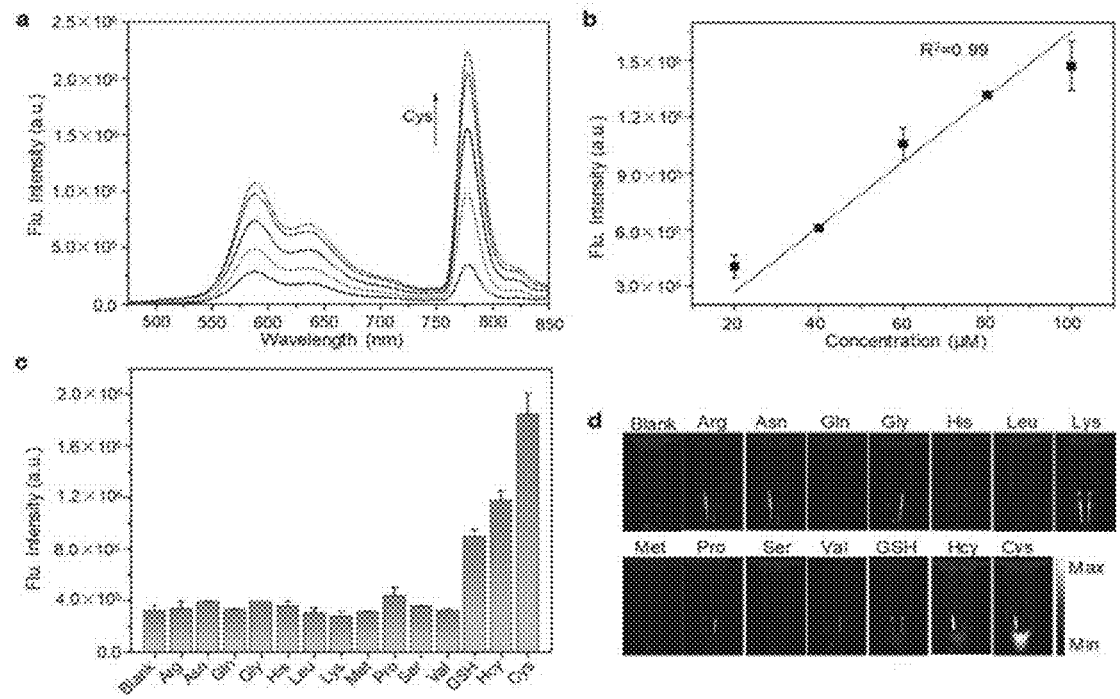

To develop activatable afterglow probes for biothiol imaging, in accordance to Example 1, an amphiphilic oligomer conjugated with an electron-withdrawing quencher ($C_{18}PEG_{12}$-DNBS) (Preparation 6) was synthesized and co-precipitated with NCBS and MEHPPV (FIG. 6a). The resulting activatable nanoprobe (SPN-thiol) has a similar size and morphology as other SPNs (FIG. 28). Due to the efficient electron transfer from the core to the quencher, the afterglow of the SPN-thiol was substantially quenched at its initial "afterglow off" state (FIG. 6a). However, in the presence of biothiols, including GSH, Cys and Hcy, the sulfonamide bond on the surface of SPN-thiol could be cleaved, releasing DNBS from the nanoparticle surface. Thus, the electron transfer was abolished leading to activated afterglow ("afterglow on" state). Upon activation by Cys, the afterglow of SPN-thiol at 780 nm increased by 8.3-fold (FIG. 6b). This was 1.75- and 1.41-fold higher than GSH and Hcy, respectively. In contrast, the signals remained nearly undetectable for other amino acids (FIG. 6c, d). This shows that SPN-thiol had high selectivity towards biothiols particularly Cys. Similar activation was observed for the fluorescence of SPN-thiol (FIG. 29). In addition, a linear correlation between the afterglow intensities and the concentrations of Cys was observed with a limit of detection (LOD) of 0.60 µM (FIG. 6e), which is more than sufficient for in vivo biological concentrations of biothiols (~0.1 and 10 mM).

SPN-thiol (synthesized based on Example 1) was used for in vivo imaging of drug-induced hepatotoxicity (FIG. 6f) and in accordance to the protocol in the biological tests section. Acetaminophen (APAP) is an antipyretic analgesic drug and was utilized as a model drug as the mechanism of APAP-induced hepatotoxicity is well established. An overdose of APAP can induce oxidative and nitrosative stress and in turn deplete biothiols to initiate a signaling cascade resulting in necrotic cell death. The mice were first treated with APAP at a toxic dosage level or saline, and then SPN-thiol was systematically administered via intravenous injection at t=20 min post-treatment of APAP. Afterglow and fluorescence signals were acquired at real-time, and they gradually increased over time (FIG. 6h). At t=2 h post-injection of SPN-thiol, the afterglow of APAP-treated mice was 1.99-times lower than saline-treated control mice (FIG. 6g) due to the decreased level of biothiols in the liver. In contrast, when the mice were protected with N-acetyl-L-cysteine (NAC, an FDA-approved antioxidant drug) before APAP treatment, the afterglow signal was comparable to that for the saline-treated control mice. This was due to the effective ROS-scavenging ability of NAC to maintain the level of antioxidants in liver. Histological studies further showed massive hepatic necrosis of the livers after 3 h of APAP treatment whereas no liver lesions were found in the saline-treated control mice or NAC-protected mice (FIG. 32). The intensity attenuation of afterglow upon APAP treatment and its increase upon NAC remediation confirmed the utility of SPN-thiol for longitudinal imaging of hepatotoxicity in vivo. In addition, the SBR ratios of afterglow were ~25-fold higher at all time intervals versus NIR fluorescence (FIG. 6h) showing the higher sensitivity of afterglow imaging for drug-induced hepatotoxicity.

The structural versatility of SPNs also facilitates the development of a smart activatable afterglow probe (SPN-thiol) for drug-induced hepatotoxicity in living mice (FIG.

6). This is the first demonstration of an afterglow system that changes signal intensity in response to a molecule of interest in vivo. Existing afterglow nanoparticles have only been used for passive or active tumor targeting. The NIR afterglow of biothiol-activatable probe (SPN-thiol) at 780 nm can be substantially activated with biothiols such as Cys, Hcy and GSH. As these biothiols are essential antioxidants against oxidative stress, SPN-thiol can detect antioxidant levels in the liver of living mice and thereby enabling real-time afterglow luminescence imaging of drug-induced hepatotoxicity and remediation at a SBR level that is 25-fold higher than NIR fluorescence imaging. More importantly, SPN-thiol can detect hepatotoxicity within 20 min of drug challenge, which is considerably shorter than that for the observation of histological changes in the liver (~3 h) [e.g. See Shuhendler, A. J., et al., *Nat Biotechnol* 32, 373-380 (2014)].

Example 6

Biodegradability and Biocompatibility of SPNs

Figure 33:
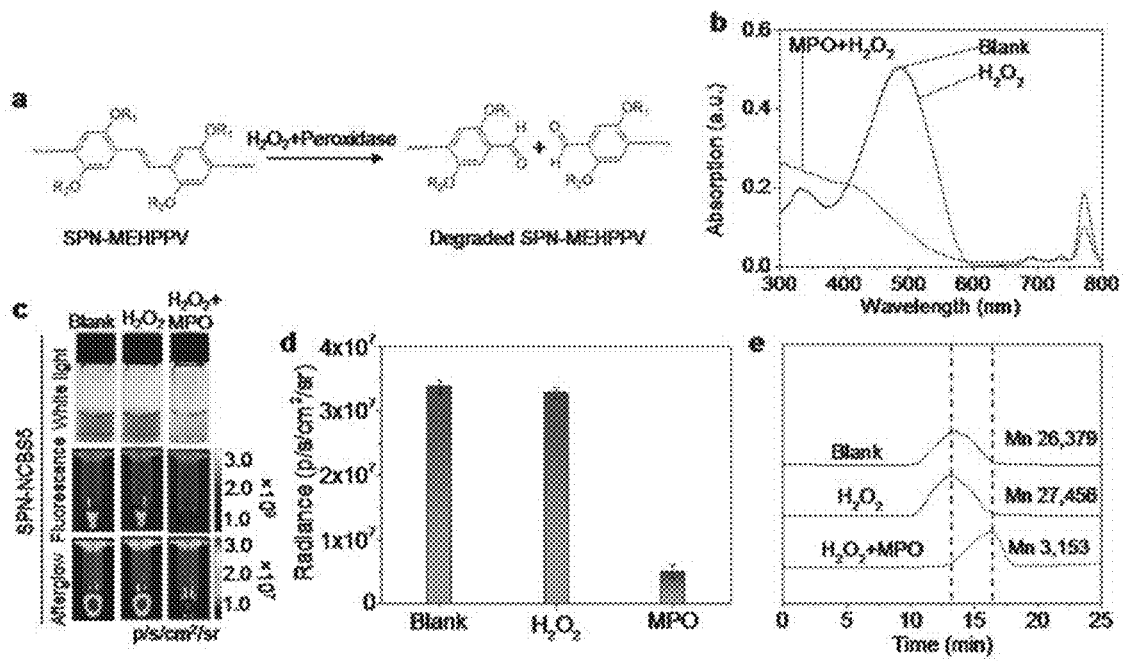

The afterglow SPNs are enzymatically degradable. As shown in FIG. 33, the degradation of SPN-NCBS5 (synthesized in Example 4) can be catalyzed by $H_2O_2$ and MPO which can be produced by immune cells such as neutrophils in living animals. After incubation with $H_2O_2$ and MPO, the vinylene bonds of MEHPPV (synthesized based on Example 1) were cleaved, leading to the formation of PPV-aldehyde fragments. The degradation was confirmed by the decrease in the absorption, fluorescence and afterglow intensities of nanoparticles as well as the significantly decreased molecular weight.

Figure 34:
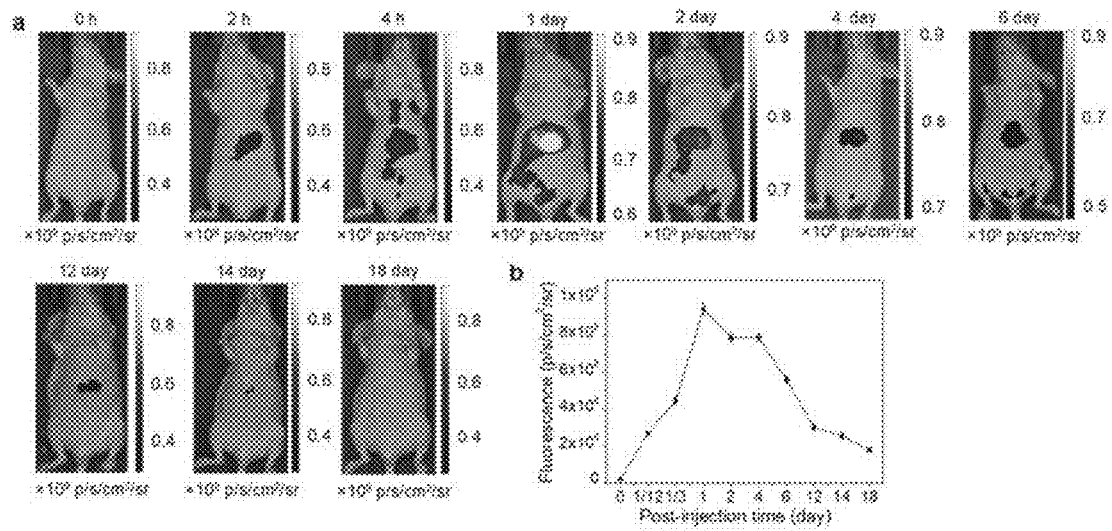

The ex vivo biodistribution data in FIG. 31 shows higher accumulation of afterglow SPNs in the liver because their size (~33 nm) is larger than 5 nm. Thus, afterglow SPNs mainly undergo hepatic clearance. As shown in FIG. 34, the enzymatic degradation of SPN-NCBS5 (synthesized based on Example 4) in liver took over 18 days, eventually leading to almost complete clearance.

The toxicity of afterglow SPNs was evaluated with histological analyses. As shown in FIG. 35, no histopathological alterations are observed for the organs from SPN-NCBS5 (synthesized in Example 4) treated mice compared to the control.

Example 7

Synthesis and Characterization of the Amphiphilic PPV Derivatives.

To endow PPV with good water solubility, the PPVs were designed to have PEG as grafting chains (FIG. 36). First, 4-methoxyphenol was respectively reacted with 1,10-dibromodecane (Sigma-Aldrich) and 2-ethylhexyl bromide (Sigma-Aldrich) to give compound 2 (Preparation 2) and compound 3 (Preparation 2). Compounds 2 and 3 were then treated with paraformaldehyde and HBr to give compound 4 (Preparation 4) and compound 5 (Preparation 5), respectively. Compound 4 was then polymerized in the presence of potassium tert-butoxide to give the PPV polymer (PPV-Br1) (Preparation 7) with the bromide groups on the side chains. To synthesize PPV with lower PEG grafting density, compounds 4 and 5 were co-polymerized and the molar ratio of compound 4 to 5 was 8 to 1 to give rise to PPV-BrL (Preparation 7). Then, these bromide PPVs were reacted with sodium azide to substitute bromide with azide, affording PPV-$N_3$1 and PPV-$N_3$L (Preparation 8). The conversion of bromide into azide was confirmed by proton nuclear magnetic resonance ($^1$H NMR) spectra (Data not shown.), which showed the shift of the resonance peak of —$CH_2$Br (3.40 ppm for PPV-Br1, 3.39 ppm for PPV-BrL) into the peak of —$CH_2N_3$ (3.24 ppm for PPV-$N_3$1, 3.23 ppm for PPV-$N_3$L) for both PPV-$N_3$1 and PPV-$N_3$L.

PPV-PEG1 and PPV-PEGL were prepared by using copper(I)-catalyzed alkyne-azide cycloaddition (CuAAC) reaction. PPV-$N_3$1 or PPV-$N_3$L (2 mg) (Preparation 8) was dissolved into THF (3 mL), followed by the addition of copper(I) bromide (2 equiv. to azide group of PPV-$N_3$1 or PPV-$N_3$L), PEG-alkyne (2 equiv. to azide group of PPV-$N_3$1 or PPV-$N_3$L) (Preparation 1) and N,N,N',N'',N'''-pentamethyldiethylenetriamine (PMDETA) (8 equiv. to azide group of PPV-$N_3$1 or PPV-$N_3$L) (Sigma-Aldrich). The reaction was carried out at room temperature under nitrogen atmosphere for 48 h. Water was added to the mixture and the resulting solution was dialysed against pure water to remove any impurities and excess PEG-alkyne. PPV-PEG1 or PPV-PEGL was obtained after lyophilization. PPV-PEG1: $^1$H NMR (300 MHz, $CDCl_3$, δ): 7.50, 7.12, 4.56, 4.18, 3.86, 3.62, 3.54, 3.38, 3.36, 1.42-1.07, 0.92-0.69. PPV-PEGL: $^1$H NMR (300 MHz, $CDCl_3$, δ): 7.54, 7.19, 5.34, 4.67, 4.14-3.79, 3.65, 3.57, 3.38, 1.68, 1.45-1.11, 1.09-0.66.

Gel permeation chromatography (GPC) showed that both PPV-PEG1 and PPV-PEGL had a molecular weight higher than their corresponding precursors (PPV-Br1 and PPV-BrL), confirming the grafting of PEG onto the PPVs backbone (Table 1).

TABLE 1

| GPC of PPV polymers | | | |
|---|---|---|---|
| Sample Name | Mn (g/mol) | Mw (g/mol) | PDI |
| PPV-Br1 | 32773 | 61613 | 1.88 |
| PPV-BrL | 16469 | 43478 | 2.64 |
| PPV-PEG1 | 59781 | 120160 | 2.01 |
| PPV-PEGL | 26565 | 78367 | 2.95 |

Figure 42:
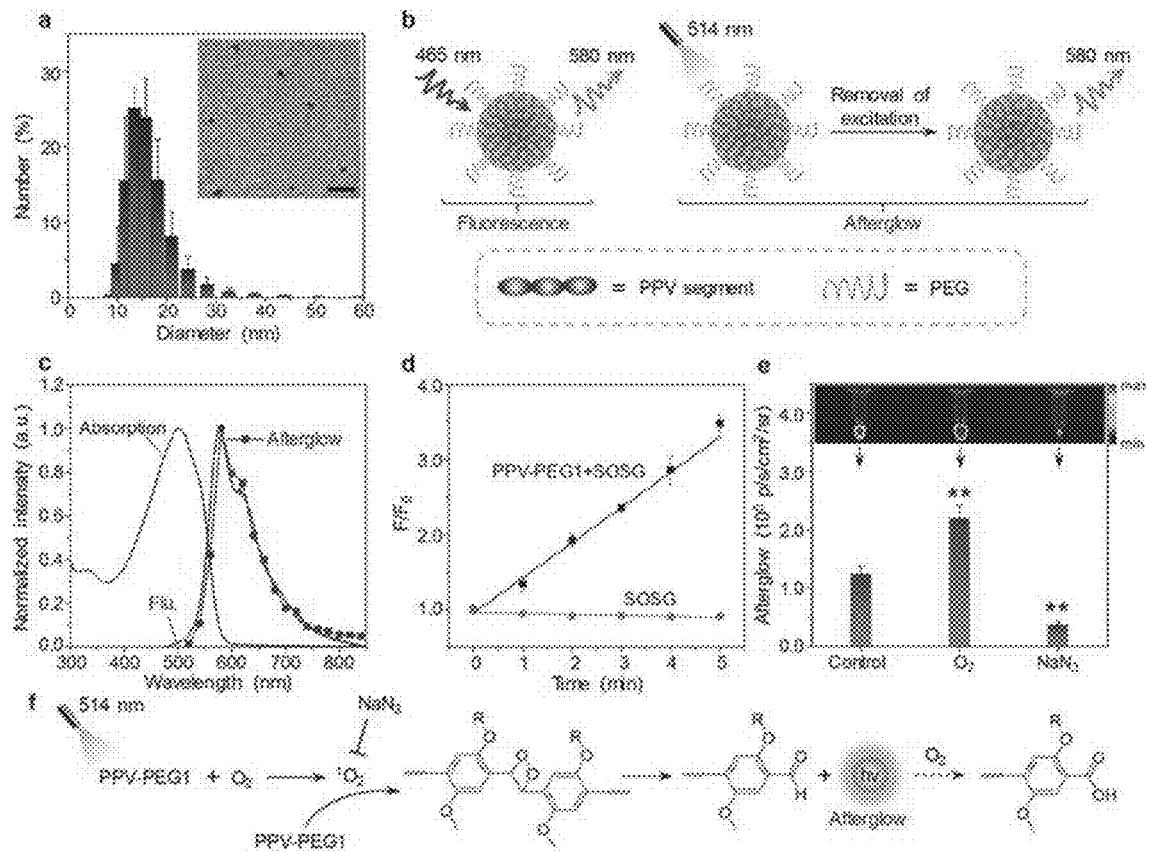
Figure 43:
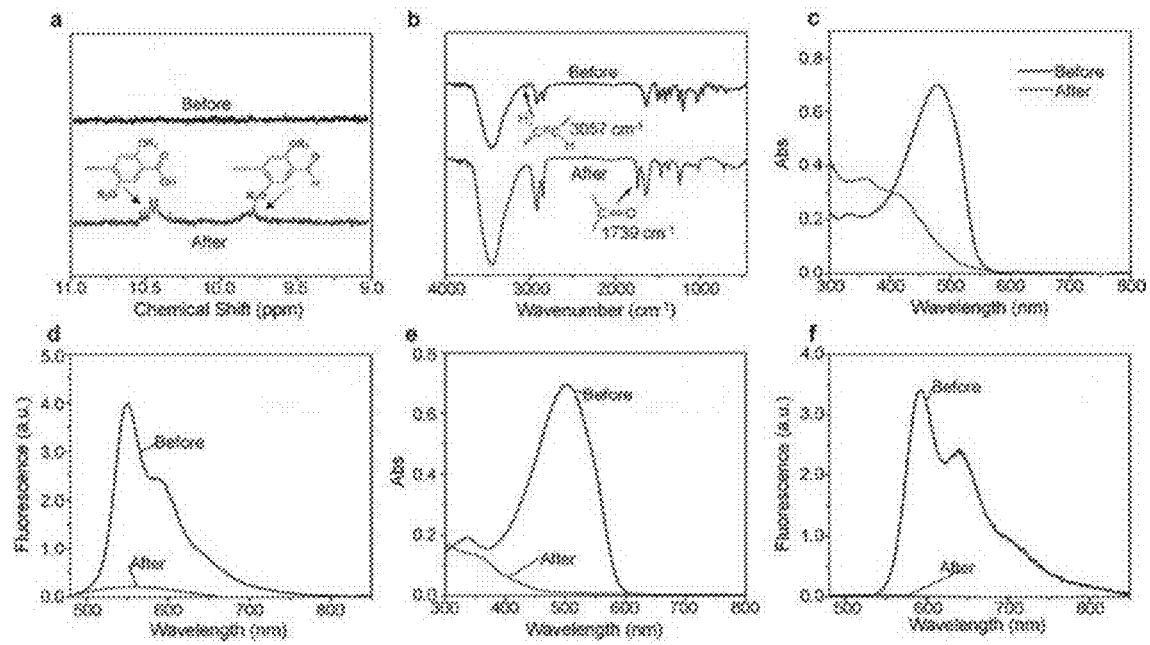
Figure 44:
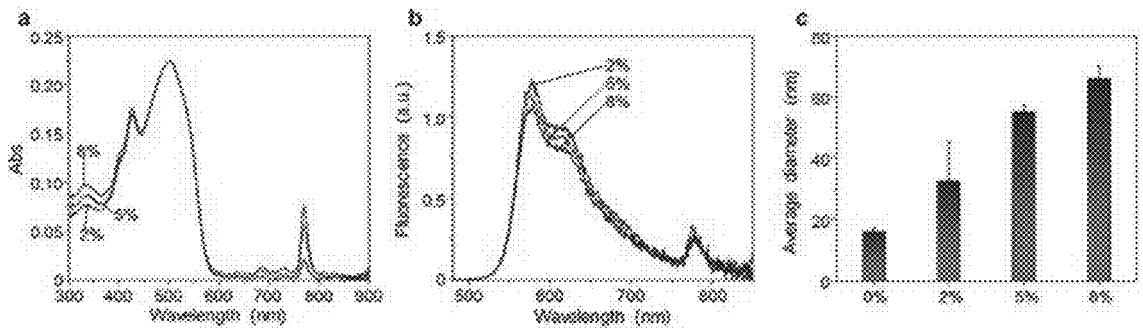

Due to its amphiphilic property, PPV-PEG1 could be directly dissolved in phosphate buffer solution (PBS) and self-assemble into small nanoparticles. The optical properties and afterglow mechanism of PPVs were studied (FIGS. 42 and 43). PPV-PEG1 exhibited strong afterglow luminescence and its spectrum was almost identical to the fluorescence spectrum with the emission maximum at 580 nm (FIG. 42c). The underlying mechanism of afterglow luminescence (FIG. 42f) was the same as previously reported nanoparticles: singlet oxygen ($^1O_2$) generated from PPVs upon light irradiation can react with the vinylene bond to form dioxetane units (as discussed in Example 3), which can generate photons upon degradation. To amplify and redshift afterglow luminescence to NIR region, a $^1O_2$ sensitizer, silicon 2,3-naphthalocyanine bis(trihexylsilyloxide) (NCBS), was doped into PPV-PEG1 (FIG. 44). However, fluorescence spectra and DLS results indicated the poor fluorescence resonance energy transfer (FRET) from PPV segments to NCBS and low encapsulation efficiency, which should be attributed to the high grafting density of PEG for PPV-PEG1.

To better encapsulate NCBS, PPV-PEGL with a lower PEG grafting density relative to PPV-PEG1 was used to prepare the NCBS-doped nanoparticles (FIG. 37a). In accordance to the synthesis of SPN-NCBS in Example 1, PPVP was prepared via nanoprecipitation of MEHPPV (Sigma-Aldrich) and NCBS (2 w/w % relative to MEHPPV) in the presence of an amphiphilic triblock copolymer (PEG-b-

PPG-b-PEG) (FIG. 3a). SPPVN and SPPVT were prepared by a nanoprecipitation method. Briefly, PPV-PEGL (20 mg), NCBS or TPP (2 w/w % relative to PPV segments) were dissolved into THF (1 mL). The solution was rapidly injected into a mixture of THF (1 mL) and water (9 mL) under vigorous sonication with a sonicator under 110 W for 1 min. THF in the solution obtained was removed under a gentle nitrogen flow, and the resulting solution was purified by filtered through a 0.22 μm PVDF syringe-driven filter. The prepared SPPVN (2 w/w % NCBS) or SPPVT (2 w/w % TPP) solution was concentrated by ultrafiltration and stored at 4° C. for subsequent use.

Figure 45:
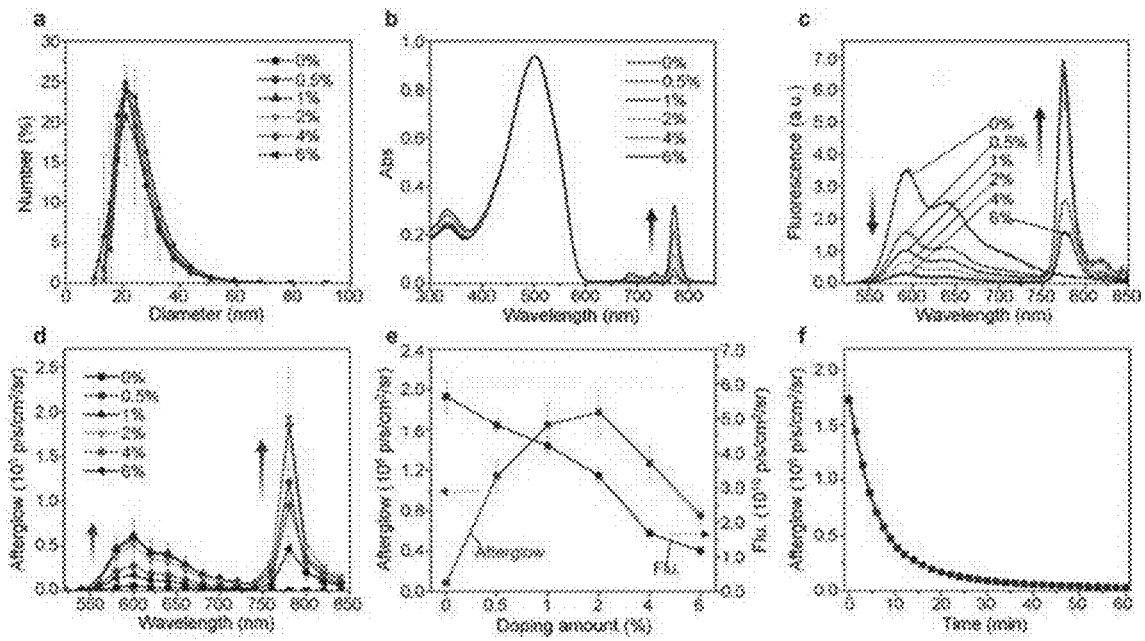
Figure 46:
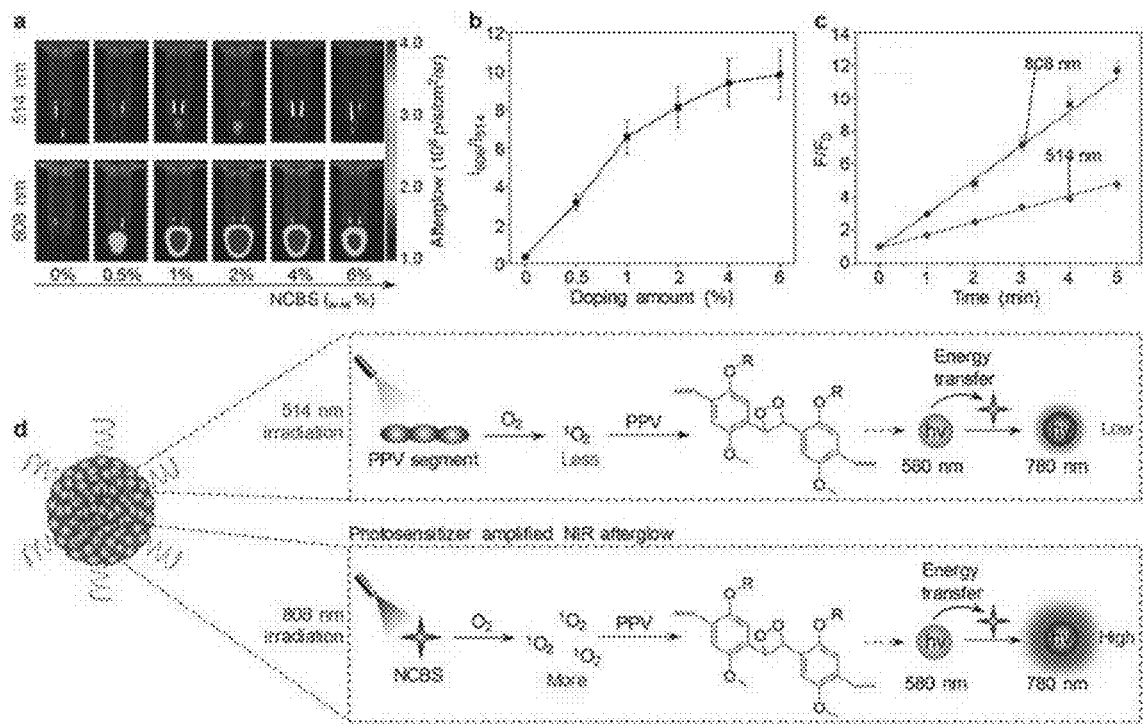
Figure 47:
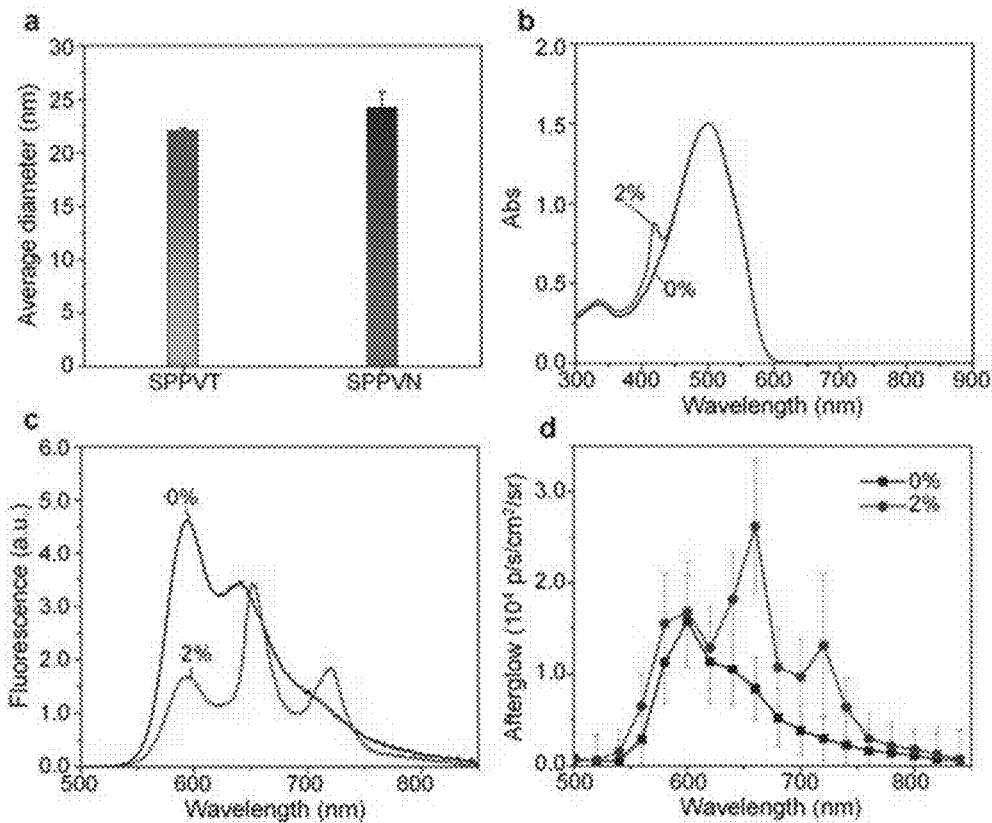

DLS results, UV and fluorescence spectra showed the successful encapsulation of NCBS and efficient FRET from PPV segments to NCBS (FIGS. 45a, 45b and 45c). The afterglow spectra profiles of NCBS-doped nanoparticles were similar to that of the fluorescence spectra (FIG. 45d). In particular, SPPVN had the highest afterglow luminescence intensity among all tested nanoparticles (FIG. 45e). The afterglow luminescence of SPPVN was long-lasting with a half-life of 4.8 min in 1×PBS buffer at room temperature (FIG. 45f). Moreover, the afterglow intensity of SPPVN induced by pre-irradiation at 808 nm was 8-times higher than that induced by pre-irradiation 514 nm, because more $^1O_2$ (2.6-fold) could be generated from NCBS upon irradiation at 808 nm (FIG. 46). Similar amplified afterglow phenomenon was detected when another photosensitizer, TPP, was used (FIG. 47). Compared to SPPVT, SPPVN had longer emission wavelength (780 vs 660 nm) and higher energy transfer efficiency (51% vs 37%), as well as higher enhancement in the afterglow intensities (20 vs 1.8-fold) than non-doped nanoparticles. SPPVN with 2 w/w % NCBS was chosen for further studies.

Example 8

Comparison of Properties of SPPVN with PPVP.

The properties of SPPVN (synthesized in Example 7) were compared with PPVP (synthesized based on Example 1 and the schematic illustrations in FIG. 3a and FIG. 37b). SPPVN has a much smaller hydrodynamic size than that of PPVP (24 vs 34 nm) (FIG. 37c). SPPVN and PPVP have similar UV absorption spectra with two maximum peaks at ~500 and 775 nm, corresponding to the absorption of PPV and NCBS, respectively (FIG. 37d). Both SPPVN and PPVP have stronger fluorescence of NCBS at 775 nm than that of PPV segments at 590 nm. However, the ratio of emission intensity at 780 nm to that of 590 nm for SPPVN was 2.1-fold higher than PPVP, indicating the higher FRET efficiency for SPPVN than PPVP (51 vs 24%) (FIG. 37e). The afterglow luminescence spectra of SPPVN and PPVP were similar to their fluorescence spectra, but the afterglow intensity of SPPVN was 1.3-fold higher than that of PPVP under same mass concentration (FIG. 37f). This improvement in FRET and enhancement in afterglow can be attributed to the closer contact between the PPV segments and NCBS within SPPVN than that in PPVP. Results also show that SPPVN has excellent physiological stability (FIG. 48a) and cytocompatibility (FIG. 48b).

Example 9

In Vivo Evaluation of SPPVN, PPVP and PPV-PEGL

Next, SPPVN (synthesized in Example 7), PPVP (synthesized in Example 1) and PPV-PEGL (synthesized in Example 7) was evaluated with in vivo imaging experiments in accordance to the protocols in the biological tests section.

Tissue Penetration Study

Figure 38:
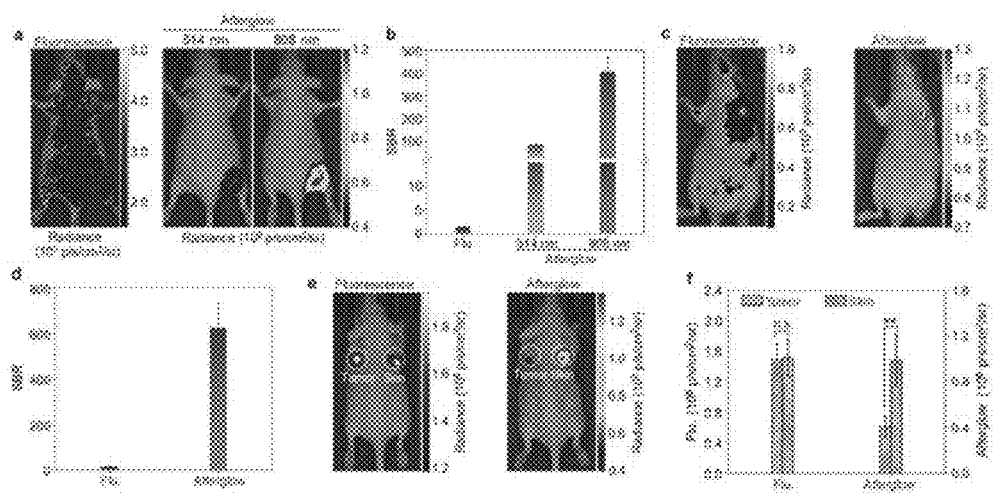

The tissue-penetration ability of afterglow imaging was compared with NIR fluorescence imaging by detection of the SPPVN solution under a living mouse with the depth of 1.6 cm (FIG. 38a). The fluorescence signal was acquired at 780 nm under the excitation at 710 nm, while the afterglow luminescence signal was acquired under bioluminescence mode after pre-irradiation at 514 or 808 nm for 1 min., The fluorescence signal from the SPPVN solution was barely distinguishable from the background signal (FIG. 38a) because of the strong tissue autofluorescence (2.06× $10^7$±1.90×$10^6$ p/s/cm²/sr). In contrast, the background signal of afterglow imaging was very low (2900±420 p/s/cm²/sr) due to the elimination of real-time light excitation. Thus, the afterglow signal was clearly detectable under pre-irradiation at both 514 and 808 nm. The SBR for afterglow imaging induced by pre-irradiation at 808 nm was 404±63 (FIG. 38b), which was ~5.0- and ~304-fold higher than the afterglow imaging induced by pre-irradiation at 514 nm (80.4±12.5) and NIR fluorescence imaging (1.3±0.2), respectively. These results demonstrate the significantly higher penetration depth and imaging sensitivity of afterglow imaging relative to NIR fluorescence imaging.

The afterglow luminescence of SPPVN decayed slightly faster in vivo than in vitro (FIG. 49a vs 45f,) because of the higher environmental temperature in living mice. Nevertheless, the afterglow of SPPVN could be repeatedly induced by pre-irradiation at 808 nm in living mice for at least 6 times without obvious decrease in the afterglow intensity (FIG. 49b). This demonstrates its utility for long-term in vivo imaging. SPPVN has a long NIR emission of 780 nm and half-life of 288 s. Moreover, in vivo afterglow intensity of subcutaneously-injected SPPVN (1.36×$10^5$ (p/s/cm²/sr)/ (μg/mL)) is 27.2-fold higher than that of inorganic persistent nanoparticles such as $ZnGa_2O_4:Cr^{3+}$ nanoparticles (FIG. 49c). The SBR for subcutaneously-injected SPPVN at 130 μg/mL (4170±179) can be 15.2-fold higher than $ZnGa_2O_4$: $Cr^{3+}$ nanoparticles (275) even when tested at higher concentration (2 mg/mL) [e.g. See Li, Z. J., et al., *J Am Chem Soc* 137, 5304-5307 (2015)].

Lymph Node Imaging Study

The utility of SPPVN for lymph node imaging was tested after forepaw injection in living mice (FIG. 38c). NIR Fluorescence and afterglow luminescence images were acquired at t=60 min post-injection. The axillary lymph node was delineated with both afterglow and fluorescence imaging. Only afterglow imaging showed a low background image of the lymph node (FIG. 38h). Imaging quantification revealed that the SBR of afterglow imaging (622±104) was 41-fold higher than that of fluorescence imaging (15±3) (FIG. 38i). These results show that afterglow imaging using SPPVN allow mapping of the lymph node with a much higher contrast than NIR fluorescence imaging.

In Vivo Imaging for Differentiating Hypoxia and Normoxia Environment.

Most tumor cells are in a hypoxic environment resulting from rapid oxygen consumption for vasculature growth and cell proliferation [e.g. See Carmeliet P. and Jain R. K. *Nature*. 473, 298-307 (2011)]. Tumor hypoxia is also associated with increased risk of invasion and metastasis. Therefore, imaging of tumor hypoxia can be help for diagnosis and treatment of cancer. The ability of SPPVN to differentiate hypoxia and normoxia was tested in vivo since afterglow was sensitive to oxygen (FIG. 42e). The SPPVN solutions were first purged with $N_2$ to remove residual oxygen, and then locally injected into tumor or under skin (FIG. 38e). The fluorescence intensities of locally injected tumor and skin were almost the same (FIG. 38e). In contrast, the afterglow intensity of locally injected skin was 2.4-fold higher than that of the tumor (FIGS. 38e and 38f). This difference in afterglow intensity was due to the hypoxic environment of the tumor, which had a low oxygen level that reduced the afterglow intensity of SPPVN. Therefore, these results demonstrate that the oxygen-sensitive afterglow of SPPVN could be used to monitor hypoxia and normoxia.

Figure 39:
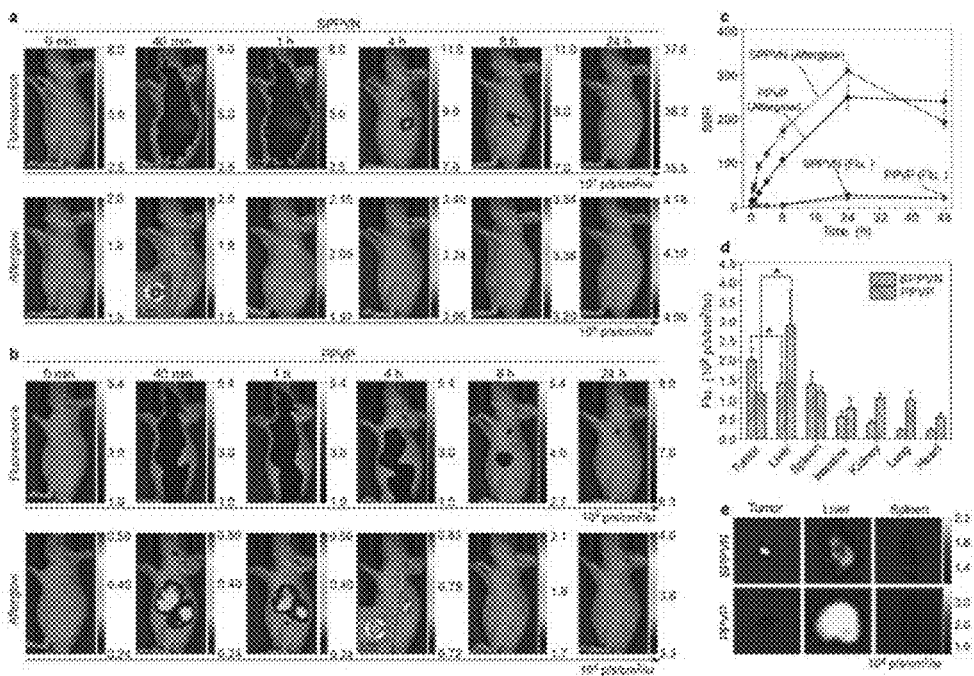
Figure 50:
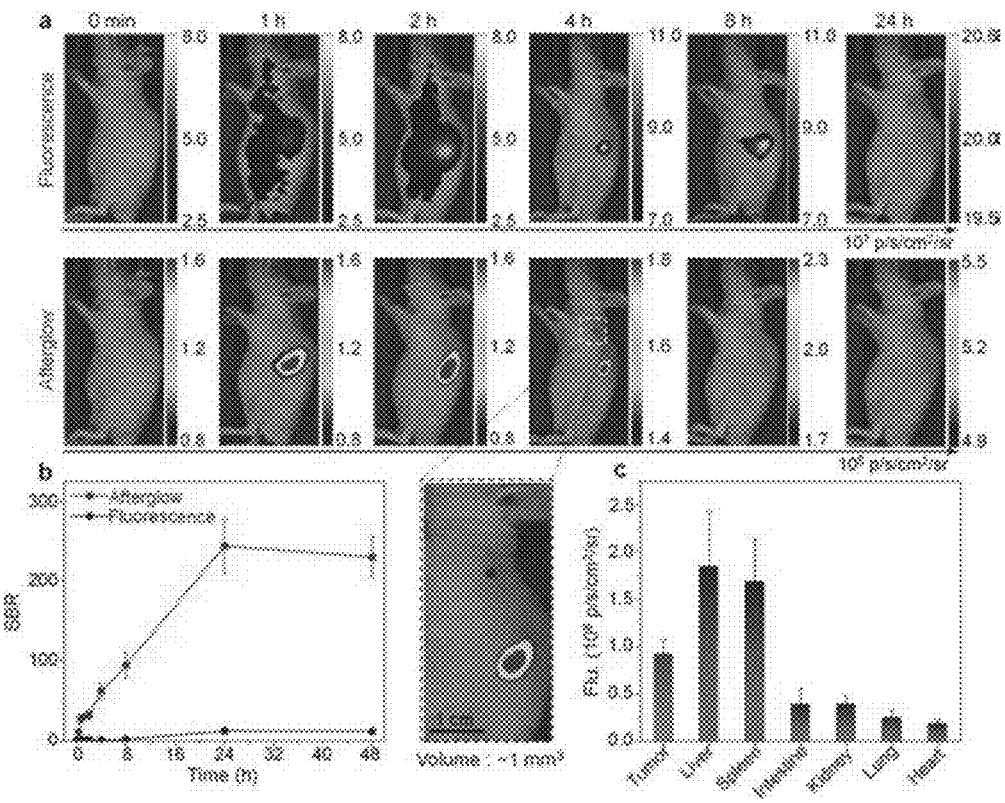
Figure 51:
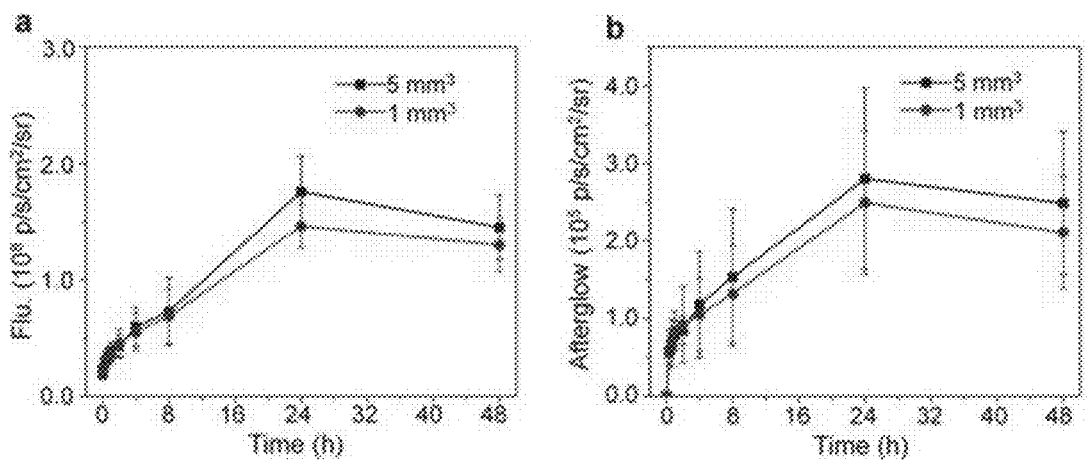

The afterglow luminescence of SPPVN was applied for in vivo tumor imaging in comparison with PPVP. Both SPPVN and PPVP were exposed to air before injection. To test the ability of early detection, the imaging experiments were conducted for the living mice bearing the xenograft tumor with the size of only ~5 mm$^3$. Fluorescence and afterglow signals were longitudinally acquired after systemic administration of nanoparticles through tail vein injection. For both SPPVN and PPVP, the afterglow and fluorescence signals gradually increased and reached saturation at 24 h post-injection, but the afterglow imaging images had higher SBR than fluorescence images at each time point (FIGS. 39a, 39b and 39c). At 24 h, the SBR in the afterglow imaging of SPPVN-injected mice was 306±20, 11-fold higher than that in the NIR fluorescence imaging (28±1) (FIG. 39c). Because of such high SBR, the tumor was detected with afterglow imaging as early as 40 min post-injection of SPPVN; in contrast, fluorescence was only detected at 4 h post-injection (FIG. 39a). For PPVP-injected mice, the tumor could only be visualized at t=4 and 8 h post-injection for afterglow imaging and fluorescence imaging, respectively (FIG. 39b). At t=40 min post-injection of nanoparticles, the SBR of afterglow imaging for SPPVN-injected mice was 40±3, ~22-fold higher than that of NIR fluorescence imaging (1.8±0.2), and ~2.5-fold higher than afterglow imaging of PPVP (15.7±1.5) (FIG. 39c). As a result of the high sensitivity of SPPVN, its afterglow allow detection of tumor with the size as small as ~1 mm$^3$ at 4 h post-injection with the SBR of 63±10. This was only possible at 24 h post-injection for NIR fluorescence imaging (FIG. 50). Note that the real-time fluorescence and afterglow luminescence signals from livers for SPPVN-injected tumor-bearing mice were almost the same at each time point for different tumor sizes (5 and 1 mm$^3$) (FIG. 51). This confirmed that the tumor size did not affect the nanoparticle biodistribution. Moreover, the tumor size that SPPVN detected (1 mm$^3$) was much smaller than other reported NIR fluorescence imaging probes (50 to 500 mm$^3$) [e.g. See Li Y., et al., *Nat. Commun.* 5, 4712 (2014; Yang K., et al., *Adv. Mater.* 24, 1868-1872 (2012)].

In Vivo Peritoneal Metastatic Tumor Imaging.

To determine the origin of the faster delineation of tumor for SPPVN relative to PPVP, ex vivo biodistribution and in vitro multicellular tumor spheroids (MCTS) uptake were studied. In contrast to PPVP with the highest uptake in liver, SPPVN had the highest uptake in tumor, which was 1.4-fold higher than that in liver (FIGS. 39d and 3e, FIG. 52), which could be attributed to the more stable non-dissociable nanostructure of SPPVN as compared with the binary micellar structure of PPVP. The PEG density of nanoparticles for SPPVN was calculated ~1.7-fold higher than that of PPVP (0.30 vs 0.18/nm$^2$), which should be another reason for the better biodistribution of SPPVN according to the reported literature [e.g. See Du X., et al., *Biomaterials* 69, 1-11 (2015)]. Furthermore, MCTS uptake studies showed that SPPVN had both higher uptake (1.8-times) and deeper penetration than PPVP after the same incubation time (FIG. 53), probably due to its smaller size relative to PPVP (24 vs 34 nm). These data imply that in addition to higher afterglow of SPPVN relative to PPVP, the better biodistribution and deeper penetration capabilities of SPPVN relative to PPVP should be responsible for faster detection of tumor in living mice after systemic administration.

Figure 40:
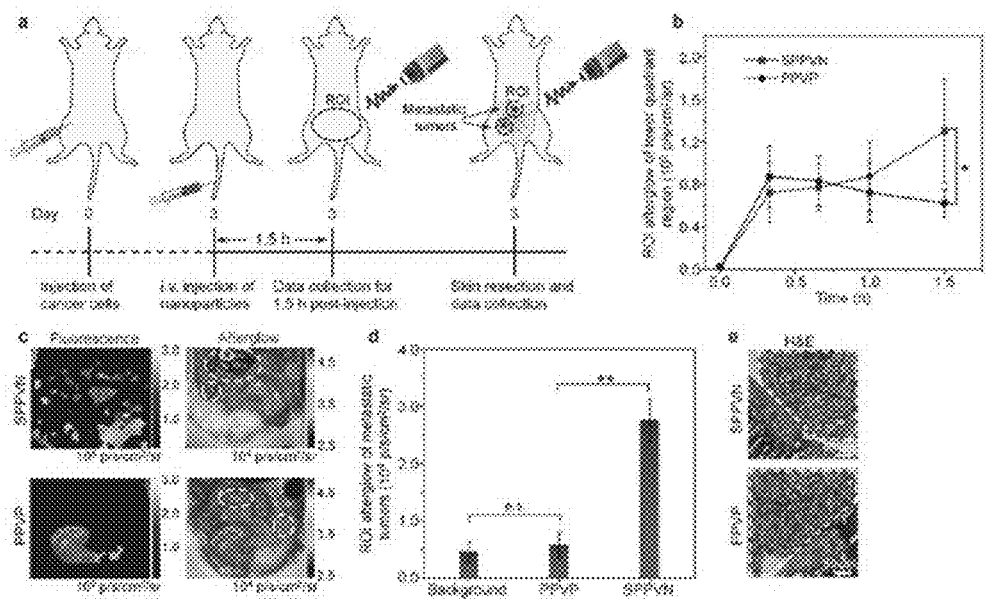

To test the utility of SPPVN over PPVP in detection of metastatic tumor tissues, the imaging experiments were conducted on the peritoneal metastatic 4T1 tumor bearing mice. 4T1 cancer cells (2×10$^5$) were intraperitoneally injected into mice to establish the metastatic tumor model. The mice were randomly divided into two groups and treated with SPPVN or PPVP through tail vein only 3 days after the injection of 4T1 cells (FIG. 40a). Fluorescence and afterglow images were acquired after systemic administration of SPPVN or PPVP through tail vein injection. The afterglow signals in the lower quadrant region (excluding liver) gradually increased for SPPVN—but not PPVP-injected mice, indicating the obviously stronger accumulation of SPPVN in tumor tissues (FIG. 40b). At t=1.5 h post-injection, skin and peritoneum of mice were resected and the lower quadrant regions of the mice were imaged. For both SPPVN and PPVP-injected mice, only autofluorescence can be detected in the lower quadrant regions. In contrast, strong afterglow spots can be detected on the intestines for SPPVN-injected mice but not for PPVP-injected mice (FIG. 40c). Quantification of afterglow signals showed that the afterglow intensity of tumor region for SPPVN-injected mice was 6.1-fold higher than the background signal, while the signal of PPVP-injected mice had no significant statistical difference from the background signal (FIG. 40d). Formation of tiny metastatic tumors on the surface of intestine, which are invisible with the naked eye, was confirmed by histological examinations (FIG. 40e and FIG. 54). These results indicated the faster detection of tiny peritoneal metastatic tumor tissues for SPPVN relative to PPVP.

Biodegradability Study

Figure 41:
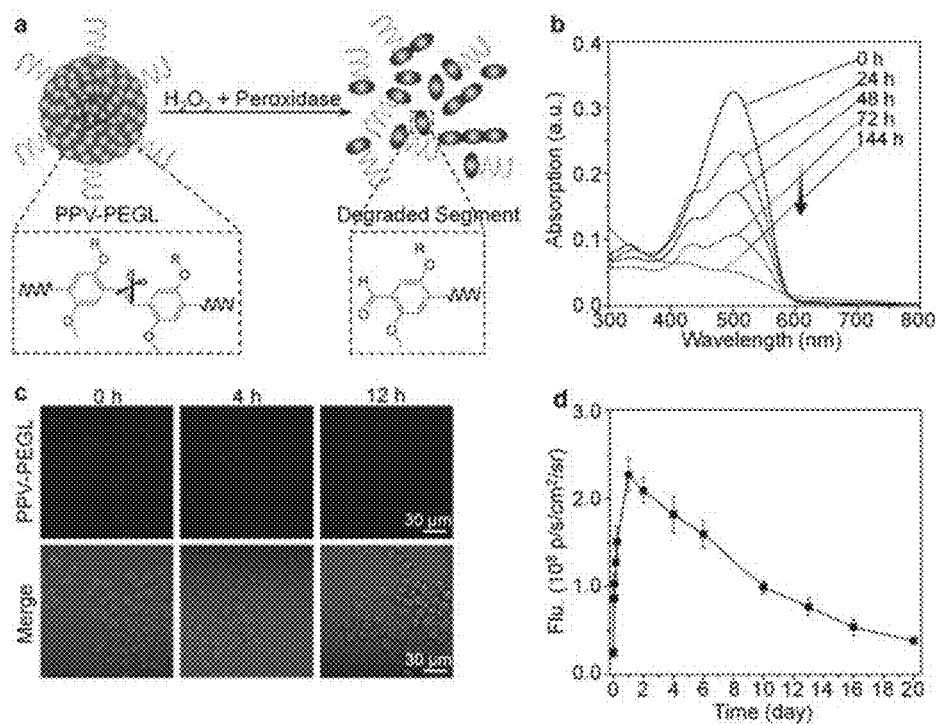

The biodegradability of PPV-PEGL was studied in solution and in cell under in vivo memetic conditions (FIG. 41a). Myeloperoxidase (MPO) and $H_2O_2$ that could be generated in immune cells [e.g. See Klebanoff S. J., *J. Leukoc. Biol.* 77, 598-625 (2005)] were used to mimic the physiological condition, and the concentration of MPO used (40 μg/mL) was in the range of the physiological concentration (35.4-82.6 μg/mL) calculated according to previous literature [e.g. See Christensen R. D. and Rothstein G., *Pediatr. Res.* 19, 1278-1282 (1985)]. Incubation of PPV-PEGL with MPO and $H_2O_2$ led to the gradual decreased and blue-shifted absorption (FIG. 41b). This confirmed the enzymatic oxidation of double bonds and the degradation of PPV-PEGL into small segments. Then, PPV-PEGL was incubated with lipopolysaccharides (LPS) activated macrophage RAW264.7 cells for different times to study the intracellular biodegradability. The fluorescence of PPV-PEGL in cells gradually decreased with the increased incubation time (FIG. 41c). At 12 h, the fluorescence was 2.3-fold lower than that of the cells without stimulation. These data demonstrated that PPV-PEGL was degradable in biologically-relevant conditions.

To study the in vivo clearance of SPPVN, SPPVN was systemic administration into living mice through tail vein, and the fluorescence images at different time points were recorded. After i.v. injection, SPPVN was gradually accumulated into liver and the highest accumulation in liver was found at 1 day post-injection (FIG. 41d and FIG. 55). Then, the fluorescence signal in liver gradually decreased and the signal was almost undetectable after 20 days post-injection.

These results indicated that SPPVN could be degraded in liver and cleared through hepatobiliary excretion within 20 days in living mice.

Example 10

Synthesis and Characterization of SPN-PPV-TPP.

1,4-Dibromo-2,5-bis((2-ethylhexyl)oxy)benzene (Preparation 8) was copolymerized with trans-1,2-Bis (tributylstannyl) ethene and different molar ratios of 7,18-dibromo-5,10,15,20-tetraphenylporphyrin (TPP-Br) to yield PPV, PPV-TPP$_{2.5\%}$ and PPV-TPP$_{5\%}$ via Pd-catalyzed Stille coupling reaction (FIG. 56a) (Preparation 10). The molecular weight and polydispersity (PDI) of PPV-TPPs were further characterized by GPC, and the molecular weights of PPV polymers were within the range of 8900 to 13000 (Table 2).

Figure 56:
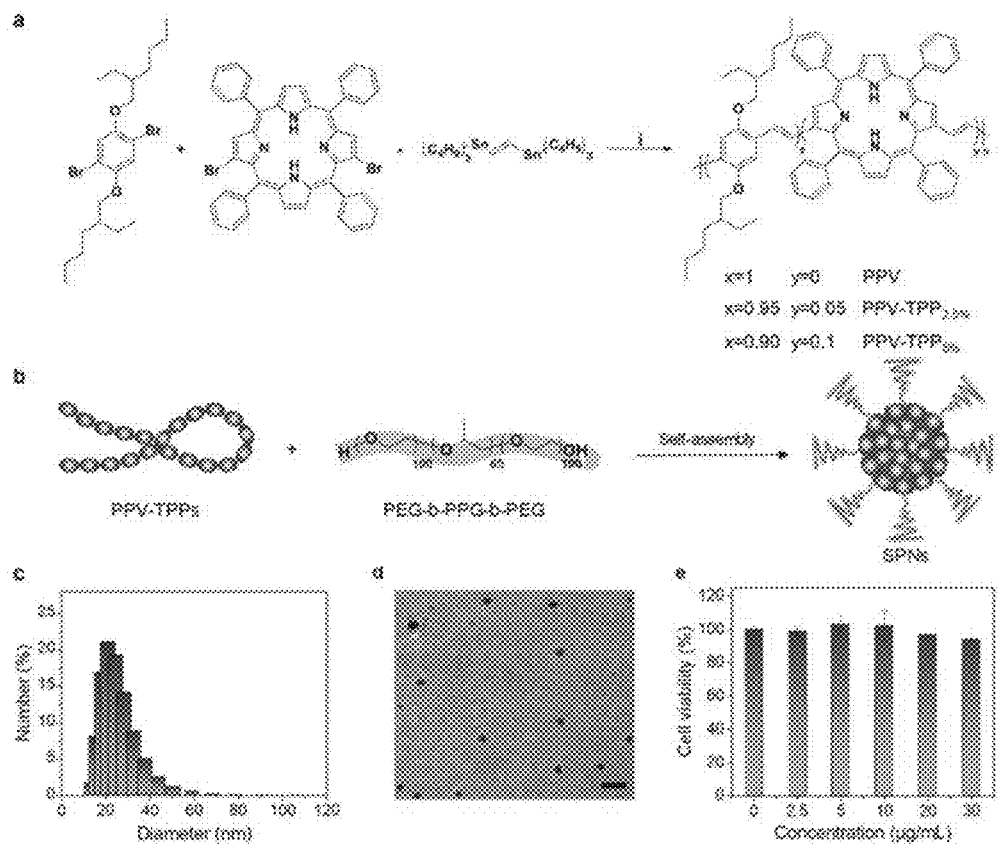

PPV-TPP (1 mg) was dissolved in 1 mL of THF. Nanoprecipitation was then used to transform PPV, PPV-TPP$_{2.5\%}$ and PPV-TPP$_{5\%}$ (0.25 mL) into water-soluble nanoparticles (SPN0, SPN2.5 and SPN5) in the presence of an amphiphilic triblock copolymer (PEG-b-PPG-b-PEG) (20 mg) in 0.75 mL of THF (FIG. 56b). The solution obtained was rapidly injected into a mixture of DI water (9 mL) and THF (1 mL) under continuous sonication. THF was removed by a gentle nitrogen flow. The resulting solution was purified by filtration through a 0.22 μm polyvinylidene fluoride syringe driven filter (Millipore). The obtained nanoparticles solutions were concentrated through ultrafiltration and then diluted with 1×PBS (pH=7.4) to prepare solutions of different concentrations.

TABLE 2

GPC data of PPV polymers.

| Sample Name | $M_n$ (g/mol) | $M_w$ (g/mol) | PDI |
|---|---|---|---|
| PPV | 8947 | 12613 | 1.4 |
| PPV-TPP$_{2.5\%}$ | 11469 | 14478 | 1.26 |
| PPV-TPP$_{5\%}$ | 12781 | 17016 | 1.33 |

DLS shows that the average hydrodynamic diameters of SPN0, SPN2.5 and SPN5 were similar, ranging from 25 to 30 nm (FIG. 56c and FIG. 60). Taking SPN2.5 as the example, TEM imaging reveals a uniform spherical morphology with an average diameter of ~25 nm, identical to the DLS data (FIG. 56d). No precipitation or obvious change in size was observed for SPN2.5 after storage in PBS (pH=7.4) or FBS for 20 days (FIG. 61). MTS assay (as described in the biological tests section) showed that SPN2.5 was not cytotoxic to 4T1 cells (FIG. 56e). These results indicate that these SPN-PPV-TPPs have ideal aqueous stability and cytocompatibility for biological applications.

Figure 57:
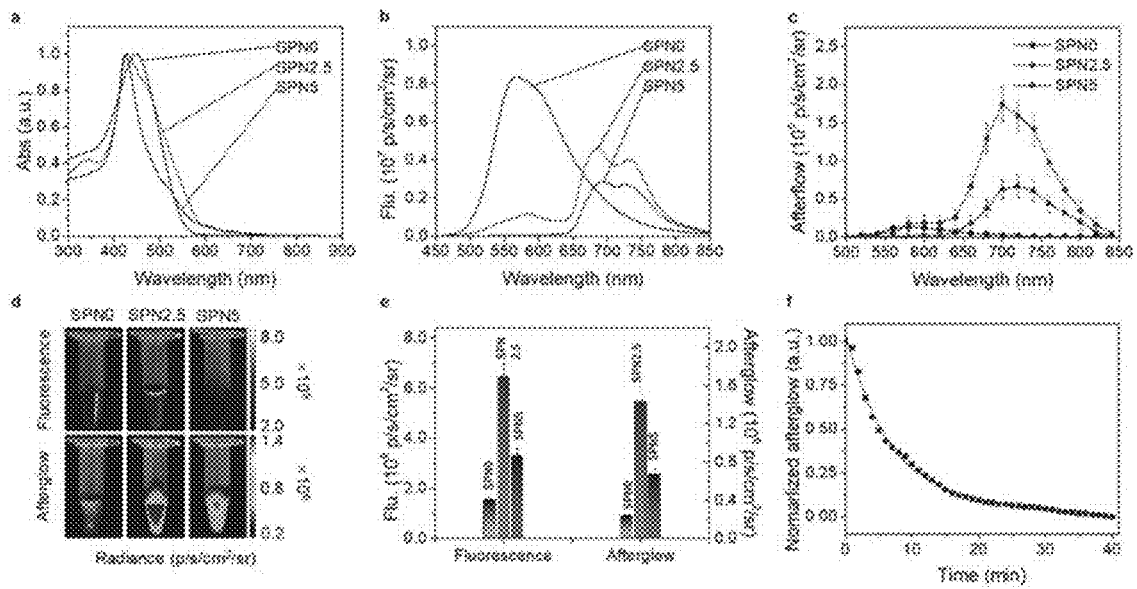

The optical properties of SPN-PPV-TPPs were tested in PBS (pH=7.4) solution. The UV-Vis spectra showed that all the SPN-PPV-TPPs have similar maximum absorption ranging from 430 to 450 nm corresponding to the PPV segment (FIG. 57a). With increased amount of TPP, a new absorption band ranging from 600 to 700 nm appeared, which was assigned to the TPP-containing segments. Such change in absorption verified the incorporation of TPP into the backbone of PPV-TPPs. The fluorescence of TPP-free nanoparticle (SPN0) had a visible emission with the maximum at 580 nm. With increased amount of TPP, the fluorescence of PPV segment at 580 nm decreased accompanied with increased NIR emission ranging from 650 to 750 nm (FIG. 57b), and the saturation occurred at 2.5% amount of TPP (SPN2.5). This confirmed the occurrence of FRET from PPV segments to TPP. Compared with SPN2.5, SPN5 showed decreased emission from 650 to 750 nm, probably because of the local fluorescence quenching induced by higher amount of TPP. The fluorescence images of SPN-PPV-TPPs at 720 nm captured by IVIS also confirmed this phenomenon, showing the highest fluorescence intensity for SPN2.5 among these nanoparticles (FIG. 57d). The afterglow spectra and images of SPN-PPV-TPPs were collected after light irradiation under bioluminescence modes (without real-time excitation) (FIGS. 57c and 57e), showing the afterglow spectra similar to their fluorescence spectra.

Example 11

Mechanistic Study of Afterglow for SPN-PPV-TPPs.

Similar to Example 3, $^1O_2$ sensor green (SOSG) was used to test the generation of $^1O_2$ during light irradiation. After light irradiation for 4 min, the fluorescence intensities of SOSG at 528 nm in the presence of SPN0, SPN2.5 and SPN5 (synthesized based on Example 10) increased by 6.44-, 7.78- and 9.96-fold relative to that before light irradiation, respectively (FIG. 62). This data proves that the higher amount of TPP, the more $^1O_2$ generated during light irradiation. Further, the afterglow intensity of SPN2.5 could be increased by 1.90-fold when measured in $^1O_2$-saturated condition, while decreased by 4.06-fold when measured in $N_2$-saturated condition (FIG. 63). The addition of a $^1O_2$ scavenger (NaN$_3$) could reduce the afterglow intensity by 1.58-fold. Therefore, the generated singlet oxygen ($^1O_2$) under light irradiation oxidized the vinylene bond of PPV to form an unstable PPV-dioxetane intermediate, which produced photons upon degradation. The quantification data further showed that the afterglow intensity of SPN2.5 was ~6.12 and ~2.14-fold higher than that of SPN0 and SPN5, respectively, which was consistent with their fluorescence intensity at 720 nm (FIG. 57e). In addition, the afterglow luminescence half-life of SPN2.5 was 5 min at room temperature (FIG. 57f), sufficiently long for imaging acquisition. These data suggested that incorporation of TPP into the backbone of PPV could amplify and red-shift its afterglow signal. SPN2.5 was chosen for in vivo imaging experiments as it has the brightest afterglow intensity among the SPN-PPV-TPPs.

Example 12

In Vivo Evaluation of SPN-PPV-TPPs

Next, in vivo evaluation of SPN-PPV-TPPs (synthesized based on Example 10) was conducted in accordance to the protocols in the biological tests section.

In Vivo Imaging for Differentiating Hypoxia and Normoxia Environment.

Deoxygenated SPN2.5 solution was locally injected into a tumor or under the skin (FIG. 58a). The fluorescence images of the mice were acquired at 720 nm upon excitation at 500 nm, while the afterglow luminescence images were obtained with a 30 s acquisition time with an open filter after pre-irradiation with white light for 1 min (FIG. 58a). Signal quantification clearly showed that the afterglow intensity of locally injected skin was 3.56-fold higher than that of tumor while the fluorescence intensities between skin and tumor were almost the same (FIG. 58b). This phenomenon was attributed to the hypoxia environment of tumor, which had a low oxygen level that reduced the generation of $^1O_2$ and in turn the afterglow intensity of SPN2.5. These data indicated that afterglow luminescence of SPN2.5 could be used to distinguish hypoxia from normoxia environment in living mice.

In Vivo Peritoneal Metastatic Tumor Imaging.

Figure 59:
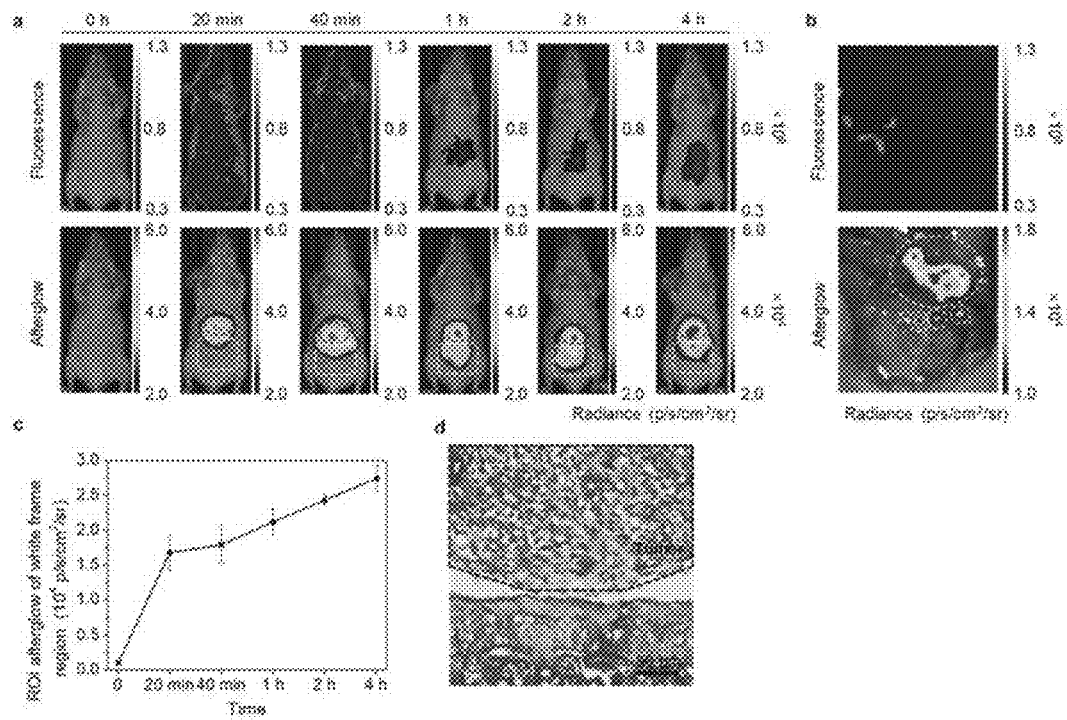

To test the ability of SPN2.5 in imaging of metastatic tumor tissues, the peritoneal metastatic tumor mouse model was established by injecting 4T1 cell suspension (200 μL, 4×10$^5$) intraperitoneally into nude mice. The mice were treated with SPN2.5 through tail vein 4 d after the injection of cancer cells. Fluorescence and afterglow images were acquired after injection of SPN2.5 through tail veil injection. Obvious afterglow signal from the liver (indicated by black circle) of the mice could be seen at t=20 min post-injection, while fluorescence signal of liver could only be detected after 1 h (FIG. 59a). This phenomenon was attributed to the higher tissue penetration of afterglow imaging than that of fluorescence imaging. As time passed, the afterglow intensity of lower quadrant region of mice (indicted by white frame) gradually increased because of the accumulation of SPN2.5 at the tumor site (FIGS. 59a and 59c). At t=4 h post-injection, obvious afterglow signal could be detected in the lower quadrant region of mice, while no obvious fluorescence signal was detected (FIG. 59a). The skin and peritoneum of mice were removed at t=4 h post-injection and the lower quadrant region of mice were imaged by both afterglow and fluorescence. Due to the high sensitivity of afterglow, strong afterglow spots can be detected on the intestines, while only autofluorescence can be detected in the abdominal cavity (FIG. 59b). Histological examinations further confirmed the presence of very small metastatic tumors on the surface of intestine (FIG. 59d) that are invisible the naked eye. These results indicate that SPN2.5 could be used as a potential afterglow imaging agent for in vivo detection of metastatic tumors.

REFERENCES

1. Ntziachristos, V., Ripoll, J., Wang, L. H. V. & Weissleder, R. Looking and listening to light: the evolution of whole-body photonic imaging. *Nat Biotechnol* 23, 313-320 (2005).
2. Smith, A. M., Mancini, M. C. & Nie, S. Bioimaging: second window for in vivo imaging. *Nat Nanotechnol* 4, 710-711 (2009).
3. Chu, J. et al. A bright cyan-excitable orange fluorescent protein facilitates dual-emission microscopy and enhances bioluminescence imaging in vivo. *Nat Biotechnol* 34, 760-767 (2016).
4. Thorek, D. L., Ogirala, A., Beattie, B. J. & Grimm, J. Quantitative imaging of disease signatures through radioactive decay signal conversion. *Nat Med* 19, 1345-1350 (2013).
5. So, M. K., Xu, C., Loening, A. M., Gambhir, S. S. & Rao, J. Self-illuminating quantum dot conjugates for in vivo imaging. *Nat Biotechnol* 24, 339-343 (2006).
6. Liu, H. et al. Intraoperative imaging of tumors using Cerenkov luminescence endoscopy: a feasibility experimental study. *J. Nucl. Med.* 53, 1579-1584 (2012).
7. de Chermont, Q. L. et al. Nanoprobes with near-infrared persistent luminescence for in vivo imaging. *Proc. Natl. Acad. Sci. USA* 104, 9266-9271 (2007).
8. Maldiney, T. et al. Controlling electron trap depth to enhance optical properties of persistent luminescence nanoparticles for In vivo imaging. *J Am Chem Soc* 133, 11810-11815 (2011).
9. Maldiney, T. et al. The in vivo activation of persistent nanophosphors for optical imaging of vascularization, tumours and grafted cells. *Nat Mater* 13, 418-426 (2014).
10. Li, Z. J. et al. Direct Aqueous-Phase Synthesis of Sub-10 nm "Luminous Pearls" with Enhanced in Vivo Renewable Near-Infrared Persistent Luminescence. *J Am Chem Soc* 137, 5304-5307 (2015).
11. Maldiney, T. et al. In vivo optical imaging with rare earth doped Ca$_2$Si$_5$N$_8$ persistent luminescence nanoparticles. *Opt Mater Express* 2, 261-268 (2012).
12. Abdukayum, A., Chen, J. T., Zhao, Q. & Yan, X. P. Functional Near Infrared-Emitting Cr$^{3+}$/Pr$^{3+}$ Co-Doped Zinc Gallogermanate Persistent Luminescent Nanoparticles with Superlong Afterglow for in Vivo Targeted Bioimaging. *J Am Chem Soc* 135, 14125-14133 (2013).
13. Liu, F. et al. Photostimulated near-infrared persistent luminescence as a new optical read-out from Cr$^{3+}$-doped LiGa$_5$O$_8$. *Sci Rep-Uk* 3 (2013).
14. Maldiney, T. et al. In vivo imaging with persistent luminescence silicate-based nanoparticles. *Opt Mater* 35, 1852-1858 (2013).
15. Sharma, S. K. et al. Persistent luminescence of AB$_2$O$_4$: Cr$^{3+}$ (A=Zn, Mg, B=Ga, Al) spinels: New biomarkers for in vivo imaging. *Opt Mater* 36, 1901-1906 (2014).
16. Shi, J. P. et al. Multifunctional near infrared-emitting long-persistence luminescent nanoprobes for drug delivery and targeted tumor imaging. *Biomaterials* 37, 260-270 (2015).
17. Toppari, J. et al. Male reproductive health and environmental xenoestrogens. *Environ. Health Perspect.* 104 Suppl 4, 741-803 (1996).
18. Kobayashi, H. & Choyke, P. L. Target-cancer-cell-specific activatable fluorescence imaging probes: rational design and in vivo applications. *Acc. Chem. Res.* 44, 83-90 (2011).
19. Lovell, J. F., Liu, T. W., Chen, J. & Zheng, G. Activatable photosensitizers for imaging and therapy. *Chem Rev* 110, 2839-2857 (2010).
20. Feng, L. et al. Conjugated polymer nanoparticles: preparation, properties, functionalization and biological applications. *Chem Soc Rev* 42, 6620-6633 (2013).
21. Wu, C. & Chiu, D. T. Highly fluorescent semiconducting polymer dots for biology and medicine. *Angew Chem Int Edit* 52, 3086-3109 (2013).
22. Dodeigne, C., Thunus, L. & Lejeune, R. Chemiluminescence as a diagnostic tool. A review. *Talanta* 51, 415-439 (2000).
23. Maldiney, T. et al. Effect of Core Diameter, Surface Coating, and PEG Chain Length on the Biodistribution of Persistent Luminescence Nanoparticles in Mice. *ACS Nano* 5, 854-862 (2011).
24. Shuhendler, A. J., Pu, K. Y., Cui, L., Uetrecht, J. P. & Rao, J. H. Real-time imaging of oxidative and nitrosative stress in the liver of live animals for drug-toxicity testing. *Nat Biotechnol* 32, 373-380 (2014).
25. Scurlock, R. D., Wang, B. J., Ogilby, P. R., Sheats, J. R. & Clough, R. L. Singlet Oxygen as a Reactive Intermediate in the Photodegradation of an Electroluminescent Polymer. *J Am Chem Soc* 117, 10194-10202 (1995).
26. Kim, S. et al. Near-infrared fluorescent type II quantum dots for sentinel lymph node mapping. *Nat Biotechnol* 22, 93-97 (2004).
27. Nasr, A., Lauterio, T. J. & Davis, M. W. Unapproved drugs in the United States and the Food and Drug Administration. *Adv. Ther.* 28, 842-856 (2011).

28. Kola, I. & Landis, J. Can the pharmaceutical industry reduce attrition rates? *Nat Rev Drug Discov* 3, 711-715 (2004).
29. Willmann, J. K., van Bruggen, N., Dinkelborg, L. M. & Gambhir, S. S. Molecular imaging in drug development. *Nat Rev Drug Discov* 7, 591-607 (2008).
30. Pessayre, D., Mansouri, A., Berson, A. & Fromenty, B. Mitochondrial involvement in drug-induced liver injury. *Handb. Exp. Pharmacol.,* 311-365 (2010).
31. Longmire, M., Choyke, P. L. & Kobayashi, H. Clearance properties of nano-sized particles and molecules as imaging agents: considerations and caveats. *Nanomedicine* 3, 703-717 (2008).
32. Pu, K. Y., Chattopadhyay, N. & Rao, J. H. Recent advances of semiconducting polymer nanoparticles in in vivo molecular imaging. *J. Control. Release* 240, 312-322 (2016).
33. R. D. Scurlock, B. Wang, P. R. Ogilby, J. R. Sheats, R. L. Clough. Singlet Oxygen as a Reactive Intermediate in the Photodegradation of an Electroluminescent Polymer. *J. Am. Chem. Soc.* 117, 10194-10202 (1995).
34. X. Zhen, C. Zhang, C. Xie, Q. Miao, K. L. Lim, K. Pu. Intraparticle Energy Level Alignment of Semiconducting Polymer Nanoparticles to Amplify Chemiluminescence for Ultrasensitive In Vivo Imaging of Reactive Oxygen Species. *ACS Nano* 10, 6400-6409 (2016).
35. A. J. Shuhendler, K. Pu, L. Cui, J. P. Uetrecht, J. Rao. Real-time imaging of oxidative and nitrosative stress in the liver of live animals for drug-toxicity testing. *Nat. Biotechnol.* 32, 373-380 (2014).
36. Q. Miao, C. Xie, X. Zhen, Y. Lyu, H. Duan, X. Liu, J. V. Jokerst, K. Pu. Molecular afterglow imaging with bright, biodegradable polymer nanoparticles. *Nat. Biotechnol.* 35, 1102-1110 (2017).
37. T. Lecuyer, E. Teston, G. Ramirez-Garcia, T. Maldiney, B. Viana, J. Seguin, N. Mignet, D. Scherman, C. Richard. Chemically engineered persistent luminescence nanoprobes for bioimaging. *Theranostics* 6, 2488-2524 (2016).
38. Y. Li, T. Lin, Y. Luo, Q. Liu, W. Xiao, W. Guo, D. Lac, H. Zhang, C. Feng, S. Wachsmann-Hogiu, J. H. Walton, S. R. Cherry, D. J. Rowland, D. Kukis, C. Pan, K. S. Lam. A smart and versatile theranostic nanomedicine platform based on nanoporphyrin. *Nat. Commun.* 5, 4712 (2014).
39. K. Yang, L. Hu, X. Ma, S. Ye, L. Cheng, X. Shi, C. Li, Y. Li, Z. Liu. Multimodal imaging guided photothermal therapy using functionalized graphene nanosheets anchored with magnetic nanoparticles. *Adv. Mater.* 24, 1868-1872 (2012).
40. C. Xie, X. Zhen, Q. Lei, R. Ni, K. Pu. Self-Assembly of Semiconducting Polymer Amphiphiles for In Vivo Photoacoustic Imaging. *Adv. Funct. Mater.* 27, 1605397 (2017).
41. D. Cui, C. Xie, Y. Lyu, X. Zhen, K. Pu. Near-infrared absorbing amphiphilic semiconducting polymers for photoacoustic imaging. *J. Mater. Chem. B* 5, 4406-4409 (2017).
42. X. Du, J. Wang, W. Liu, J. Yang, C. Sun, R. Sun, H. Li, S. Shen, Y. Luo, X. Ye, Y. Zhu, X. Yang, J. Wang. Regulating the surface poly(ethylene glycol) density of polymeric nanoparticles and evaluating its role in drug delivery in vivo. *Biomaterials* 69, 1-11 (2015).
43. S. J. Klebanoff. Myeloperoxidase: friend and foe. *J. Leukoc. Bio.* 77, 598-625 (2005).
44. R. D. Christensen, G. Rothstein. Neutrophil myeloperoxidase concentration: changes with development and during bacterial infection. *Pediatr. Res.* 19, 1278-1282 (1985).
45. P. Carmeliet, R. K. Jain. Molecular mechanisms and clinical applications of angiogenesis. *Nature.* 473, 298-307 (2011).

The invention claimed is:

1. A polymeric composite nanoparticle that emits near-infrared afterglow luminescence, the nanoparticle comprising:

(a) a semiconducting polymer of formula (I):

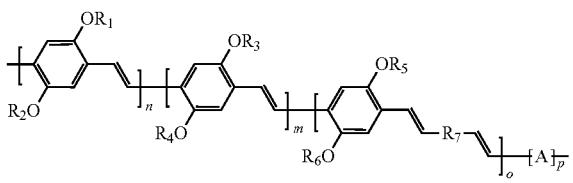

(b) optionally, an amphiphilic copolymer; and
(c) optionally, a molecular dye with near-infrared emission; wherein:
when the amphiphilic copolymer is present, the amphiphilic copolymer encapsulates the semiconducting polymer of formula (I) and, when the amphiphilic copolymer and the molecular dye are both present, the amphiphilic copolymer encapsulates the semiconducting polymer of formula (I) and the molecular dye; and
wherein the polymer of formula (I) is a random copolymer, and in the polymer of formula (I):
$R_1$ to $R_3$ and $R^5$ independently represent an alkyl chain of the formula $C_qH_{2q+1}$, where $1 \leq q \leq 50$,
$R_4$ represents a moiety of formula (Ia) or formula (Ib):

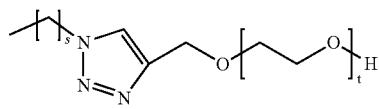

where $1 \leq s \leq 50$ and $10 \leq t \leq 500$;

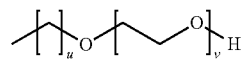

where $1 \leq u \leq 50$ and $10 \leq v \leq 500$;

$R_6$ represents an alkyl chain of the formula $C_qH_{2q+1}$, a moiety of formula Ia or a moiety of formula Ib where q, s, t, u and v are as defined above;

$R_7$ represents a singlet oxygen sensitizing moiety;

each of n, m and o are each greater than or equal to 0 and p is 0 or 1, where at least one of n, m, o and p are greater than 0;

A represents a moiety of formula (Ic) or (Id):

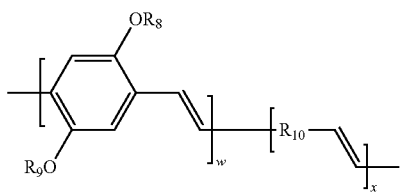

(Ic)

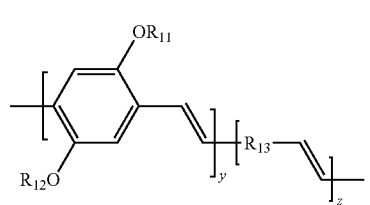

(Id)

where $R_8$ and $R_{11}$ independently represent an alkyl chain of the formula $C_qH_{2q+1}$, where:

$1 \leq q \leq 50$;

$R_9$ and $R_{12}$ independently represent an alkyl chain of the formula $C_qH_{2q+1}$, a moiety of formula (Ia) or a moiety of formula (Ib), where q, s, t, u and v are as defined above;

$R_{10}$ and $R_{13}$ independently represent a singlet oxygen sensitizing moiety;

when p is 1, then w, x, y and z are independently greater than or equal to 0, provided that at least one of w and x are greater than 0 and at least one of y and z are greater than 0; and provided that when n is greater than 0, one or more of m, o and p are also greater than 0; wherein the molecular dye is present when o and p are 0 and is optionally present when:
o is greater than or equal to 20;
p is 1 and x or z is greater than or equal to 20;
the sum of o and x is greater than or equal to 20;
the sum of o and z is greater than or equal to 20;

$(o+x)/(n+m+o+w+x) > 0.05$; or $(o+z)/(n+m+o+y+z) > 0.05$;

the amphiphilic copolymer is present when m, o and p are 0 and optionally present when:

$(m+o+w)/(n+m+o+w+x) > 0.1$; or $(m+o+y)/(n+m+o+y+z) > 0.1$.

2. The composite according to claim 1, wherein n is 0.

3. The composite according to claim 1, wherein one or more of the following clauses applies:
(a) p is 0
(b) the amphiphilic copolymer is present;
(c) each of n, m, o, w, x, y and z independently has a value of from 5 to 1000; or (d) the number average molecular weight of the polymer of formula (I) is from 1,000 to 300,000 Daltons.

4. The composite pigment according to claim 2, wherein p is 0 and the amphiphilic copolymer is optionally present when:

m is greater than or equal to 20 and m/(n+m+o) is greater than 0.1 and $R^6$ is $C_qH_{2q+1}$, where $1 \leq q \leq 50$;

m is greater than or equal to 20 and (m+o)/(x+y+z) is greater than 0.1 and $R^6$ is a moiety of formula (Ia) or a moiety of formula (Ib); or o is greater than or equal to 20 and (m+o)/(x+y+z) is greater than 0.1 and $R^6$ is a moiety of formula (Ia) or a moiety of formula (Ib).

5. The composite according to claim 1, wherein the singlet oxygen sensitizing moiety $R_7$, $R_{10}$ and $R_{13}$ is independently selected from one or more of the group consisting of metallo-phthalocyanines, naphthalocyanines, metallo-naphthalocyanines, chlorins, rhodamine, cyanine, carotenoid, anthocyanin, rose bengal, methylene blue, silicon 2,3-naphthalocyanine bis (trihexylsilyloxide), porphyrins, phthalocyanines, tetrapyrroles, transition metal complexes and boron-dipyrromethene (BODIPY)-based photosensitizers.

6. The composite according to claim 1, wherein the polymer of formula (I) is selected from the list of:

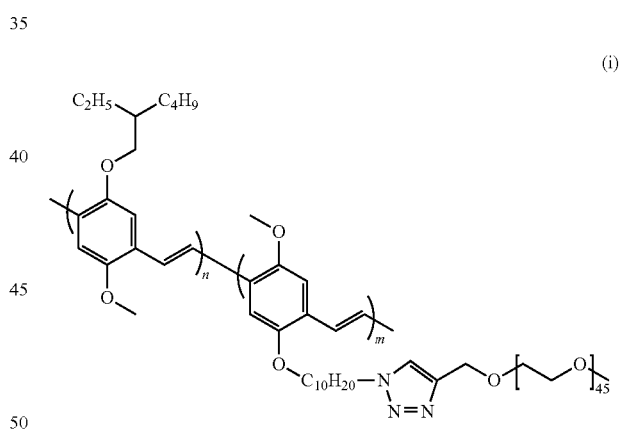

(i)

where n and m are as defined in claim 1;

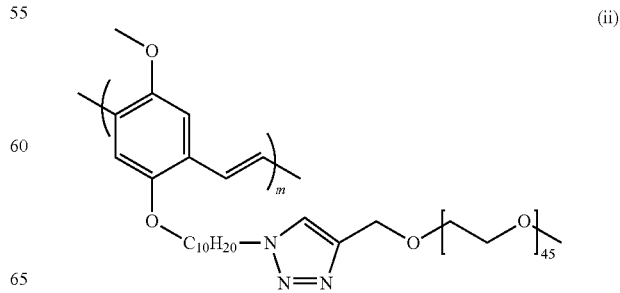

(ii)

where m is as defined in claim 1; and

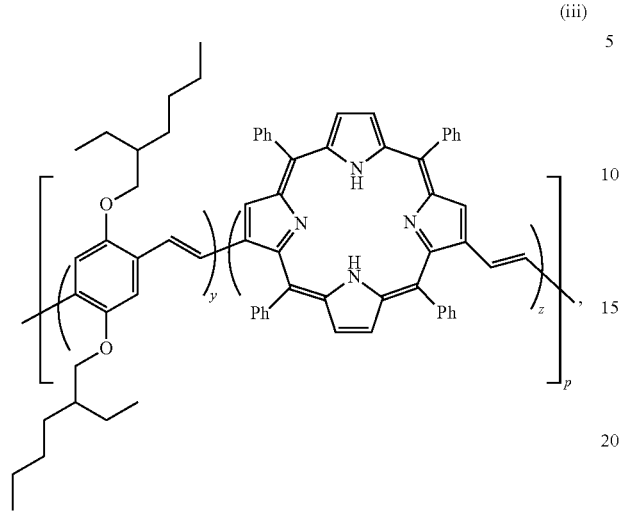

where p is 1 and the number of y and z repeating units provide a polymer having a number average molecular weight of from 5,000 to 20,000 Daltons and/or the molar ratio of y repeating units in the polymer is from 85 to 99% and the molar ratio of z repeating units in the polymer is from 1 to 15%.

7. The composite according to claim 1, wherein one or more of the following clauses applies:
 (a) the weight to weight ratio of the amphiphilic copolymer to the polymer of formula (I) is from 1:1 to 200:1;
 (b) the molecular dye with near-infrared emission is a singlet oxygen sensitizing compound selected from one or more of the group consisting of metallo-phthalocyanines, naphthalocyanines, metallo-naphthalocyanines, chlorins, rhodamine, cyanine, carotenoid, anthocyanin, rose bengal, methylene blue, silicon 2,3-naphthalocyanine bis (trihexylsilyloxide), porphyrins, phthalocyanines, tetrapyrroles, transition metal complexes and boron-dipyrromethene (BODIPY)-based photosensitizers;
 (c) the amphiphilic copolymer is selected from one or more of the group consisting of alky-substituted chitosan, and poly (alkyl)-b-poly (ethylene glycol), poly (ethylene glycol)-b-poly (propylene glycol)-b-poly (ethylene glycol), poly (ethylene glycol) methyl ether-block-poly (lactide-co-glycolide) (PEG-PLGA), poly (styrene)-block-poly (acrylic acid) (PS-PAA), poly (styrene-co-maleic anhydride) (PSMA), 1,2-dipalmitoyl-sn-glycero-3-phosphocholine (DPPC) and 1,2-distearoyl-sn-glycero-3-phosphoethanolamine-poly (ethylene glycol) (DSPE-PEG); or
 (d) the amphiphilic copolymer is selected from one or more of the group consisting of poly(ethylene glycol)-b-poly(propylene glycol)-b-poly(ethylene glycol), 1,2-distearoyl-sn-glycero-3-phosphoethanolamine-poly (ethylene glycol) (DSPE-PEG), and

8. The composite according to claim 1, wherein the amphiphilic copolymer further comprises a quenching moiety that is cleavable by a reactive moiety in an in vitro or in vivo site of action.

9. The composite material of claim 8, wherein the cleavable quenching moiety is a Dark Quencher.

10. The composite according to claim 9, wherein the Dark Quencher is selected from the group consisting of a Black Hole Quencher (BHQ)-1, BHQ-2, BHQ-3, and QSY-7.

11. The composite according to claim 8, wherein the amphiphilic copolymer comprising a quenching moiety is selected from one or more of the group consisting of

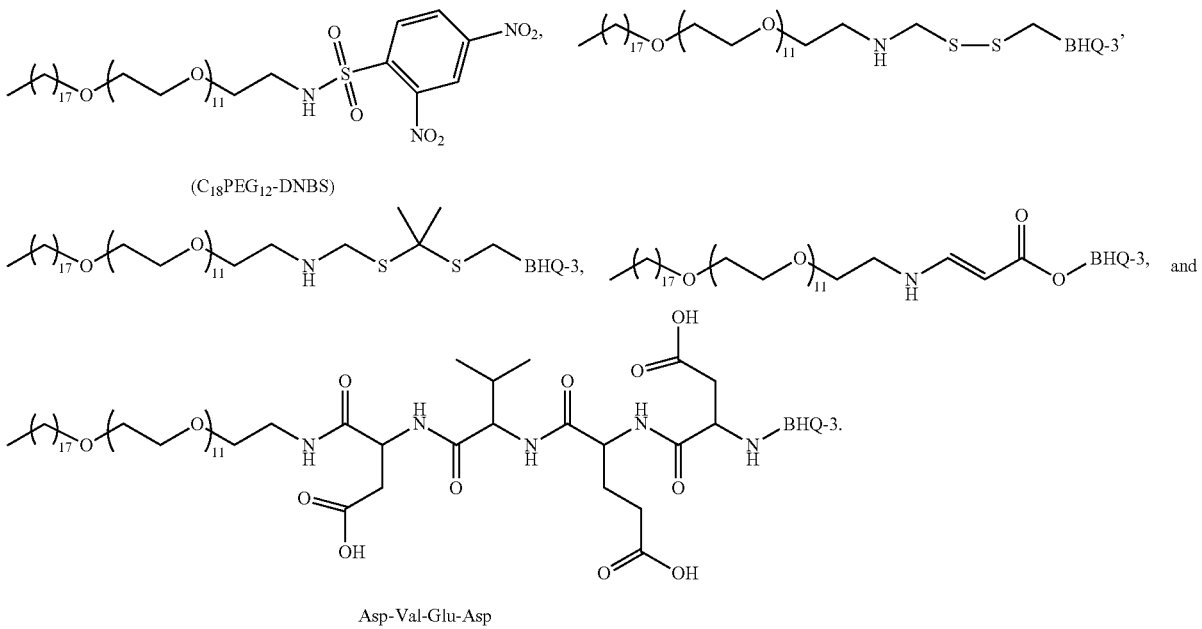

Asp-Val-Glu-Asp

12. The composite according to claim 1, wherein the polymer of formula (I) is:

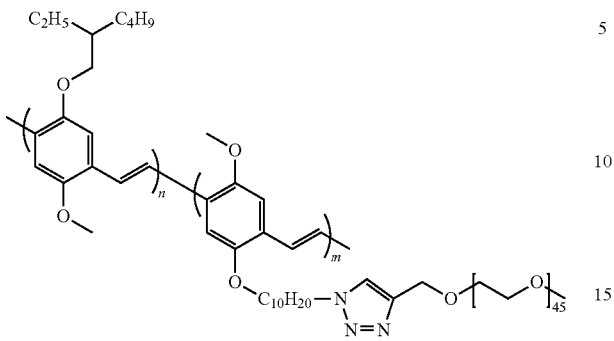

wherein n and m are as defined in claim 1, and wherein the number of n and m repeating units provides a polymer having a number average molecular weight of from 25,000 to 200,000 Daltons and/or the molar ratio of n repeating units in the polymer is around 88% and the molar ratio of m repeating units in the polymer is around 11%.

13. The composite according to claim 1, wherein the polymer of formula (I) is:

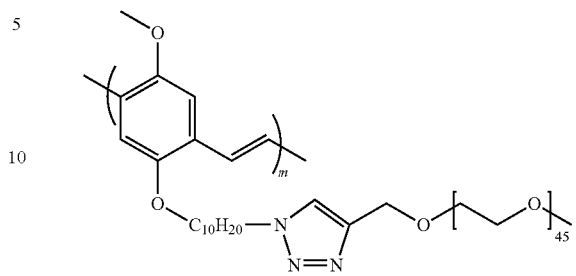

where m is as defined in claim 1, and wherein the number of m repeating units provides a polymer having a number average molecular weight of from 15,000 to 100,000 Daltons.

14. The composite according to claim 7, wherein the amphiphilic copolymer has a number average molecular weight of from 1,000 to 50,000 Daltons.

* * * * *